United States Patent
Weissleder et al.

(10) Patent No.: US 10,557,847 B2
(45) Date of Patent: Feb. 11, 2020

(54) NANO-PLASMONIC SENSOR FOR EXOSOME DETECTION

(71) Applicant: THE GENERAL HOSPITAL CORPORATION, Boston, MA (US)

(72) Inventors: Ralph Weissleder, West Peabody, MA (US); Hakho Lee, Acton, MA (US); Hyungsoon Im, Peabody, MA (US); Cesar Castro, Cambridge, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 614 days.

(21) Appl. No.: 15/100,997

(22) PCT Filed: Dec. 2, 2014

(86) PCT No.: PCT/US2014/068084
§ 371 (c)(1),
(2) Date: Jun. 2, 2016

(87) PCT Pub. No.: WO2015/084800
PCT Pub. Date: Jun. 11, 2015

(65) Prior Publication Data
US 2016/0334398 A1    Nov. 17, 2016

Related U.S. Application Data

(60) Provisional application No. 61/910,782, filed on Dec. 2, 2013.

(51) Int. Cl.
*G01N 33/553* (2006.01)
*G01N 33/543* (2006.01)
*G01N 33/574* (2006.01)

(52) U.S. Cl.
CPC ..... *G01N 33/54373* (2013.01); *G01N 33/553* (2013.01); *G01N 33/57449* (2013.01); *G01N 2333/70596* (2013.01)

(58) Field of Classification Search
None
See application file for complete search history.

(56) References Cited

U.S. PATENT DOCUMENTS

2009/0148346 A1*  6/2009  Ban .................. B82Y 15/00
                                                 422/82.05
2012/0184047 A1   7/2012  Jonsson et al.
(Continued)

OTHER PUBLICATIONS

Victoria, "Application of Surface Plasmon Resonance (SPR) for the Detection of Single Viruses and Single Biological Nano-objected", J Bacteriol Parasitol, 3(7): 1000e110 (2012).
(Continued)

*Primary Examiner* — Christopher L Chin
(74) *Attorney, Agent, or Firm* — Nixon Peabody LLP; David S. Resnick; Shayne Y. Huff

(57) ABSTRACT

Disclosed herein are compositions and methods for exosome detection with high sensitivity by using a nano-plasmonic sensor. The nano-plasmonic sensor comprises a plurality of nanoapertures suitable for transmission measurements. The detection sensitivity is on the order of $10^4$-fold higher than western blotting and $10^2$-fold higher than enzyme-linked immunosorbent assay (ELISA). A portable imaging system is also disclosed, enabling rapid and high-throughput detection of exosomes. The nano-plasmonic sensor and imaging system can be useful in diagnostics.

17 Claims, 40 Drawing Sheets

(56) References Cited

U.S. PATENT DOCUMENTS

2013/0065777 A1* 3/2013 Altug .................. G01N 21/554
506/9
2014/0349278 A1* 11/2014 Yamamoto ........... G01N 21/554
435/5

OTHER PUBLICATIONS

Yang et al., "Metallic Nanohole Arrays on Fluoropolymer Substrates as Small Label-Free Real-Time Bioprobes", Nano Lett, 8(9): 2718-2724 (2008).

* cited by examiner

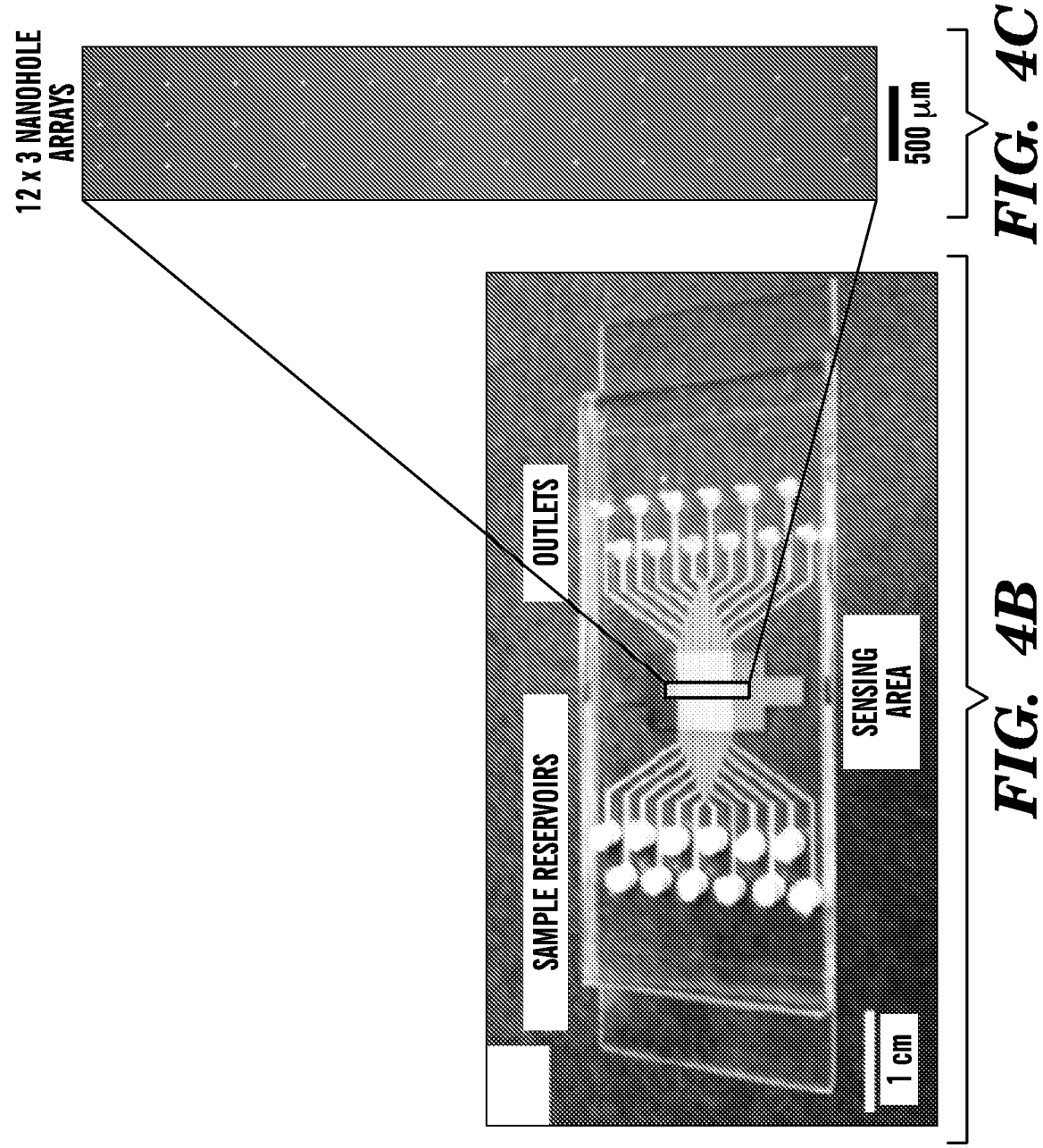

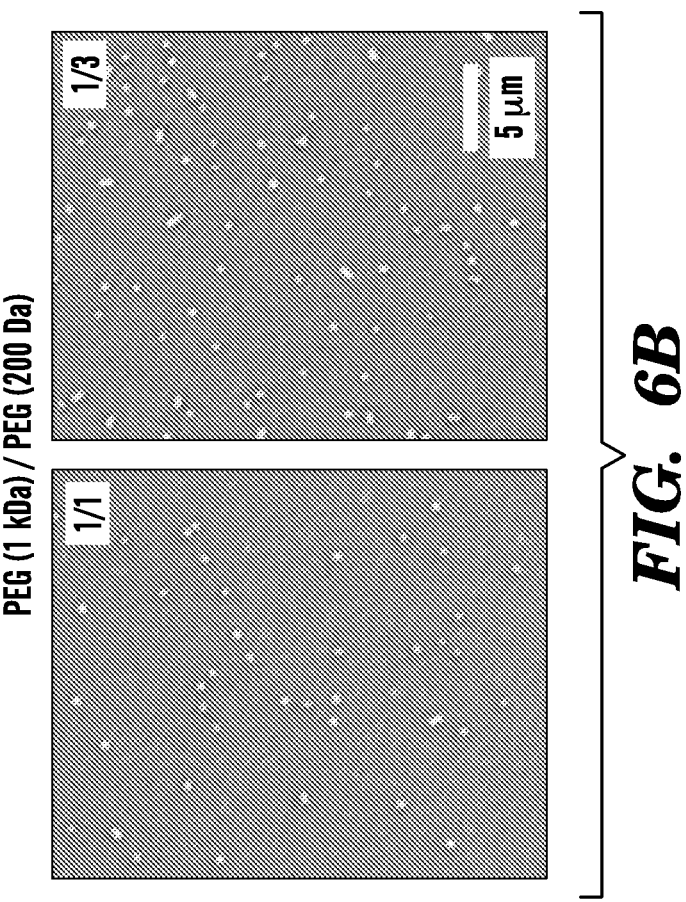
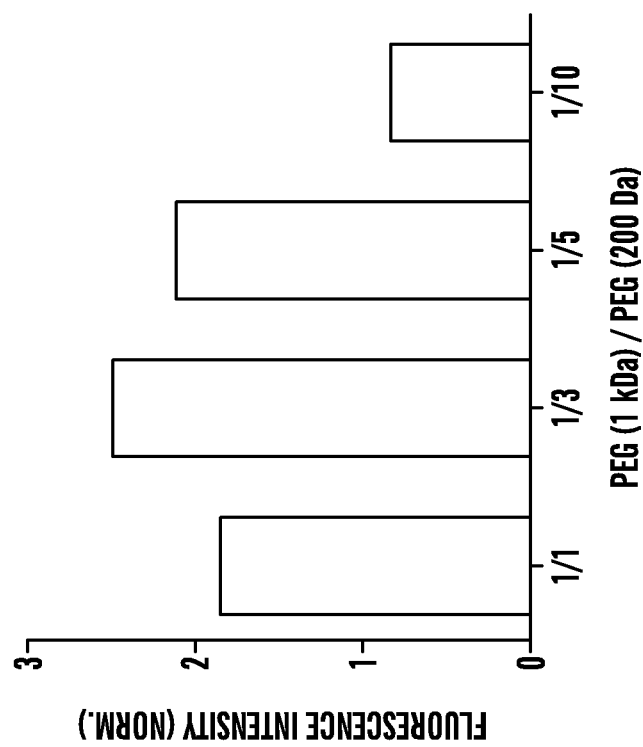
FIG. 6A
FIG. 6B

| ANTIBODY | NET SPECTRAL SHIFT (nm) | |
| --- | --- | --- |
| | AFTER ANTIBODY CONJUGATION | AFTER EXOSOME CAPTURE |
| CD63 | 3.71 ± 0.35 | 2.49 ± 0.01 |
| IgG CONTROL | 3.76 ± 0.29 | 0.10 ± 0.00 |

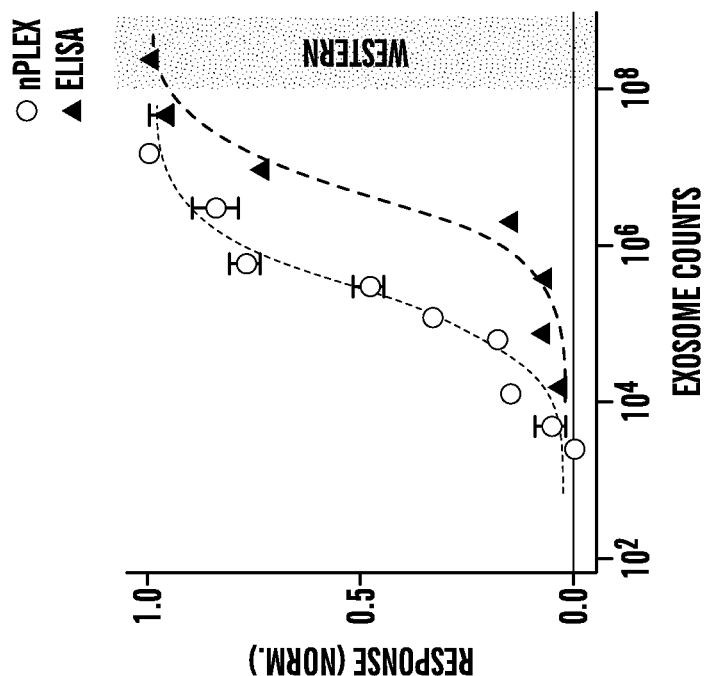
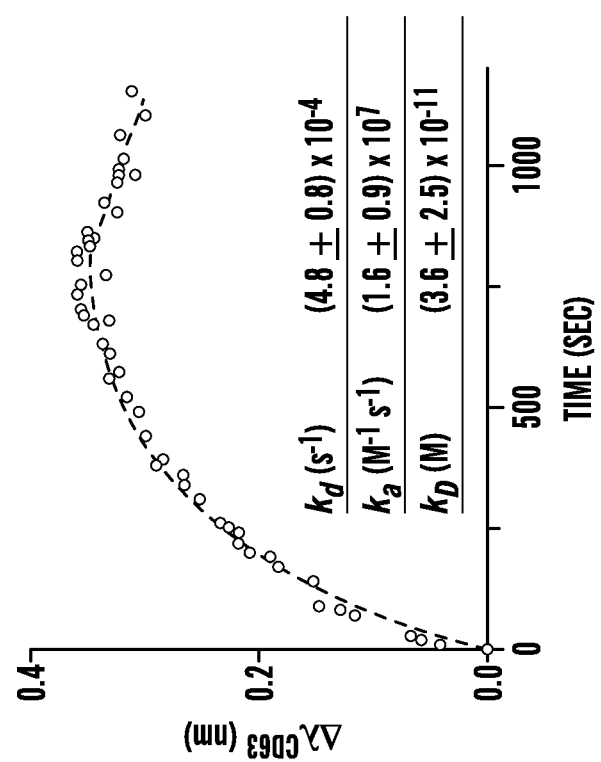
FIG. 9B
FIG. 9A

| HOLE DIAMETER (nm) | THICKNESS (nm) | PERIODICITY (nm) | SPECTRAL SHIFT (nm) | PEAK WIDTH (nm) | SENSITIVITY |
|---|---|---|---|---|---|
| 200 | 50 | 450 | 3.3 | 40 | 0.08 |
| 200 | 100 | 450 | 4.3 | 29 | 0.15 |
| 200 | 200 | 400 | 3.7 | 27 | 0.14 |
| 200 | 200 | 450 | 4.1 | 21 | 0.2 |
| 200 | 200 | 500 | 3.8 | 21 | 0.18 |
| 200 | 200 | 550 | 3.2 | 21 | 0.15 |
| 200 | 200 | 600 | 2.2 | 20 | 0.11 |

*FIG. 22D*

| CATEGORY | MARKER | CUTOFF VALUE | SENSITIVITY | SELECTIVITY | ACCURACY | AUC |
|---|---|---|---|---|---|---|
| EXOSOME COUNTS | CD63 | 0.39 | 0.75 | 0.6 | 0.7 | 0.67 |
| PROTEIN EXPRESSION PER EXOSOME | EpCAM | 0.1 | 0.9 | 1 | 0.93 | 0.968 |
| | CD24 | 0.09 | 0.8 | 1 | 0.87 | 0.9 |
| | EpCAM+ CD24 | 0.12 | 0.95 | 1 | 0.97 | 0.995 |

NANO-PLASMONIC SENSOR FOR EXOSOME DETECTION

CROSS-REFERENCE TO RELATED APPLICATION

This application is a 35 U.S.C § 371 National Phase Entry Application of International Application No. PCT/US2014/068084 filed Dec. 2, 2014, which designates the U.S., and which claims benefit under 35 U.S.C. § 119(e) of U.S. Provisional Application No. 61/910,782 filed Dec. 2, 2013, the contents of each of which are incorporated herein by reference in their entirety.

GOVERNMENT SUPPORT

This invention was made with government support under grant No. R01EB004626, R01EB010011, and R01HL113156 awarded by the National Institutes of Health (NIH), and HHSN268201000044C awarded by the National Heart, Lung, and Blood Institute (NHLBI). The government has certain rights in the invention.

TECHNICAL FIELD

The present disclosure relates generally to compositions and methods for exosome detection.

BACKGROUND

Exosomes are membrane-bound phospholipid nanovesicles (50-200 nm in diameter) actively secreted by mammalian cells (Thery, C., et al., Nat Rev Immunol 2002, 2, 569-579). They have recently received renewed interest since most cancers shed large numbers of exosomes that carry molecular information about the parent tumor (Skog, J. et al., Nat. Cell Biol. 2008, 10, 1470-1476; Simpson et al., Expert Rev Proteomics 2009, 6, 267-283). Despite the clinical potential of exosomes, developing sensitive, fast and high-throughput assays has been challenging, mainly due to the small size of the vesicles (Raimondo et al., Proteomics 2011, 11, 709-720). Isolating and purifying exosomes is time-consuming, involving either ultra-centrifugation or extensive filtering procedures (Thery et al., Curr Protoc Cell Biol Chapter 3, Unit 3.22 (2006)). Conventional downstream analyses, such as Western blotting and enyzme-linked immunosorbent assays (ELISA), require large amounts of sample and extensive post-labeling processes for detection (Simpson et al., Expert Rev Proteomics 2009, 6, 267-283; Taylor et al., Methods Mol. Biol. 2011, 728, 235-246). Given these limitations, current analytical methods are often impractical in clinical settings in which serial analyses and larger patient throughput are required.

SUMMARY

Aspects of the invention relate to the discovery that a plasmonic nanostructure designed to produce an electromagnetic field with a decay length comparable to the size of an exosome, has optical properties highly sensitive to any refractive index perturbation arising from the presence of exosomes. Accordingly, one aspect of the invention relates to a nano-plasmonic sensor for detecting exosomes. The sensor comprises a transparent planar substrate, a metal film disposed onto one surface of the substrate, wherein the metal film comprises a plurality of nanoapertures in a predefined pattern to create a sensing area that produces surface plasmon resonance upon illumination, and a capture agent attached to the metal film, wherein the capture agent specifically binds to an exosome marker.

In one embodiment of the compositions and methods described herein, the nano-plasmonic sensor further comprises a molecular spacer directly attached to the metal film, and a linking agent directly attached to the molecular spacer and directly attached to the capture agent.

In one embodiment of the compositions and methods described herein, the metal film comprises a noble metal, a transition metal, an alkali metal, or any combination thereof.

In one embodiment of the compositions and methods described herein, the substrate comprises glass, quartz, diamond, or a polymer.

In one embodiment of the compositions and methods described herein, the metal film comprises gold and the substrate comprises glass.

In one embodiment of the compositions and methods described herein, the metal film is between 50 to 500 nm thick.

In one embodiment of the compositions and methods described herein, the nano-plasmonic sensor further comprises an adhesion layer located between the metal film and the substrate surface.

In one embodiment of the compositions and methods described herein, the adhesion layer is less than about 50 nm thick.

In one embodiment of the compositions and methods described herein, the nanoapertures are arranged in a periodic pattern, and the nanoapertures have a dimension and periodicity that produce an electromagnetic field with a decay length of about 50 nm to 200 nm when the nanoapertures are illuminated by light with a wavelength close to or at the surface plasmon resonance.

In one embodiment of the compositions and methods described herein, the nanoapertures are circular, elliptical, rectangular, triangular, oval, or hexagonal.

In one embodiment of the compositions and methods described herein, the circular nanoapertures are about 50 nm to 300 nm in diameter, and wherein the periodicity is about 400 nm to 700 nm.

In one embodiment of the compositions and methods described herein, the circular nanoapertures are about 200 nm in diameter, and wherein the periodicity is about 450 nm to 500 nm.

In one embodiment of the compositions and methods described herein, the molecular spacer comprises polyethylene glycol (PEG).

In one embodiment of the compositions and methods described herein, the PEG comprises long-chain PEG and short-chain PEG in a ratio of about 1:3.

In one embodiment of the compositions and methods described herein, the linking agent comprises protein A/G or neutravidin.

In one embodiment of the compositions and methods described herein, the capture agent comprises an antibody or a portion thereof.

In one embodiment of the compositions and methods described herein, the exosome marker is an extravesicular marker or an intravesicular marker.

In one embodiment of the compositions and methods described herein, the exosome marker is present on all exosomes found in a biological sample.

In one embodiment of the compositions and methods described herein, the exosome marker is present on a subset of exosomes found in a biological sample.

In one embodiment of the compositions and methods described herein, the exosome marker is associated with a disease or disorder.

In one embodiment of the compositions and methods described herein, the disease or disorder is selected from the group consisting of cancer, cardiovascular disease, diabetes, and infection.

In one embodiment of the compositions and methods described herein, the exosome marker is selected from the group consisting of epithelial cell adhesion molecule (Ep-CAM), CD24, cancer antigen 19-9 (CA19-9), Claudin 3, cancer antigen 125 (CA-125), MUC18, epidermal growth factor receptor (EGFR), human epidermal growth factor receptor 2 (HER2), CD41, CD45, D2-40, heat shock protein 90 (HSP90), HSP70, CD63, CD44, FOLR1, EPHA2, MUC1, CD9, CD81, TSG101, LAMP1, Flotillin 1, Flotillin 2, and combinations thereof.

In one embodiment of the compositions and methods described herein, the intravesicular marker is selected from a group consisting of a protein, lipids, small molecules, mRNA, microRNA, lncRNA, and DNA.

In one embodiment of the compositions and methods described herein, the nano-plasmonic sensor further comprises at least one microfluidic channel, wherein a portion of the microfluidic channel is disposed on the sensing area.

In one embodiment of the compositions and methods described herein, the nano-plasmonic sensor further comprises a plurality of microfluidic channels, wherein each channel comprises a capture agent that specifically binds to a different exosome marker.

The nano-plasmonic sensor described herein can further be incorporated into a platform for highly sensitive, label-free, and high-throughput exosome detection and marker expression level analysis. Another aspect of the invention relates to an imaging system. The imaging system comprises a light source, a detector, and the nano-plasmonic sensor provided herein, wherein light produced by the light source can transmit through the nano-plasmonic sensor, and then be detected by the detector. In one embodiment of the compositions and methods described herein, the imaging system is portable.

In one embodiment of the compositions and methods described herein, the imaging system further comprises a conditioning element for conditioning the light produced by the light source.

In one embodiment of the compositions and methods described herein, the conditioning element comprises a diffuser, a lens, a filter, or any combination thereof.

In one embodiment of the compositions and methods described herein, the light source comprises a laser or light emitting diode (LED).

In one embodiment of the compositions and methods described herein, the light source is a broadband source and the imaging system comprises a filter (e.g., a bandpass filter) to select a wavelength from the broadband source.

In one embodiment of the compositions and methods described herein, the detector is an active-pixel sensor (APS), a charge-coupled device (CCD), a photodiode, or a photomultiplier.

In one embodiment of the compositions and methods described herein, the detector is a complementary metal-oxide-semiconductor (CMOS) sensor.

In one embodiment of the compositions and methods described herein, the detector is a monochromatic or color charge-coupled device (CCD).

The nano-plasmonic sensor alone, or together with the imaging system can be applied to detect exosomes in a sample. Another aspect of the invention relates to a method of detecting exosomes in a sample. The method comprises introducing a sample suspected of containing one or more exosomes onto a nano-plasmonic sensor described herein under conditions which promote binding of the exosomes to the sensor, washing the sensor to remove unbound materials, illuminating the sensor to thereby transmit light through the sensor, measuring the light transmitted through the sensor to identify a significant change from that of a negative control, and detecting exosomes in the sample when the significant change in the transmitted light is identified.

In one embodiment of the compositions and methods described herein, the negative control is a solution substantially free of exosomes or exosome lysates.

In one embodiment of the compositions and methods described herein, the nano-plasmonic sensor is part of an imaging system described herein.

In one embodiment of the compositions and methods described herein, the difference being identified is a shift in peak wavelength.

In one embodiment of the compositions and methods described herein, the difference being identified is an intensity change at a fixed wavelength.

In one embodiment of the compositions and methods described herein, the method further comprises a step of contacting the exosomes bound to the sensor with a secondary label comprising an agent that specifically binds to an exosome marker.

In one embodiment of the compositions and methods described herein, the secondary label comprises a metallic nanoparticle, a magnetic nanoparticle, a dielectric nanoparticle, a semiconductor nanoparticle, or a diamond nanoparticle.

In one embodiment of the compositions and methods described herein, the metallic nanoparticle is a gold sphere or a gold star.

Another aspect of the invention relates to a method for determining the expression level of a target marker in a sample of exosomes. The method comprises detecting total exosomes in the sample by the method of exosome detection described herein, using a capture agent that specifically binds a pan-exosomal marker, detecting exosomes in the sample expressing the target marker by the method of exosome detection described herein using a capture agent that specifically binds the target marker, and calculating the ratio of exosomes with target marker to total exosomes to thereby indicate the average expression level of the target marker per exosome from the sample.

In one embodiment of the compositions and methods described herein, the pan-exosomal marker is CD63.

In one embodiment of the compositions and methods described herein, the target marker is a cancer marker.

Another aspect of the invention relates to a method of detecting a disease or disorder in a subject, comprising detecting an expression level of a marker of the disease or disorder using the compositions and methods described herein for determining the expression level, comparing the expression level detected in the previous step to that of a normal, healthy control, and detecting the disease or disorder in the subject when an elevated exosomal expression level of the marker of the disease or disorder is identified.

Another aspect of the invention relates to a method of monitoring treatment efficacy of a disease or disorder, comprising periodically determining an expression level of a target marker associated with the disease or disorder in a sample of exosomes using the compositions and methods described herein for determining the expression level, wherein a reduction in the expression level over time indicates treatment efficacy.

In one embodiment of the compositions and methods described herein, the disease or disorder is cancer.

In one embodiment of the compositions and methods described herein, the cancer is ovarian cancer and the marker is of the cancer is selected from the group consisting of EpCAM, CD24, CA19-9, Claudin3, CA-125, MUC18, EGFR, and combinations thereof.

Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are useful to an embodiment, yet open to the inclusion of unspecified elements, whether useful or not.

The singular terms "a," "an," and "the" include plural referents unless context clearly indicates otherwise. Similarly, the word "or" is intended to include "and" unless the context clearly indicates otherwise. The abbreviation, "e.g." is derived from the Latin exempli gratia, and is used herein to indicate a non-limiting example. Thus, the abbreviation "e.g." is synonymous with the term "for example."

The terms "nanostructure" refers to any structure or device comprising a combination or association or plurality of one or more "nanoapertures," as the term is used herein.

A "nanoaperture" is used herein to refer to an opening or aperture in a plasmonic material, such as a metal film. As used herein, nanoapertures include symmetric circular holes, spatially anistropic shapes, e.g., elliptical shapes, slits, and also include any aperture of a triangular, square, rectangular, or polygonal shape. In one embodiment, a combination of different shaped nanoapertures can be used. In addition, nanoapertures can be "through nanoapertures" that penetrate through a material, such as a metal film, or "non-through nanoapertures" that penetrate a part of a material without completely penetrating through the material or substrate. Preferably, a nanoaperture has a dimension of about 1500 nm or less, about 1400 nm or less, about 1300 nm or less, about 1200 nm or less, about 1100 nm or less, about 1000 nm or less, about 900 nm or less, about 800 nm or less, about 700 nm or less, about 600 nm or less, about 500 nm or less, about 450 nm or less, about 400 nm or less, about 350 nm or less about 300 nm or less, about 250 nm or less, about 240 nm or less, about 230 nm or less, about 220 nm or less, about 210 nm or less, about 200 nm or less, about 190 nm or less, about 180 nm or less, about 170 nm or less, about 160 nm or less, about 150 nm or less, about 140 nm or less, about 130 nm or less, about 120 nm or less, about 110 nm or less, about 100 nm or less, about 90 nm or less, about 80 nm or less, about 70 nm or less, about 60 nm or less, about 50 nm or less, about 40 nm or less, about 30 nm or less, about 20 nm or less, or about 10 nm or less.

The term "predefined" as used with respect to "predefined pattern" refers to a pattern that is designed and selected to be used for the pattern of nanoapertures in a nanostructure. The pattern design can be selected so the nanoapertures function in the pattern for collective excitation of plasmons and plasmon resonance.

The term "predefined" as used with respect to a "predefined shape" refers to a shape of a nanoaperture that was determined and selected to be used for the shape of the void of the nanoapertures of a nanostructure.

The term "periodicity," as used herein, refers to a recurrence or repetition of nanoapertures on or within a nanostructure at regular intervals by their positioning on the nanostructure. The term "periodic" as used herein therefore refers to the regular predefined pattern of nanoapertures with respect to each other.

The term "non-periodic," as used herein, refers to a pattern of nanoapertures which are in a pattern, which is not a periodic pattern, or is not a lattice or other repeating unit configuration. A random distribution of nanoapertures is a non-periodic pattern.

The term "unit cell" refers to a collection of nanoapertures in a predefined pattern, where an organized arrangement of a number of unit cells forms a "lattice." Each nanoaperture of a unit cell that belongs to one or more other unit cells in the lattice is referred to as a unit mode.

The term "lattice," as used herein, refers to a repeating or reoccurring pattern of a unit or unit cell, where the unit cell can comprise one or more nanoapertures. Typically, a unit cell comprising one or more nanoapertures has the nanoapertures in an organized predefined pattern with respect to each other. In one embodiment, the term "lattice" as referred to herein refers to the order or the type of partially ordered set. In one embodiment the lattice can be a discrete subgroup, which refers to a discrete subgroup of a topological group of nanoapertures with finite covolume. In one embodiment, the lattice is a group lattice, which refers to a repeating arrangement of nanoapertures.

"Surface plasmon resonance," as used herein, refers to the physical phenomenon in which incident light stimulates collective electron oscillations at the metal surface for planar surfaces. The term "localized surface plasmon resonance (LSPR)" refers to surface plasmon resonance of nanometer-sized structures, such as a metallic nanoparticle. The oscillating electrons produce strong electromagnetic fields in the (non-conducting) ambient medium near the surface of the metal.

As used herein, "surface plasmons," "surface plasmon polaritons," or "plasmons" refer to the collective oscillations of free electrons at plasmonic surfaces, such as metals. These oscillations result in self-sustaining, surface electromagnetic waves that propagate in a direction parallel to the metal/dielectric (or metal/vacuum) interface. Since the wave is on the boundary of the metal and the external medium (air or water for example), these oscillations are very sensitive to any refractive index change of this boundary, such as, for example, the adsorption of a biomolecular target to the metal surface. Additionally, the electromagnetic field strength decays exponentially from the metal surface to the surrounding environment (e.g., vacuum or dielectric). A maximum value of the electromagnetic field strength can be found at the metal/dielectric or metal/vacuum interface.

As used herein, "decay length" is defined as the length or distance away from the metal surface at which the electromagnetic field strength reduces to 1/e of the maximum value. The electromagnetic field energy is substantially confined within a volume defined by the decay length.

As used herein, a "plasmonic material" refers to a material that exhibits surface plasmon resonance when excited with electromagnetic energy, such as light waves, even though the wavelength of the light is much larger than the size of the material. In one embodiment of the aspects described herein, plasmonic materials refer to metallic plasmonic materials. Such metallic plasmonic materials can be any metal, including noble metals, alkali metals, transition metals, and alloys. Examples of plasmonic materials include, but are not limited to, gold, rhodium, palladium, silver, platinum, osmium, iridium, titanium, aluminum, copper, lithium, sodium, potassium, nickel, a metallic alloy, indium tin oxide, aluminum zinc oxide, gallium zinc oxide, titanium nitride, and graphene. A plasmonic material can be "optically observable" when it exhibits significant scattering intensity in the optical region (ultraviolet-visible-infrared spectra), which includes wavelengths from approximately 100 nanometers (nm) to 3000 nm. A plasmonic material can be "visually observable" when it exhibits significant scattering intensity in the wavelength band from approximately 380 nm to 750 nm, which is detectable by the human eye, i.e., the visible spectrum.

As used herein, the term "plasmonic nanostructure" refers to any independent nanostructure, device, or system exhibiting surface plasmon resonance or localized surface plasmon resonance properties due to the presence, combination, or association of one or more plasmonic nanoapertures. For example, an array of nanoapertures is a plasmonic nanostructure. The nanoapertures can be arranged in any pattern that gives rise to a desired optical property for the nanostructure, such as periodic pattern or a non-periodic pattern, including pseudo-random and random patterns. One form of a plasmonic nanostructure is a nano-plasmonic sensor described herein.

As used herein, the term "sensing area" refers to an area in a plasmonic nanostructure (e.g., a nano-plasmonic sensor as described herein) that includes a plurality of nanoapertures in a predefined pattern. Upon illumination by light having an appropriate wavelength or wavelength range, the nanoapertures can act in a concerted manner to generate surface plasmon resonance. A plasmonic nanostructure can have 1, 2, 3, 4, 5, 6, 7, 8, 9, 10, or more sensing areas. Each sensing area can contain the same or different capture agents.

As used herein, the term "resist" refers to both a thin layer used to transfer an image or pattern, such as a nanoaperture pattern, to a substrate which it is deposited upon. A resist can be patterned via lithography to form a (sub)micrometer-scale, temporary mask that protects selected areas of the underlying substrate during subsequent processing steps, typically etching. The material used to prepare the thin layer (typically a viscous solution) is also encompassed by the term resist. Resists are generally mixtures of a polymer or its precursor and other small molecules (e.g., photoacid generators) that have been specially formulated for a given lithography technology. Resists used during photolithography, for example, are called "photoresists." Resists used during electron-beam lithography are called "ebeam resists."

As used herein, the terms "sample," means any sample comprising or being tested for the presence of one or more nanovesicles (e.g., exosomes). Such samples include, without limitation, samples derived from or containing cells, organisms (bacteria, viruses), lysed cells or organisms, cellular extracts, nuclear extracts, components of cells or organisms, extracellular fluid, media in which cells or organisms are cultured in vitro, blood, plasma, serum, gastrointestinal secretions, ascites, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, pleural fluid, nipple aspirates, breast milk, external sections of the skin, respiratory, intestinal, and genitourinary tracts, and prostatic fluid. A sample can be a viral or bacterial sample, a sample obtained from an environmental source, such as a body of polluted water, an air sample, or a soil sample, as well as a food industry sample. A sample can be a biological sample which refers to the fact that it is derived or obtained from a living organism. The organism can be in vivo (e.g. a whole organism) or can be in vitro (e.g., cells or organs grown in culture). In one embodiment, a "biological sample" also refers to a cell or population of cells or a quantity of tissue or fluid from a subject. Most often, a sample has been removed from a subject, but the term "biological sample" can also refer to cells or tissue analyzed in vivo, i.e., without removal from the subject. Often, a "biological sample" will contain cells from a subject, but the term can also refer to non-cellular biological material, such as non-cellular fractions of blood, saliva, or urine. In one embodiment, a biological sample is from a resection, bronchoscopic biopsy, or core needle biopsy of a primary, secondary or metastatic tumor, or a cellblock from pleural fluid. In addition, fine needle aspirate biological samples are also useful. In one embodiment, a biological sample is primary ascite cells. Biological samples also include explants and primary and/or transformed cell cultures derived from patient tissues. A biological sample can be provided by removing a sample of cells from subject, but can also be accomplished by using previously isolated cells or cellular extracts (e.g., isolated by another person, at another time, and/or for another purpose). Archival tissues, such as those having treatment or outcome history may also be used. Biological samples include, but are not limited to, tissue biopsies, scrapes (e.g. buccal scrapes), whole blood, plasma, serum, urine, saliva, cell culture, or cerebrospinal fluid. The samples analyzed by the compositions and methods described herein may have been processed for purification or enrichment of exosomes contained therein.

As used herein, a "nanovesicle" refers to a naturally occurring or synthetic vesicle that includes a cavity inside. The nanovesicle comprises a lipid bilayer membrane enclosing contents of an internal cavity. A nanovesicle can include, but is not limited to, a liposome, an exosome, a vacuole, a lysosome, a transport vesicle, a secretory vesicle, a gas vesicle, a matrix vesicle, or a multivesicular body. A nanovesicle has a dimension of about 1000 nm or less, about 900 nm or less, about 800 nm or less, about 700 nm or less, about 600 nm or less, about 500 nm or less, about 450 nm or less, about 400 nm or less, about 350 nm or less about 300 nm or less, about 250 nm or less, about 240 nm or less, about 230 nm or less, about 220 nm or less, about 210 nm or less, about 200 nm or less, about 190 nm or less, about 180 nm or less, about 170 nm or less, about 160 nm or less, about 150 nm or less, about 140 nm or less, about 130 nm or less, about 120 nm or less, about 110 nm or less, about 100 nm or less, about 90 nm or less, about 80 nm or less, about 70 nm or less, about 60 nm or less, about 50 nm or less, about 40 nm or less, about 30 nm or less, about 20 nm or less, or about 10 nm or less.

Exosomes are a type of nanovesicle, also referred to in the art as microvesicles. Microvesicles are shed by eukaryotic cells, or budded off of the plasma membrane, to the exterior of the cell. These membrane vesicles are heterogeneous in size with diameters ranging from about 10 nm to about 5000 nm. The small microvesicles (approximately 10 to 1000 nm, preferably 30 to 100 nm in diameter) that are released by exocytosis of intracellular multivesicular bodies are referred to in the art as "exosomes". The methods and compositions described herein are equally applicable for microvesicles of all sizes.

In some of the literature, the term "exosome" also refers to protein complexes containing exoribonucleases which are involved in mRNA degradation and the processing of small nucleolar RNAs (snoRNAs), small nuclear RNAs (snRNAs) and ribosomal RNAs (rRNA) (Liu et al., 2006b; van Dijk et al., 2007). Such protein complexes do not have membranes and are not "microvesicles" or "exosomes" as those terms are used here in.

As used herein, the term "patient" and "subject" are used interchangeably to refer to a human or animal. Usually the animal is a vertebrate such as a mammal. Examples of mammals include, without limitation, primates, rodents, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. A subject can be male or female. Additionally, a subject can be any stage of development, e.g., embryo, fetus, infant, child, pre-adolescent, adolescent, young adult, mature adult, and elderly adult. The female subject can be pregnant or not.

In one embodiment the subject is a mammal. The mammal can be a human, non-human primate, mouse, rat, dog, cat, horse, or cow, but are not limited to these examples. Mammals other than humans can be advantageously used as subjects that represent animal models of disorders associated with autoimmune disease or inflammation. In addition, the methods and compositions described herein can be used for domesticated animals and/or pets. A human subject can be of any age, gender, race or ethnic group, e.g., Caucasian (white), Asian, African, African American, African European, Hispanic, Mideastern, etc. In one embodiment, the subject can be a patient or other subject in a clinical setting. The subject can be suspected of, or at risk for, having or developing a disease or disorder, or may have already been diagnosed as having a disease or disorder. The subject may be undergoing treatment.

As used herein, a "capture agent" refers to any agent having specific binding for a nanovesicle (e.g., an exosome). Binding may be to a marker that is present on all exosomes, or to a subset of exosomes. Typically the capture agent specifically binds a marker fully or partially present on the external surface of the nanovesicle (referred herein as an extravesicular marker), although in one embodiment, the capture agent specifically binds a marker that is present on the interior of the nanovesicle (referred herein as an intravesicular marker). The capture agent is immobilized on the surface of a plasmonic nanostructure that is contacted to the sample (e.g., the sensing area). Examples of capture agents include, without limitation, a nucleic acid, oligonucleotide, peptide, polypeptide, antigen, polyclonal antibody, monoclonal antibody, single chain antibody (scFv), an antibody portion, F(ab) fragment, F(ab')$_2$ fragment, Fv fragment, small organic molecule, polymer, compounds from a combinatorial chemical library, inorganic molecule, or any combination thereof.

A "nucleic acid", as described herein, can be RNA or DNA, and can be single or double stranded, and can be, for example, a nucleic acid encoding a protein of interest, a polynucleotide, an oligonucleotide, a nucleic acid analogue, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example, but not limited to, RNAi, shRNAi, siRNA, micro RNAi (mRNAi), antisense oligonucleotides etc.

As used herein, the term DNA is defined as deoxyribonucleic acid. The term "polynucleotide" is used herein interchangeably with "nucleic acid" to indicate a polymer of nucleosides. Typically a polynucleotide of this invention is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. As used herein, a polynucleotide is understood to include both DNA, RNA, and in each case both single- and double-stranded forms (and complements of each single-stranded molecule). "Polynucleotide sequence" as used herein can refer to the polynucleotide material itself and/or to the sequence information (i.e., the succession of letters used as abbreviations for bases) that biochemically characterizes a specific nucleic acid. A polynucleotide sequence presented herein is presented in a 5' to 3' direction unless otherwise indicated.

The term "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a nonpolypeptide moiety covalently or noncovalently associated therewith is still considered a "polypeptide." Exemplary modifications include glycosylation and palmitoylation. Polypeptides may be purified from natural sources, produced using recombinant DNA technology, synthesized through chemical means such as conventional solid phase peptide synthesis, etc. The terms "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

"Antigen" is defined herein as a substance inducing an immune response. The antigenic determinant group is termed an epitope, and the epitope in the context of a carrier molecule (that can optionally be part of the same molecule, for example, botulism neurotoxin A, a single molecule, has three different epitopes. See Mullaney et al., Infect Immun October 2001; 69(10): 6511-4) makes the carrier molecule active as an antigen. Usually antigens are foreign to the animal in which they produce immune reactions.

As used herein, "antibodies" can include polyclonal and monoclonal antibodies and antigen-binding derivatives, or portions or fragments thereof. Well-known antigen binding fragments include, for example, single domain antibodies (dAbs; which consist essentially of single VL or VH antibody domains), Fv fragment, including single chain Fv fragment (scFv), Fab fragment, and F(ab')$_2$ fragment. Methods for the construction of such antibody molecules are well known in the art. As used herein, the term "antibody" refers to an intact immunoglobulin or to a monoclonal or polyclonal antigen-binding fragment with the Fc (crystallizable fragment) region or FcRn binding fragment of the Fc region. Antigen-binding fragments can be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The terms Fab, Fc, pFc', F(ab') 2 and Fv are employed with standard immunological meanings [Klein, Immunology (John Wiley, New York, N.Y., 1982); Clark, W. R. (1986) The Experimental Foundations of Modern Immunology (Wiley & Sons, Inc., New York); Roitt, I. (1991) Essential Immunology, 7th Ed., (Blackwell Scientific Publications, Oxford)].

"Polyclonal antibody" is defined herein as an antibody produced by several clones of B-lymphocytes as would be the case in a whole animal, and usually refers to antibodies raised in immunized animals. "Monoclonal antibody" is defined herein as a cell line, whether within the body or in culture, that has a single clonal origin. Monoclonal antibodies are produced by a single clone of hybridoma cells, and are therefore a single species of antibody molecule. "Single chain antibody (Scfv)" is defined herein as a recombinant fusion protein wherein the two antigen binding regions of the light and heavy chains (Vh and Vl) are connected by a linking peptide, which enables the equal expression of both the light and heavy chains in a heterologous organism and stabilizes the protein. "F(Ab) fragment" is defined herein as fragments of immunoglobulin prepared by papain treatment. Fab fragments consist of one light chain linked through a disulphide bond to a portion of the heavy chain, and contain one antigen binding site. They can be considered as univalent antibodies. "F(Ab')$_2$ Fragment" is defined herein as the approximately 90 kDa protein fragment obtained upon pepsin hydrolysis of an immunoglobulin molecule N-terminal to the site of the pepsin attack. Contains both Fab fragments held together by disulfide bonds in a short section of the Fe fragment. "Fv Fragment" is defined herein as the N-terminal portion of a Fab fragment of an immunoglobulin molecule, consisting of the variable portions of one light chain and one heavy chain.

The terms "label", as used herein, refer to a composition capable of producing or enhancing a detectable signal indicative of the presence of the target in a sample.

As used herein, the term "marker" refers to a molecule that is associated with a nanovesicle, and can bind to a capture agent for detecting the nanovesicle. A marker can be any components of a nanovesicle that can be recognized by a capture agent. Examples of markers include, without limitation, protein or a nucleic acid or a component of the lipid bilayer that makes up the membrane of the nanovesicle. Useful markers include receptors (e.g., extracellular) and channel components. A marker can be either an extravesicular or intravesicular marker. An "extravesicular marker" is defined herein as a marker that is either partially or fully present on the surface of a nanovesicle. An "intravesicular marker" is defined herein as a marker that is inside the cavity of a nanovesicle. A marker can be present on all nanovesicles in a sample, or on a subset of nanovesicles in a sample. A marker that is common to all nanovesicles is referred to herein as a pan-exosomal marker.

A "molecular spacer" is defined herein as a molecule that is directly attached to the metal film surface of a plasmonic nanostructure (e.g., a nano-plasmonic sensor). Examples of molecular spacers include, without limitation, nucleic acid, oligonucleotide, peptide, polypeptide, antigen, polyclonal antibody, monoclonal antibody, single chain antibody (scFv), an antibody portion, F(ab) fragment, F(ab')$_2$ fragment, Fv fragment, small organic molecule, polymer, compounds from a combinatorial chemical library, inorganic molecule, or any combination thereof.

A "linking agent" is defined herein as a molecule that is directly attached to a molecular spacer, and is also directly attached to a capture agent. Stated another way, a linking agent physically links a molecular spacer and a capture agent together. In one embodiment, the linking agent is a first member of a specific binding pair. In such an embodiment, the capture agents may be comprised of the second member of the specific binding pair. Examples of such specific binding pairs include, without limitation, antigens, antibodies, haptens, oligonucleotides, polynucleotides, avidin, streptavidin, hormones, receptors, lectins, carbohydrates, IgG, protein A, and nucleic acid binding proteins. A linking agent can include, but is not limited to, a nucleic acid, oligonucleotide, peptide, polypeptide, antigen, polyclonal antibody, monoclonal antibody, single chain antibody (scFv), an antibody portion, F(ab) fragment, F(ab')$_2$ fragment, Fv fragment, small organic molecule, polymer, compounds from a combinatorial chemical library, inorganic molecule, or any combination thereof.

As the term is used herein, "specific binding pair" refers to two substances which exhibit a mutual and specific binding affinity. Examples include antigen-antibody, hapten-antibody or antibody-antibody pairs, complementary oligonucleotides or polynucleotides, avidin-biotin, streptavidin-biotin, hormone-receptor, ligand-receptors, lectin-carbohydrate, IgG-protein A, nucleic acid-nucleic acid binding protein, and nucleic acid-anti-nucleic acid antibody.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized. In certain embodiments, specific binding is indicated by a dissociation constant on the order of $\leq 10^{-8}$ M, $\leq 10^{-9}$ M, $\leq 10^{-10}$ M or below.

Polyethylene glycol (PEG) is referred to herein as a component of the nano-plasmonic sensor and is used as a molecular spacer. A variety of forms, and combinations of PEG are envisioned for use as such spacers. Polyethylene glycol (PEG) is a polyether compound with many applications from industrial manufacturing to medicine. The structure of PEG is (note the repeated element in parentheses): H—(O—CH2-CH2)n-OH. PEG is also known as polyethylene oxide (PEO) or polyoxyethylene (POE), depending on its molecular weight. PEG, PEO, or POE refers to an oligomer or polymer of ethylene oxide. The three names are chemically synonymous, but historically PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. PEGs are prepared by polymerization of ethylene oxide and are commercially available over a wide range of molecular weights from 300 g/mol to 10,000,000 g/mol. While PEG and PEO with different molecular weights find use in different applications, and have different physical properties (e.g. viscosity) due to chain length effects, their chemical properties are nearly identical. Different forms of PEG are also available, depending on the initiator used for the polymerization process—the most common initiator is a monofunctional methyl ether PEG, or methoxypoly(ethylene glycol), abbreviated mPEG. Lower-molecular-weight PEGs are also available as purer oligomers, referred to as monodisperse, uniform, or discrete. Very high purity PEG has recently been shown to be crystalline, allowing determination of a crystal structure by x-ray diffraction. Since purification and separation of pure oligomers is difficult, the price for this type of quality is often 10-1000 fold that of polydisperse PEG. Branched PEGs have three to ten PEG chains emanating from a central core group. Star PEGs have 10 to 100 PEG chains emanating from a central core group. Comb PEGs have multiple PEG chains normally grafted onto a polymer backbone.

A "long-chain polyethylene glycol (PEG)" or "long PEG" is defined herein as a PEG polymer having a molecular weight equal to or higher than 750 Da.

A "short-chain PEG" or "short PEG" is defined herein as a PEG polymer having a molecular weight equal to or less than 500 Da.

As used herein, "expression level" refers to the number of mRNA molecules and/or polypeptide molecules encoded by a given gene that are present in a cell or sample.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

BRIEF DESCRIPTION OF THE DRAWINGS

FIG. 1A is a schematic illustrating that cancer cells secrete a large abundance of exosomes through fusion of the multivesicular body (MVB) with cellular plasma membrane. These nanovesicles carry parental proteins in the same topological orientation. High magnification transmission electron micrograph (inset) indicates typical exosomes have a diameter ~100 nm. FIG. 1B is an image of Finite-difference time-domain (FDTD) simulation indicating that the enhanced electromagnetic fields are tightly confined near a periodic nanoaperture surface. The field distribution overlaps with the size of exosomes captured onto the sensing surface, maximizing exosome detection sensitivity. FIG. 1C is a scanning electron micrograph (SEM) of the periodic nanoapertures in the nPLEX sensor. The hole diameter is 200 nm with the periodicity of 450 nm. The structure was patterned in a gold film (200 nm think) deposited on a glass substrate. FIG. 1D is an image of a prototype miniaturized nPLEX imaging system developed for multiplexed and high-throughput analyses of clinical exosomes. The system uses a complementary-metal-oxide-semiconductor (CMOS) imager to record the transmitted light intensity from a nPLEX sensor. FIG. 1E is a representative schematic and changes in transmission spectra indicating exosome detection with the sensor. The gold surface is pre-functionalized by a layer of polyethylene glycol (PEG), and antibody conjugation and specific exosome binding were monitored by transmission spectral shifts as measured by the sensor (not drawn to scale). FIG. 1F is an SEM indicating specific exosome capture by surface-functionalized sensor.

FIG. 2A is an image of CaOV3 ovarian cancer cells shed nanoscale vesicles as imaged by a scanning electron microscope (SEM). FIG. 2B is a graph of experimental results indicating the size distribution of exosomes, characterized by the nanoparticle tracking analysis. The mean diameter of exosomes was ~100 nm, which agreed with the SEM observation (inset).

FIG. 3A is a set of images indicating the electric field intensity of the sensor in simulation. The decay length of the intensity increases with longer periodicity. FIG. 3B is a graph of simulated results indicating the shift ($\Delta\lambda$) and the width (w) of surface plasmon resonance (SPR) spectrum when exosomes (100 nm in diameter) are bound to the nanoaperture surface. The sensor of 450 nm periodicity was found optimal, as it produces the largest spectral shift ($\Delta\lambda$) with the smallest peak spread (w). FIG. 3C is a graph of simulated results indicating that the sensitivity of the sensor, defined as $\Delta\lambda$/w, also has the maximal value with the 450-nm sensor.

FIG. 4A-FIG. 4C are an illustration and images of a device configuration of a nPLEX sensor integrated with microfluidics. A 12-channel fluidic cell (FIG. 4A) was placed on top of a glass slide containing nanoaperture arrays (FIG. 4B). A total of 36 measurement sites were arranged into a 12×3 array format (FIG. 4C) with each fluidic channel encompassing three measurement sites. Surface functionalization, sample injection, and washing steps were performed through the fluidic system.

FIG. 5A is a diagram of a spectrometer setup constructed on a conventional upright microscope. A tungsten white light source illuminated the sensor through a microscope objective, and the transmitted light was collected by an optical fiber placed underneath the sensor. The collected light was then analyzed by a miniaturized spectrometer. FIG. 5B is a diagram of the portable imaging setup consisted of a light source (a laser diode) and a CMOS imager. The sensor was located on top of the imager and the transmitted light intensities through the nanoaperture arrays were recorded by the imager. FIG. 5C is a graph of experimental results that indicate exosome binding increases the refractive index on the sensor surface, which induces a spectral shift to a longer wavelength. This increase of refractive index also causes intensity changes at a fixed laser wavelength. Exosome binding, therefore, can be detected by tracking spectral shifts in the spectrometry setup or by measuring the intensity changes in the portable imaging setup. FIG. 5D is a graph of experimental results that indicate both spectral shifts and intensity changes showed linear responses to the refractive index.

FIG. 6A-FIG. 6B are experimental results of surface chemistry optimization on nPLEX sensors. FIG. 6A is a graph of experimental results indicating that biotinylated, fluorescent polystyrene beads (diameter, 100 nm) were captured on streptavidin-coated sensor surface. These sensors were functionalized with mixtures of long (MW, 1 kDa) and short (MW, 200 Da) polyethylene glycol (PEG) polymers. Streptavidin was conjugated on long PEGs. Following the bead capture, the fluorescence intensity of a streptavidin-coated sensor was normalized against that of a control sensor (without streptavidin functionalization). The 1:3 mixture of long and short PEGs demonstrated the best capture yield. FIG. 6B is a set of electron micrographs of sensor surfaces PEGylated with 1/1 and 1/3 mixture of long and short PEGs. More beads were captured when the ratio was 1/3, supporting the fluorescent data in FIG. 6A.

FIG. 7C is a table summarizing spectral shifts in both sensors.

FIG. 9A-FIG. 9D are graphs and micrographs of experimental data that demonstrate exosome quantification and protein profiling with an nPLEX sensor. FIG. 9A is a graph of real-time kinetic sensorgram for exosome capture. Exosomes isolated from human ovarian cancer cell line (CaOV3) were introduced onto the sensor functionalized with CD63 antibody for exosomal capture. The capture was highly efficient (kD ~36 pM) from multi-valency binding. FIG. 9B is a graph of experimental results that demonstrates comparison of exosome detection sensitivity. The sensor showed considerably higher sensitivity as compared to ELISA and western blotting (WB). The nano-plasmonic sensor detection limit was determined by titrating a known quantity of exosomes and measuring their associated CD63 signal. ELISA and WB detection thresholds were independently characterized with CD63 chemiluminescence. FIG. 9C is a set of images and graphs of experimental results that demonstrates signal amplification through secondary labeling. Exosomes captured on the sensor were further targeted with CD63-specific Au nanospheres (arrow) or star-shaped particles to enhance spectral shifts. Scale bar, 50 nm. FIG. 9D is a graph of experimental results that demonstrates correlation between nPLEX and ELISA measurements. Exosomes isolated from human ovarian cancer cell lines (CaOV3 and OV90) were used. The expression level ($\xi$) was determined by normalizing the marker signal with that of CD63, which accounted for variation in exosomal counts across samples. All measurements in FIG. 9B-FIG. 9D were in performed in triplicate and the data is displayed as mean±s.d.

FIG. 10A) and star-shaped Au nanoparticles (mean diameter, 50 nm; FIG. 10B) were used as a secondary labeling agent for signal amplification.

FIG. 13C is a set of images that shows the analysis of the vesicular composition of the filtrate. Aliquots of CaOV3 cell culture supernatant were processed via 1) conventional gradient ultracentrifugation to enrich for pure exosomes; 2) centrifugal concentration without filtration; and 3) centrifugal concentration after 0.2 μm filtration to remove large debris. Lysates from three samples were quantified and equal protein amounts were immunoblotted for exosomal markers (HSP90, HSP70, Flotillin 1, Flotillin 2, CD9 and CD63) as well as other vesicular markers (Integrin β1, Integrin α5). The results indicated that filtration can effectively remove other large vesicular debris, while retaining exosomal population for the nPLEX assay.

FIG. 14A is a photograph of nPLEX chip integrated with a multi-channel microfluidic cell for independent and parallel analyses. (Right) Transmission intensities of 12×3 nanoaperture arrays were measured simultaneously using the imaging setup. FIG. 14B are experimental data demonstrating the evaluation of Ascites exosomes from ovarian cancer and non-cancer patients by the nPLEX sensor. Cancer exosomes were captured on EpCAM and CD24-specific sensor sites, which led to intensity changes in the transmitted light. FIG.

14C is a set of graphs of experimental results that indicates exosomal expression levels of EpCAM and CD24 in ascites samples from patients (n=30) measured by nPLEX. Ovarian cancer patients (n=20) were associated with elevated EpCAM and CD24 expression, while non-cancer patients (n=10) showed negligible signals. By combing the expression profiles of EpCAM and CD24, a high diagnostic accuracy (96%) was achieved. FIG. 14D is a graph of experimental results that demonstrates longitudinal monitoring of treatment responses. Ascites samples were collected sequentially from ovarian cancer patients undergoing chemotherapy (n=8) and profiled directly by the nPLEX platform. Measuring temporal changes in exosomal expressions of EpCAM and CD24 could distinguish treatment response.

FIG. 17C demonstrates that three different types of fluorescent antibodies can be printed on a glass substrate, using the developed template. Each spot size is 250 μm×250 μm.

FIG. 21A is an image of a second generation nPLEX chip. By applying light interference lithography, the entire 4-inch wafer was patterned with nanoholes. The sensing area was defined by anisotropic backside etching of the Si wafer. FIG. 21B is a magnified view of an area in FIG. 21A showing that the nPLEX chip has 1,089 (33×33) measurement sites for massively parallel detection. FIG. 21C is a set of magnified views of the nanohole lattice. Each measurement site has a 200×200 nanohole lattice. The hole diameter is 200 nm, and the periodicity is 450 nm. FIG. 21D is a transmission spectrum, measured from 33 diagonal sites (inset), closely matched one another. This result confirmed that highly uniform nanohole arrays were patterned across the wafer. a.u., arbitrary unit.

FIG. 22A-FIG. 22D are graphs of simulated results that demonstrate sensitivity optimization of the nPLEX system using simulations. FIG. 22A is a set of images of the electric field intensity of the simulated nPLEX sensor. The decay length of the intensity increases with longer periodicity. FIG. 22B is a graph of simulated results indicating that detection sensitivity of the sensor for 100 nm exosomes, defined as $\Delta\lambda/w$, has the maximal value with the 450-nm nPLEX sensor. a.u., arbitrary unit. FIG. 22C is a graph of simulated results indicating that for 200 nm hole diameter and 450 nm periodicity, the sensitivity maximized at 200 nm Au film thickness. a.u., arbitrary unit. FIG. 22D is a table summarizing simulation data for nanohole design. The optimal dimension for the highest sensitivity is highlighted.

FIG. 23A is a graph of simulated results demonstrating that the nPLEX signal (measured by a spectral shift of resonance peak) can be amplified by labeling target markers with nanobeads. The graph demonstrates the simulated spectra when polystyrene nanobeads of different diameters are used for the signal amplification. Along the dashed line, the curves represent 0 nm, 20 nm, 40 nm, 60 nm, 80 nm, 100 nm, 120 nm, 140 nm, 160 nm, 180 nm, and 200 nm, respectively. FIG. 23B is a graph of simulated results demonstrating that the nPLEX signal (a spectral shift) produced by the nanobeads increases with the bead size. FIG. 23C is a graph of simulated results demonstrating that in terms of spectral shift per sensing area, the 180 nm nanobeads show the largest signal amplification.

FIG. 25A is a graph of experimental results of receiver operation characteristic (ROC) curves generated according to patient profiling data in FIG. 14C. Combining EpCAM and CD24 expression improved overall diagnostic accuracy. FIG. 25B is a table of diagnostic metrics determined from ROC curves. The dual marker set (EpCAM and CD24) has the highest detection accuracy of 97%. Note that CD63 alone is a poor diagnostic marker with area under curve (AUC)<0.7.

DETAILED DESCRIPTION

Aspects of the invention relate to the discovery that a plasmonic nanostructure designed to produce an electromagnetic field with a decay length comparable to the size of an exosome, has optical properties highly sensitive to any refractive index perturbation arising from the presence of exosomes. This phenomenon can be exploited to produce a detection device for the sensitive detection of exosomes in a sample. The use of such a detection device produces a surprisingly high detection sensitivity, on the order of $10^4$-fold higher than western blotting and $10^2$-fold higher than enzyme-linked immunosorbent assay (ELISA), with highly quantitative detection of specific exosomes from a sample. The herein described device and methods were developed to utilize the optical phenomena of surface plasmon resonance (SPR) for exosome detection.

One aspect of the invention relates to a plasmonic nanostructure in the form of a nano-plasmonic sensor. The nano-plasmonic sensor is used to capture the exosomes in a sample, and when used in the appropriate imaging system, described herein, generate an electromagnetic field that facilitates the detection and quantitation of the captured exosomes. The nano-plasmonic sensor is made from a transparent planar substrate. The planar substrate has two planar surfaces. A plasmonic film covers one surface of the substrate (the first surface). The plasmonic film covers the substrate except for at the location of apertures within the film that fully penetrate the film to the substrate layer. The apertures are referred to as nanoapertures due to their small size. The nanoapertures are present in a predefined pattern. The size and pattern of the nanoapertures on the sensor contributes to the function of exosome detection. This area that contains the pattern of nanoapertures is referred to as the "sensing area". The sensing area is a predetermined area of the sensor that binds the target exosomes and is positioned within the sensor for appropriate detection of the exosomes when in the contact of an imaging system. The sensing area also contains a capture agent attached to the metal film. The capture agent specifically binds to a molecule present on or inside the exosome (referred to herein as an exosome marker). Exosomes that are to be detected are bound to the sensor through binding of the exosome marker to the capture agent. When in the context of an imaging system, this binding of exosomes to the sensor causes a significant change in optical signal as compared to a sensor which has no bound exosomes. Such a change in optical signal can be detected (e.g., by a non-human machine) and used to indicate the presence of exosome(s) on the sensor.

Figure 1A:
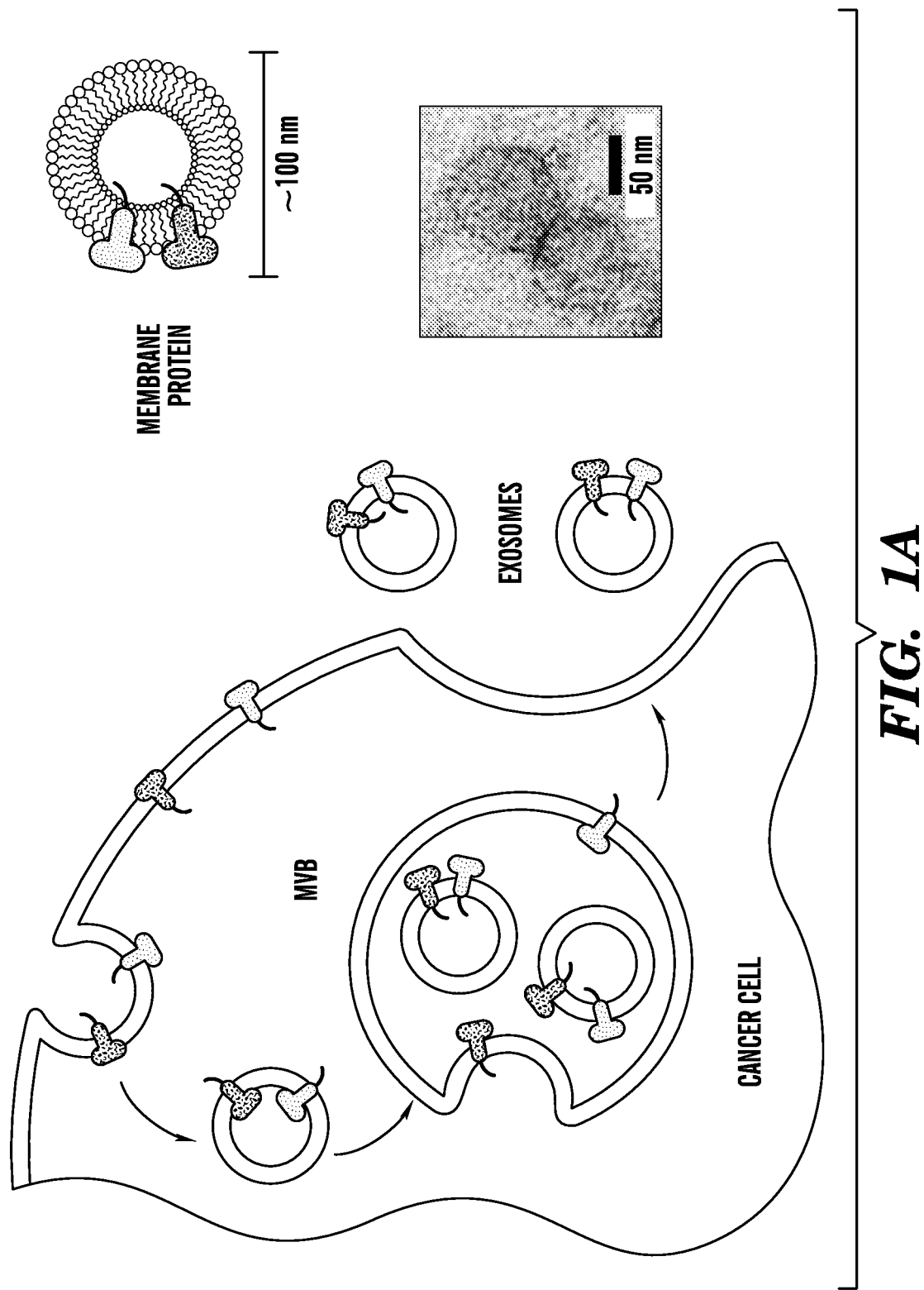
FIG. 1A-FIG. 1F illustrate label-free detection of exosomes with a nano-plasmonic exosome (nPLEX) sensor.
Figure 1B:
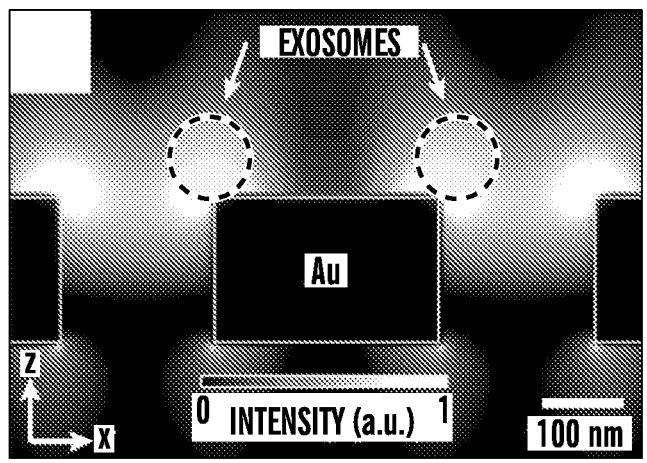
Figure 1C:
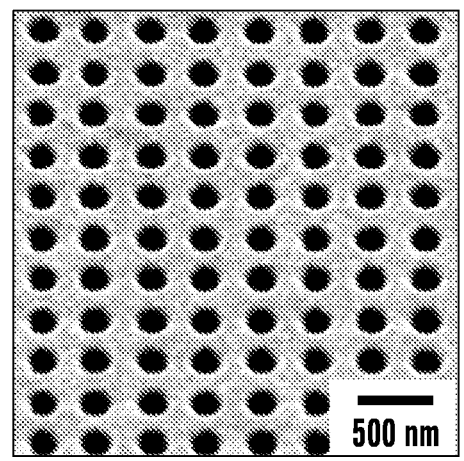

Without wishing to be bound by theory, the nano-plasmonic sensor is based on extraordinary optical transmission through a plurality of nanoapertures (Brolo, A. G., Nat. Photonics 2012, 6, 709-713; Gordon, R., et al., Acc Chem Res 2008, 41, 1049-1057; Yang, J. C., et al., Nano Lett 2008, 8, 2718-2724; Im, H., et al., Chem. Sci. 2010, 1, 688-696) rather than total internal reflection (Homola, J., Chem Rev 2008, 108, 462-493; Lee, H. J., et al., Anal. Chem. 2006, 78, 6504-6510) as used in commercial SPR systems. Briefly, when light having an appropriate wavelength or wavelength range is illuminated onto a plurality of nanoapertures, SPR can be excited in these nanoapertures. The light can then transmit through these nanoapertures, and its spectrum and intensity then measured. When one or more exosomes are attached to the surface of the plasmonic film comprising the nanoapertures (the sensing area), the presence of these exosomes changes the refractive index of the environment surrounding the nanoapertures, causing a shift in the SPR spectrum (FIG. 1E). As the shift is highly sensitive to the refractive index change, the shift increases with the refractive index change. Put another way, the larger the refractive index change, the larger the shift.

The transparent planar substrate is made of a material that can transmit at least 70%, 80%, 85%, 90%, 95%, or 99% of light having a wavelength in the ultraviolet-visible-infrared range, which includes wavelengths from approximately 100 nm to 3000 nm. Various materials (eg. glass, quartz, diamond, or a polymer) are known to have such properties. The skilled artisan can envision various combinations of such components that would produce a substrate with the desired optical properties. The substrate can contain one or more of such materials in sufficient quantities to confer the necessary properties. In one embodiment, the substrate is made of glass.

The plasmonic film is made of a plasmonic material. Various plasmonic materials are known in the art, such as noble metals (e.g., gold, palladium, platinum, rhodium, osmium, iridium, or silver), transition metals (e.g., titanium, aluminum, copper, or nickel), an alkali metal (e.g., lithium, sodium, potassium), metallic alloys, indium tin oxide, aluminum zinc oxide, gallium zinc oxide, titanium nitride, or graphene. In one embodiment, the plasmonic film is a metal film. In one embodiment, the metal film is a gold film. The thickness of the plasmonic film will be determined by the skilled practitioner for the specific intended use. In one embodiment, the film is about 10 nm to 1000 nm thick. In one embodiment, the film is about 10 nm to 750 nm, 10 nm to 500 nm, 25 nm to 500 nm, 50 nm to 500, 100 nm to 400 nm, or 200 nm to 300 nm thick.

In one embodiment, the nano-plasmonic sensor further comprises an adhesion layer located between the plasmonic film and the substrate surface. As is known in the art, for example, if a gold film is deposited directly on a substrate surface without an adhesion layer, the gold film has the tendency to delaminate. Therefore, without wishing to be bound by theory, the adhesion layer helps the plasmonic film adhere better to the substrate surface. The thickness of the adhesion layer can be varied depending upon the specific components of the sensor and the intended sensor use. The appropriate thickness will be determined by the skilled practitioner. In one embodiment, the adhesion layer is ≤60 nm, ≤50 nm, ≤40 nm, ≤30 nm, ≤20 nm, or ≤10 nm. In one embodiment, the adhesion layer is about 1 nm to 10 nm thick. The appropriate composition that makes up the adhesion layer will depend upon the circumstances of use, as determined by the skilled practitioner. In one embodiment, the adhesion layer is made of titanium, chromium, or combinations thereof.

In one embodiment, the pattern of the nanoapertures is a periodic pattern. In one embodiment, the nanoapertures are each separated by a periodicity of between about 100-1000 nm. In one embodiment, the nanoapertures are separated by a periodicity of between about 400-800 nm. In one embodiment, the nanoapertures are separated by a periodicity of between about 450-500 nm. The use of a non-periodic pattern, such as a pseudo-random pattern or a random pattern, is also envisioned.

In one embodiment, the periodic pattern is that of a lattice. A variety of lattice types are known to the skilled practitioner and can be used for the pattern of nanoapertures. In one embodiment, the lattice is square. In one embodiment, the lattice is rectangular. In one embodiment, the lattice is triangular. In one embodiment, the lattice is hexagonal.

The nanoapertures on a given sensing area will typically all have the same shape, although the use of a plurality of different shapes is also envisioned. A variety of shapes can be used to generate the sensing area (e.g., circular, elliptical, square, rectangular, triangular, hexagonal, oval, or combinations thereof). In one embodiment, the nanoapertures are circular. In one embodiment, at least one dimension of the nanoaperture is between 10-1000 nm. In one embodiment, at least one dimension of the nanoaperture is between 50-300 nm.

In one embodiment, the nanoapertures are about 50 nm to 400 nm in diameter. In one embodiment, the nanoapertures are about 100 nm to 300 nm in diameter. In one embodiment, the nanoapertures are about 200 nm in diameter.

Figure 3A:
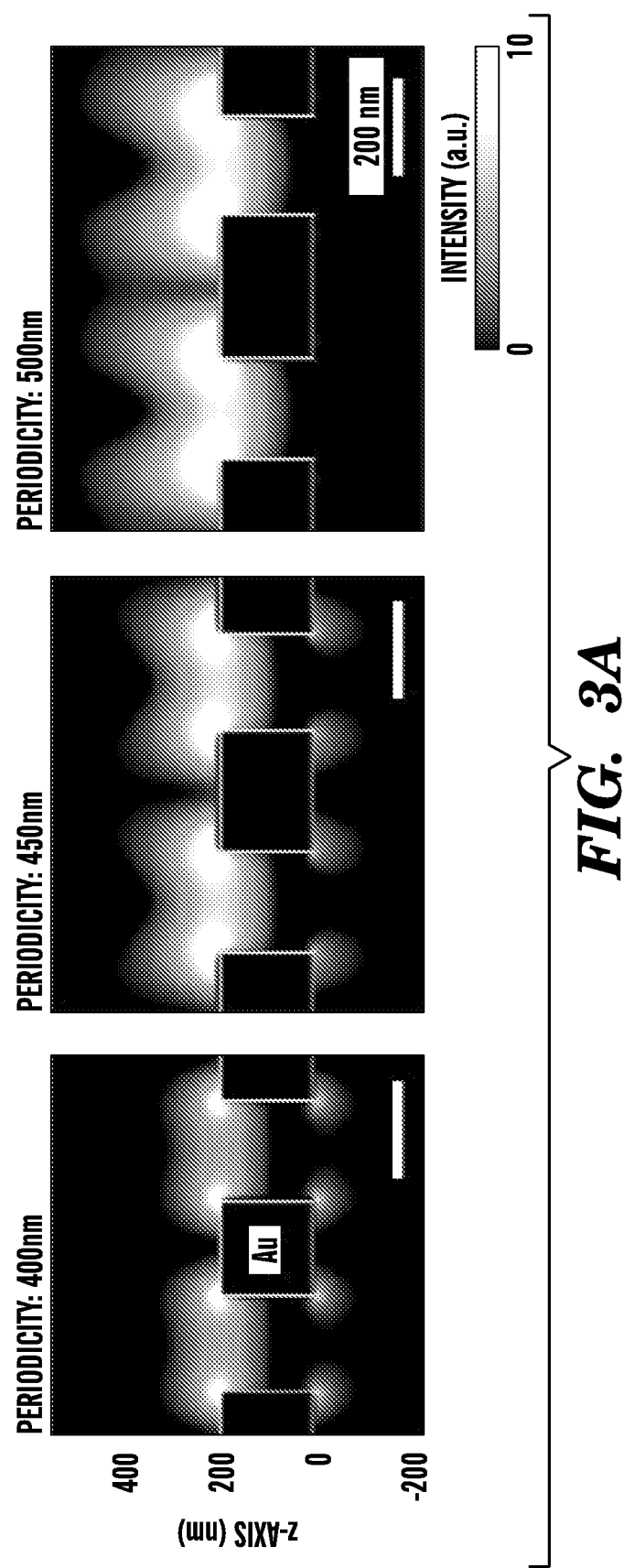
FIG. 3A-FIG. 3C are simulation results that demonstrate sensitivity optimization of the nPLEX sensor.
Figures 3B, 3C:
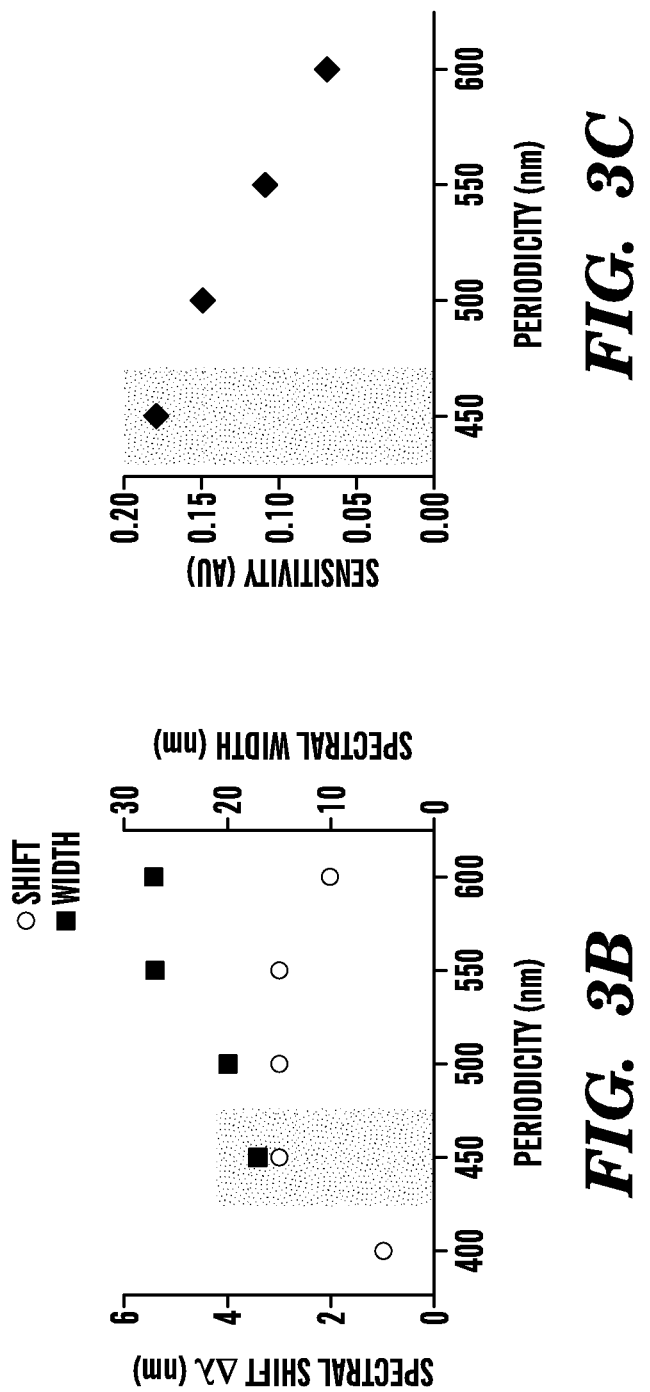

It should be noted that the nanoaperture dimensions, periodicity, and pattern contribute to the decay length of an electromagnetic field emanating from the surface of the plasmonic nanostructure at surface plasmonic resonance. Judicious selection of the appropriate nanoaperture dimensions, periodicity, and pattern (e.g., lattice pattern), results in the production by the plasmonic nanostructure of an electromagnetic field at SPR having a decay length comparable to the size of an exosome, resulting in high detection sensitivity for exosomes. For example, a pattern and a nanoaperture shape and dimension can be pre-selected, and then computational simulations of electromagnetic field spatial distribution as a function of periodicity can be performed (FIG. 3A). By way of non-limiting example, periodicity of around 450 nm for square lattice and circular nanoaperture diameter of about 200 nm was found to yield the highest detection sensitivity (FIG. 3B-FIG. 3C). Accordingly, in one embodiment, the nano-plasmonic sensor comprises a plurality of circular nanoapertures arranged in a square lattice with a periodicity of about 450 nm, and the nanoaperture diameter is about 200 nm. Those skilled in the art can also pre-select a lattice and periodicity, and then optimize the nanopaperture dimensions for highest detection sensitivity through similar computational simulations. Alternatively, those skilled in the art can also pre-select nanoaperture dimensions and periodicity, and then optimize the lattice for highest detection sensitivity through similar computational simulations.

Methods of performing computational simulations for electromagnetism are well known in the art. See "Photonic Crystals: Molding the Flow of Light (Second Edition)" by J. D. Joannopoulos (Princeton University Press 2008). For example, a finite-difference-time-domain (FDTD) technique can be used to perform the simulations. Any commercial or open-source software that is based on FDTD can be used, including, but are not limited to, Meep, Lumerical, XFdtd®, or WOLFSIM.

The nano-plasmonic sensor can comprise one or more sensing areas (e.g., at least 2, 3, 4, 5, 6, 7, 8, 9, or 10 sensing areas). In one embodiment, the sensing areas can be arranged in a pre-defined pattern. In one embodiment, all sensing areas are functionalized with the same capture agent. In one embodiment, different sensing areas are functionalized with different capture agents or some having no capture agents. A sensing area having no capture agent can be used as a control in some embodiments. The density of sensing areas on the nano-plasmonic sensor can be very high, such as at least $10^3$ per $cm^2$, at least $10^4$ per $cm^2$, at least $10^5$ per $cm^2$, or at least $10^6$ per $cm^2$.

In one embodiment, the nano-plasmonic sensor further comprises a molecular spacer directly attached to the metal film. The molecular spacer is attached to the capture agents either directly or via a linking agent which is in turn directly attached to the molecular spacer and also directly attached to the capture agent. Without wishing to be bound by theory, the molecular spacer can provide steric flexibility and thus can increase the percentage of exosomes captured on the sensor surface. The molecular spacer can be any molecule that can form a self-assembled monolayer (SAM) (e.g., silanes), or a cleavable or non-cleavable polymer. In one embodiment, polyethylene glycol (PEG) is used to create the molecular spacer. In one embodiment, the molecular spacer comprises long-chain PEG and short-chain PEG at a ratio of about 1:1 to 1:10. In one embodiment, the ratio of long-chain PEG and short-chain PEG is about 1:3.

In one embodiment, the linking agent comprises protein A/G. In one embodiment, the linking agent comprises neutravidin.

It is also contemplated that the capture agent can be directly attached to the molecular spacer.

The capture agent is a molecule which specifically binds to a component of an exosome. The component of an exosome that is specifically bound by the capture agents is referred to herein as an exosome marker. In one embodiment, the capture agent comprises an antibody or a portion thereof which specifically binds to the exosome marker. In one embodiment, the exosome marker is present on all exosomes found in a biological sample. Such a marker is referred to herein as a pan-exosomal marker. In one embodiment, the exosome marker is present on a subset of exosomes found in a biological sample. The exosome that contains the marker for which the capture agent binds is referred to herein as a target exosome.

In one embodiment, the exosome marker is associated with a disease or disorder. The composition of exosomes (both internally and at the membrane) is known to reflect the compositions of the cells from which they arise. As such, an increased presence of exosomes (e.g., in a biological sample obtained from a subject) identified as having a marker typically found on a cell with a disease or disorder can be used to identify the presence of that disease or disorder in a subject. One example of such a disease is cancer. Other such disease and disorders include cardiovascular disease, diabetes, and infection. Specific markers of such diseases and disorders are known in the art, and the identification of which is within the ability of the skilled practitioner.

In one embodiment, the exosome marker is a marker for cancer. In one embodiment, the marker for cancer is selected from the group consisting of epithelial cell adhesion molecule (EpCAM), CD24, cancer antigen 19-9 (CA19-9), Claudin 3, cancer antigen 125 (CA-125), MUC18, epidermal growth factor receptor (EGFR), human epidermal growth factor receptor 2 (HER2), CD41, CD45, D2-40, heat shock protein 90 (HSP90), HSP70, CD63, CD44, FOLR1, EPHA2, MUC1, CD9, CD81, TSG101, LAMP1, Flotillin 1, Flotillin 2, and combinations thereof.

Figure 19:
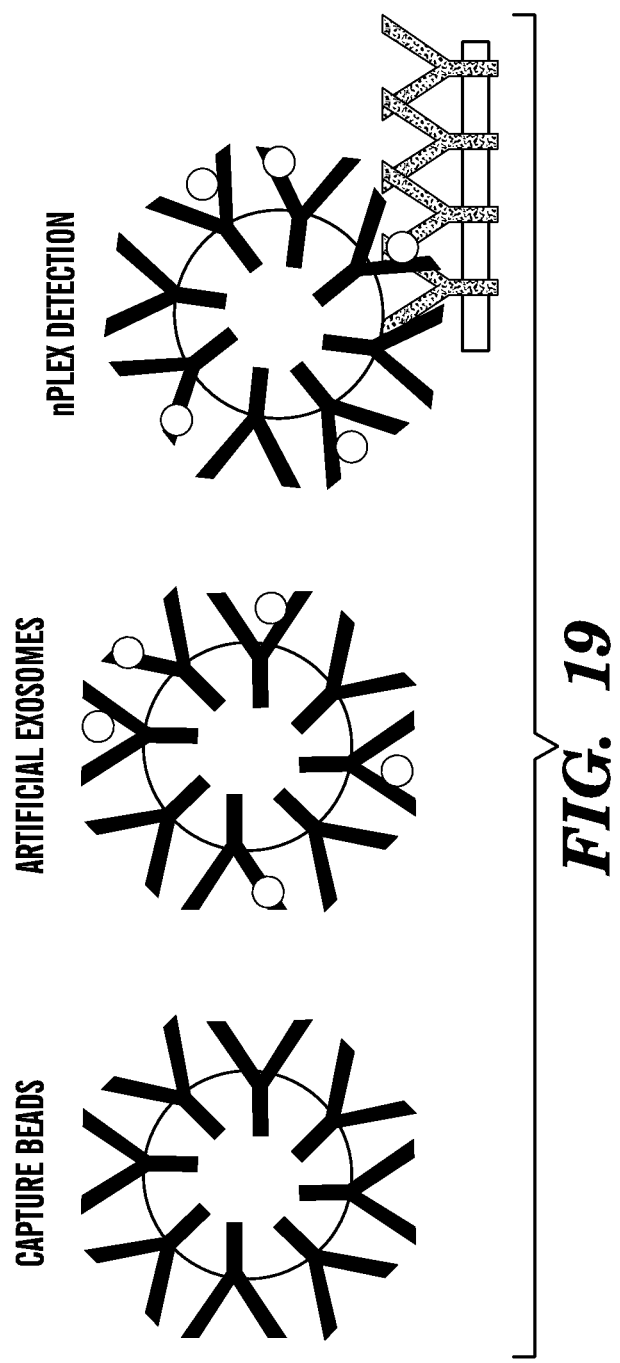
FIG. 19 is a detection scheme for intravesicular markers. Intravesicular protein markers from exosome lysis are first captured by nanoparticles (beads) coated with capture antibodies. The protein-bead conjugates act as artificial exosomes on which intravesicular markers are accessible. The artificial exosomes are then captured on the nPLEX surface same as the extravesicular marker detection.

In one embodiment, the intravesicular marker is selected from a group consisting of a protein, lipids, small molecules, mRNA, microRNA, lncRNA, and DNA. FIG. 19 presents one detection scheme for intravesicular marker using the nano-plasmonic sensor.

Figure 4A:
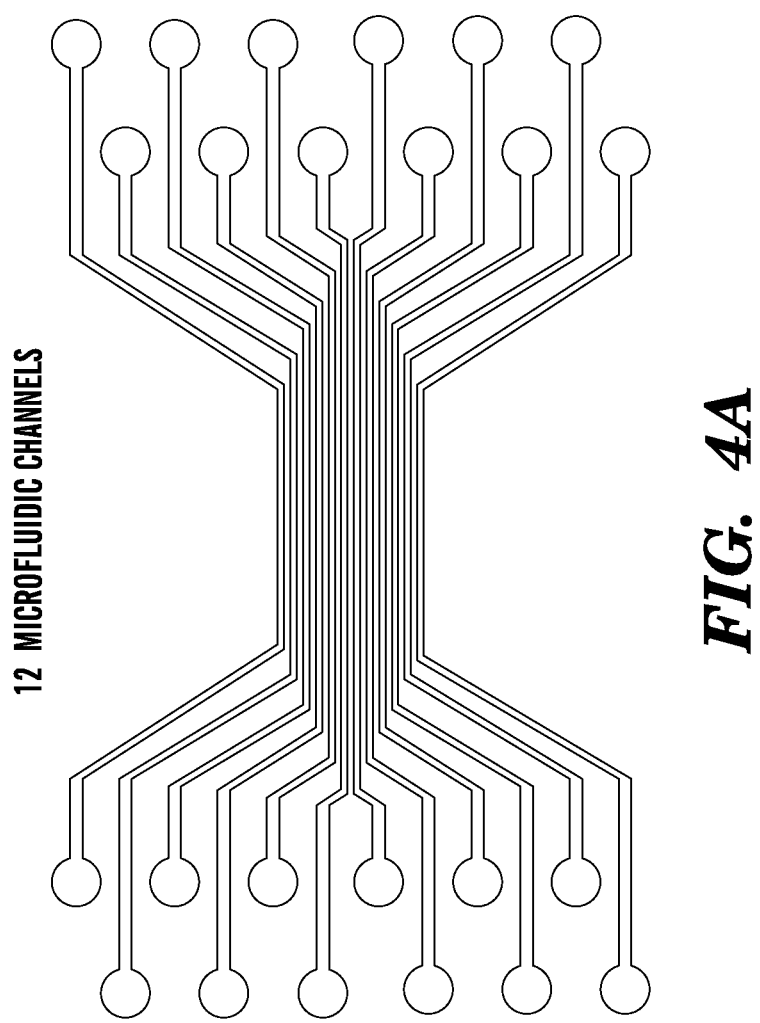

The nano-plasmonic sensor can further comprise one or more microfluidic channels (e.g., 2, 3, 4, 5, 6, 7, 8, 9, 10, or more microfluidic channels). A portion of each microfluidic channel is disposed on each sensing area. FIG. 4A-FIG. 4C provide an exemplary embodiment of a nano-plasmonic sensor with microfluidic channels. The use of microfluidics in the methods of detection described herein significantly reduces the amount of sample needed for detection.

The microfluidic channels can have multiple functions. For example, the microfluidic channels can be used to facilitate the assemblage of the nano-plasmonic sensor such as by facilitating attachment of the molecular spacer to the plasmonic film, the linking agent to the molecular spacer, or the capture agent to the linking agent. This is accomplished by flowing a solution comprising the molecular spacer, linking agent, or capture agent through the microfluidic channels at the appropriate time in assemblage of the sensor. Once completely assembled, a sample suspected of containing exosomes can be added to the sensor to thereby flow through the channels under conditions appropriate for bindings of the exosome marker to the capture agent. Under the appropriate conditions the exosomes present in the sample will bind to the sensing area of the sensor.

In one embodiment, the microfluidic channels are fluidically independent (e.g., each channel can have its own fluid inlet and outlet). When the channels are fluidically independent, each channel can be independently functionalized to comprise a capture agent that specifically binds to a different exosome marker. Therefore, a plurality of exosome markers can be screened in parallel, significantly reducing detection time. In one embodiment, two or more microfluidic channels can be fluidically coupled (e.g., two or more microfluidic channels can share the same fluid inlet).

Figure 7A:
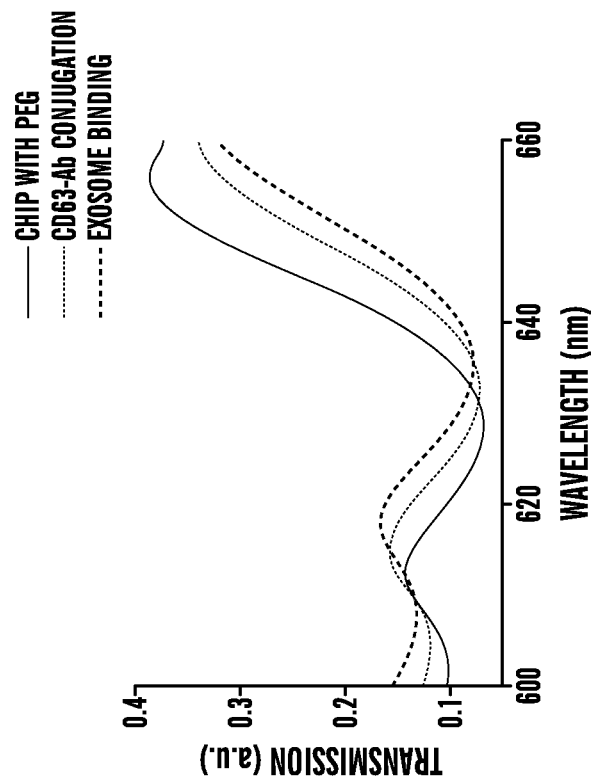
FIG. 7A-FIG. 7C indicates spectral shifts upon antibody (Ab) conjugation and specific exosome binding. nPLEX sensors were conjugated with either CD63 (FIG. 7A) or IgG control (FIG. 7B) antibodies. Exosomes from ovarian cancer cells (CaOV3) were subsequently introduced. Transmission spectral shifts associated with antibody conjugation and specific exosome binding were measured. Similar spectral shifts were observed for both CD63 and control antibody conjugation, which indicated similar extent of antibody grafting onto the sensor surface. Exosome binding, however, was only observed with the CD63-specific sensor (FIG. 7A); the control sensor (FIG. 7B) displayed negligible binding.
Figure 7B:
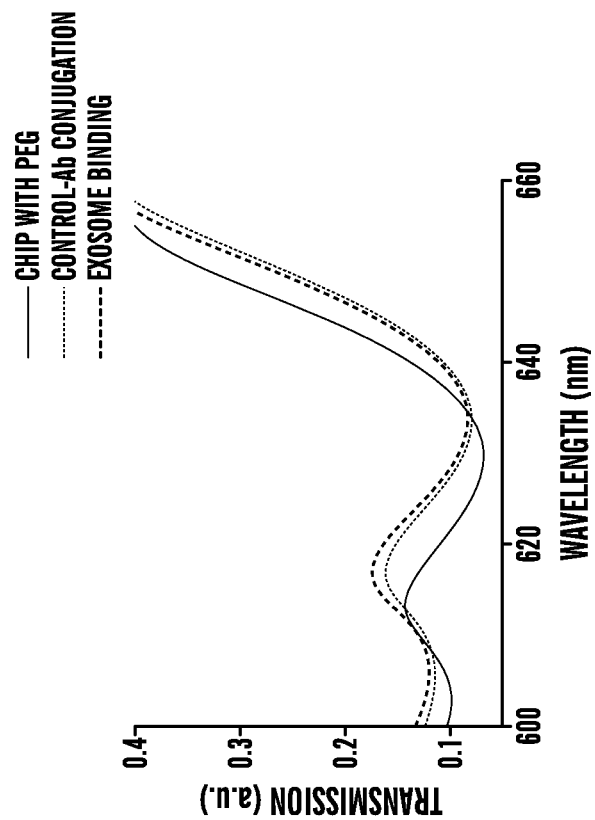
Figures 7C, 8:
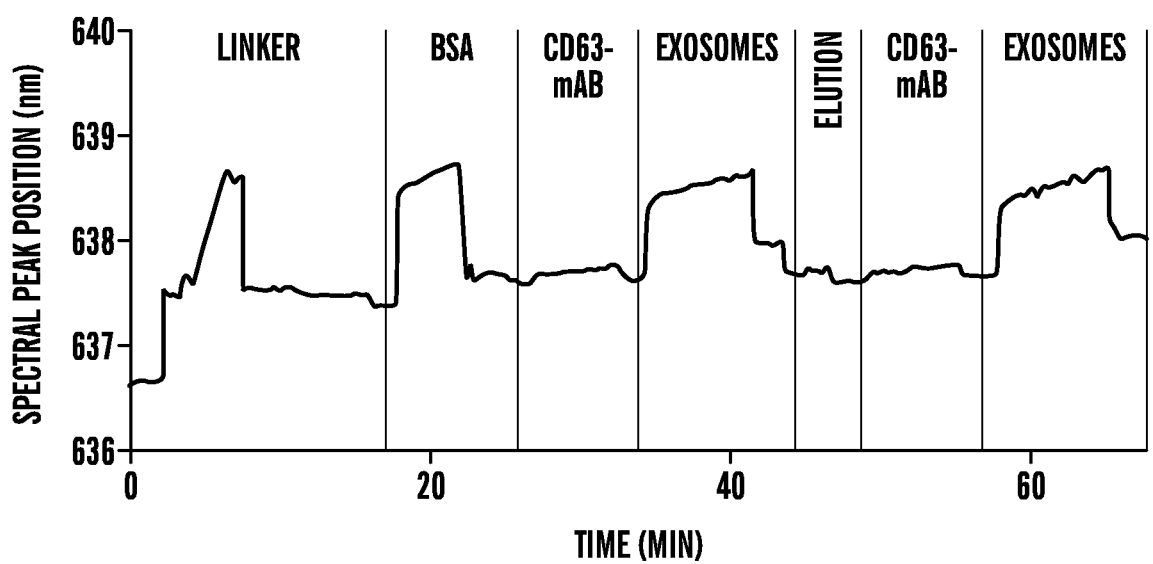
FIG. 8 is a real-time sensorgram. A series of operation were performed, namely surface blocking with bovine serum albumin (BSA), conjugation with CD63 monoclonal antibody (CD64-mAb) and exosome capture, by sequentially flowing reagents to a nPLEX sensor. The processes were monitored in-situ by tracking the transmission spectral shifts. The entire assay from the antibody-binding to exosome capture was complete in <30 minutes. Importantly, the chip surface could be regenerated for repeated uses by eluting antibodies and exosomes.

The nano-plasmonic sensor can be regenerated after each use, meaning that the capture agent and the captured exosomes can be removed from the metal film surface, and the sensor can be used for a new round of exosome detection. This can be done, for example, by eluting antibodies using reagents (FIG. 8). By way of examples only, antibodies can be eluted at low pH using glycine or citric acid buffer. Alternatively, antibodies can be eluted at neutral pH using KSCN or NaSCN. Moreover, antibodies can be eluted at high pH using glycine-NaOH, diethylamine, or sodium borate. The capability of regenerating the nano-plasmonic sensor can help drive down material cost and reduce waste, rendering this invention more attractive.

The nano-plasmonic sensor provided herein can be manufactured using standard methods. The transparent planar substrate can be a commercial product (e.g., a microscope coverslip, a glass slide, a quartz slide, or a diamond slide) or custom made. The metal film can be deposited onto the substrate through a variety of methods, such as thermal evaporation, e-beam evaporation, or sputtering. The nano-apertures and associated pattern can be generated by e-beam lithography, photolithography, template-stripping lithography (Nagpal, P., et al., Science 2009, 325, 594-597; Im, H. et al. ACS Nano 2011, 5, 6244-6253), molecular printing method (MacBeath, G. & Schreiber, S. L. Science 2000, 289, 1760-1763), wet etching, focused ion beam, or any combination thereof.

The molecular spacer, linking agent, and capture agent can be attached onto the metal film surface in a sequential manner. An activation step can also be used to facilitate chemical bond formation. Silane chemistry or Au—S chemistry can be used to attach the molecular spacer to the substrate surface.

It is also contemplated that the molecular spacer, linking agent, and capture agent are conjugated first before attaching to the substrate surface.

Imaging System

The nano-plasmonic sensor described herein can further be incorporated into a platform for highly sensitive, label-free, and high-throughput exosome detection and marker expression level analysis. Because the nano-plasmonic sensor enables transmission measurement, another aspect of the invention relates to an imaging system that is used to perform transmission measurements on the nano-plasmonic sensor.

The imaging system comprises a light source, a detector, and the nano-plasmonic sensor provided herein, wherein light produced by the light source can transmit through the nano-plasmonic sensor, and then be detected by the detector. In one embodiment, the imaging system is based on the use of a microscope. Such an imaging system is depicted in FIG. 5A.

Figure 1D:
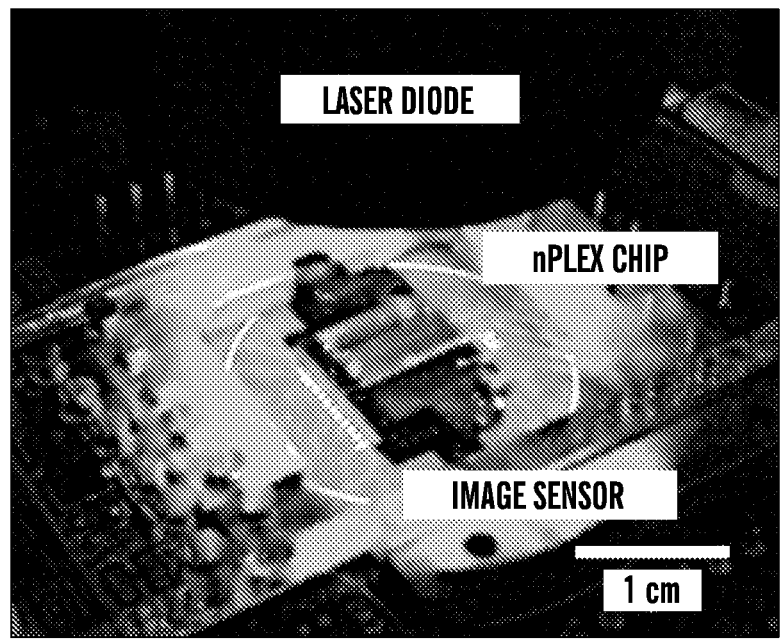
Figure 1E:
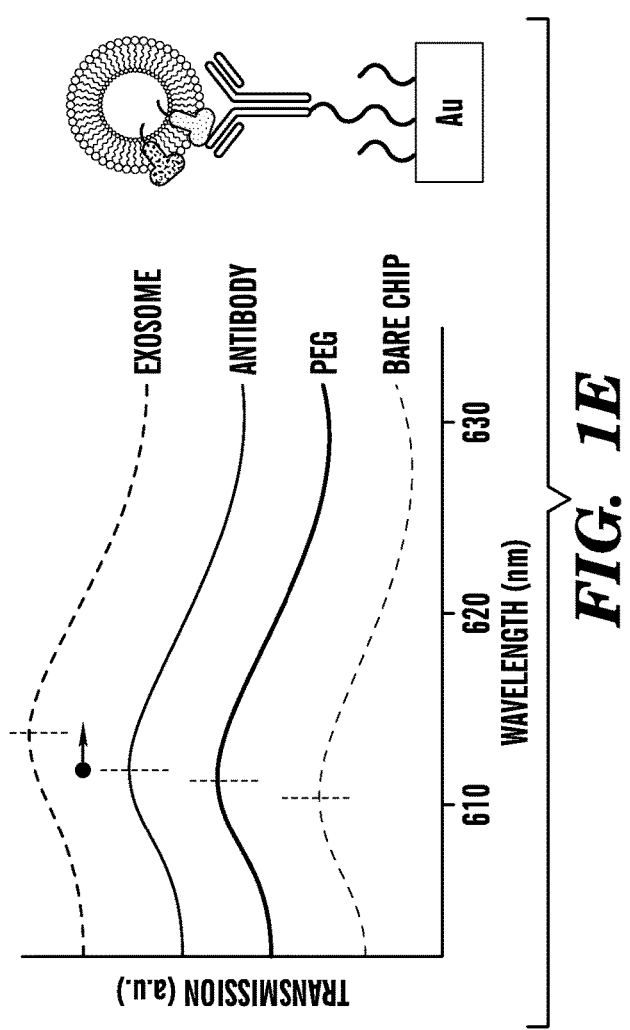
Figure 5B:
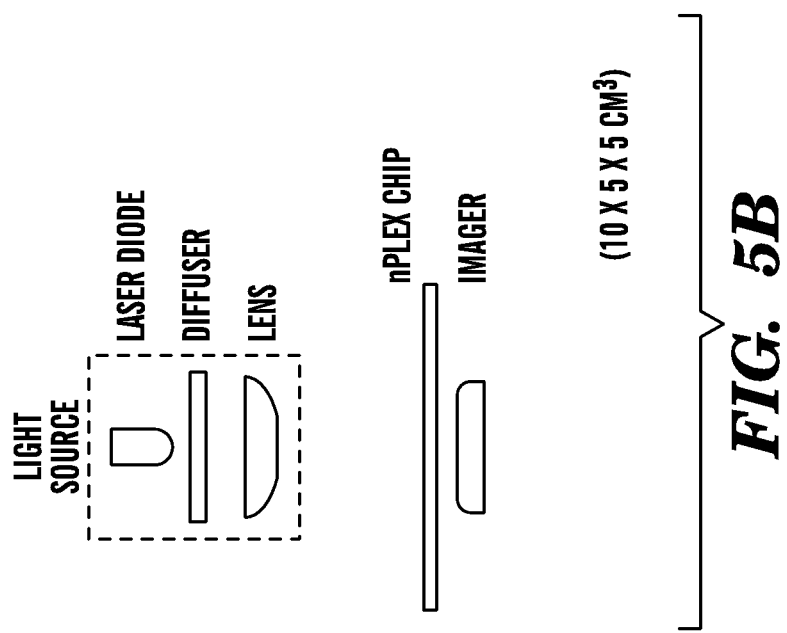
FIG. 5A-FIG. 5D illustrate the measurement setups for nPLEX sensors.

In one embodiment, the imaging system is small and portable such as that depicted in FIG. 5B and FIG. 1D, allowing for detection of biological components such as exosomes in an easy and rapid manner. The smaller imaging system offers at least two advantages over a conventional microscope, portability and low cost arising from the small number of optical components required.

Figure 5A:
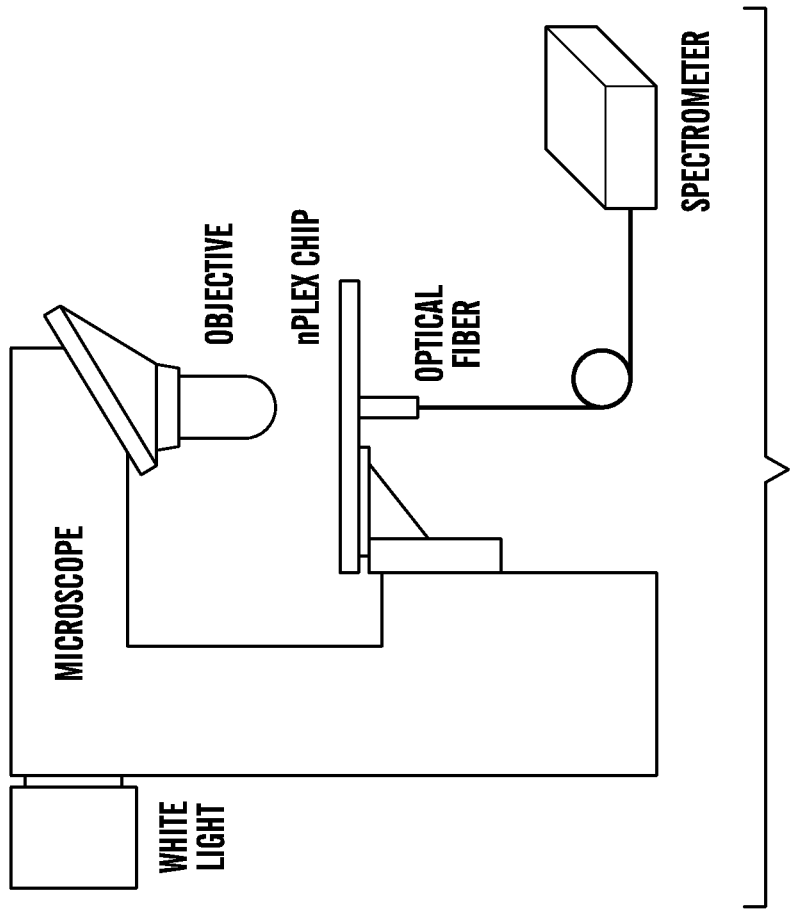

FIG. 5A-FIG. 5B compares an exemplary embodiment of the imaging system (FIG. 5B) to an exemplary conventional microscope (FIG. 5A). A skilled artisan can readily appreciate the simplicity of the imaging system. It should be noted that even though FIG. 5B shows a vertical configuration, it is contemplated that a horizontal configuration or any other reasonable configuration can function in a similar manner. When exosomes are bound on the nano-plasmonic sensor surface, the resultant spectral shift compared to a negative control can be quantified as either a change in SPR peak wavelength or a change in intensity at a fixed wavelength (see FIG. 5C for exemplary illustration). A significant change would indicate the detection of exosomes. A change is significant when its magnitude is at least a minimum detection level. The minimum detection level depends on several factors including, but are not limited to, detector sensitivity, system stability, or any combination thereof. For example, the minimum detection level can be determined by three times of the standard deviation of a spectral peak position measured at a steady state for a certain period of time. In one embodiment, a change is significant when its magnitude is at least 10%, 20%, 40%, 60%, 80%, 100%, 150%, or 200% higher than the minimum detection level.

The small and portable imaging system described herein can also be adapted to incorporate a nano-plasmonic sensor that is designed for the detection of biomolecular targets such as those described in U.S. Patent Publication 2013/0065777, the contents of which are incorporated herein by reference. Such imaging systems are also encompassed by the instant invention.

In one embodiment of the imaging system, the system is designed to measure the light intensity at a fixed wavelength.

Therefore, the system can compare the light intensity difference at a fixed wavelength before and after a sample is introduced to the nano-plasmonic sensor.

In one embodiment, the light source is monochromatic. In one embodiment, the monochromatic light source is a laser. In one embodiment, the monochromatic light source is a light-emitting diode (LED).

In one embodiment, the light source is broadband, and the imaging system further comprises a conditioning element (e.g., a bandpass filter) that can select a wavelength from the broadband source.

Generally, the detector can be any photodetector that is sensitive to photons, including, but is not limited to, an active-pixel-sensor (APS), a charge-coupled device (CCD), a photodiode, or a photomultiplier. In one embodiment, the detector is a metal-oxide-semiconductor (CMOS) sensor. In one embodiment, the detector is a monochromatic or color CCD.

In one embodiment, the imaging system can further comprise one or more conditioning elements to homogenize light intensity over a desired area that includes a plurality of sensing areas, which allows measurements at these sensing areas simultaneously. The conditioning element for light intensity homogenization includes, but is not limited to, a diffuser, a lens, or any combination thereof.

In one embodiment, the conditioning element is a polarizer.

In one embodiment, the imaging system can further comprise a slot, a pin, a screw, or the like to secure the nano-plasmonic sensor.

Another aspect of the invention relates to a method of detecting exosomes in a sample using the nano-plasmonic sensor, in the context of an imaging system, described herein. The method comprises introducing a sample suspected of containing one or more exosomes (also referred to herein as a test sample) onto a nano-plasmonic sensor under conditions which promote binding of the exosome marker to the capture agent of the sensor. The specific capture agent on the sensor will determine the target exosomes to be detected in the method. Following an appropriate incubation of the sample on the sensor to promote binding, the sensor is washed to remove unbound materials. The sensor is then illuminated appropriately for the specific detection of the bound exosomes, with the light being transmitted through the sensing area of the sensor. The light transmitted through the sensing area of the sensor is detected and measured. The measured light is analyzed, e.g., by comparing to the light transmitted and detected/measured using a negative control. Such a comparison will yield a significant difference when exosomes are present. The detection of a significant change in the transmitted light from a negative control indicates the presence of exosomes in the sample.

In one embodiment, the detected difference is a shift in peak wavelength. In one embodiment the detected difference is an intensity change at a fixed wavelength.

The determination of appropriate negative controls is within the ability of the skilled artisan. In one embodiment, the negative control is a solution that is substantially free of exosomes or exosome lysates (e.g., a standard PBS solution). Such a solution can be used with the identical sensing area as the test sample. In one embodiment, the negative control is generated by the deposition of a test sample onto a sensing area that is not functionalized with a capture agent (e.g. is instead functionalized with a control antibody that does not bind to exosomes). That area is processed identically to the other sensing area, illuminated, and the transmitted signal is then detected, and analyzed accordingly.

In one embodiment, the method can be performed using a conventional microscope with or without a spectrometer, as described herein. In one embodiment, the method can be performed using the portable imaging system described herein.

In one embodiment, a secondary label (e.g. in the form of a metallic nanoparticle, a magnetic nanoparticle, a dielectric nanoparticle, a semiconductor nanoparticle, or a diamond nanoparticle) comprising an agent (e.g., the capture agent) that specifically binds to the exosome marker can be introduced to the captured exosomes. The secondary label amplifies the detection signals, and thus increases the sensitivity of the method to detect exosomes present in lower concentrations within the sample. Without wishing to be bound by theory, signal amplification is thought to result from larger refractive index perturbation due to the presence of the secondary label. The secondary label may comprise a metallic nanoparticle, a magnetic nanoparticle, a dielectric nanoparticle, a semiconductor nanoparticle, or a diamond nanoparticle. In one embodiment, the metallic nanoparticle is a gold nanoparticle having any shape (e.g., a star, a sphere, a cube, a rod, a bowtie, or a dumbbell).

The agent on the secondary label may be the same as the capture agent on the sensor, or may be a different capture agent.

The secondary label is introduced to the capture exosomes under conditions appropriate for binding of the marker to the capture agent on the secondary label. Following binding, appropriate washing may also be performed if necessary. The secondary label can also be introduced to the sample suspected of containing exosomes before the sample is introduced onto the nano-plasmonic sensor. Signal detection is then performed as described herein.

The invention can have significant applications in both basic and clinical research. Better understanding of exosomal protein compositions could answer fundamental questions about, for example, exosome-mediated intercellular communication (Mathivanan, S., Ji, H. & Simpson, R. J., J. Proteomics 2010, 73, 1907-1920; Valadi, H. et al., Nat. Cell Biol. 2007, 9, 654-659) and tumor micro-environment (Peinado, H. et al., Nat. Med. 2012, 18, 883-891; Grange, C. et al., Cancer Res. 2011, 71, 5346-5356). For clinical care, the invention can uncover novel diagnostic and predicative biomarkers and, importantly, evaluate tumor response to therapy in individual patients.

Another aspect of the invention relates to a method for quantitating the amount of a subset of exosomes (e.g, those expressing a specific target marker associated with a disease or disorder) in a sample. The method of determining the expression level of a target marker in a sample of exosomes comprises detecting total exosomes in the sample using a capture agent that specifically binds a pan-exosomal marker, detecting exosomes in the sample expressing the target marker using a capture agent that specifically binds the target marker, and calculating the ratio of exosomes with target marker to total exosomes. The ratio indicates the average expression level of the target marker per exosome from the sample.

In one embodiment, the pan-exosomal marker is CD63.

In one embodiment, the target marker is associated with a disease or disorder (e.g., cancer, cardiovascular disease, diabetes, and infection).

Because it is known that exosomes carry molecular information (e.g., target markers) of cells from which the exosomes are derived, determination of the expression level of a target marker in a sample of exosomes provides information regarding the cellular makeup of a subject, and in turn can be used for diagnosis or prognosis of a disease or disorder in that subject. By taking sample at different times, the progression of a disease can be monitored.

For example, in ovarian cancer, the expression levels of EpCAM, CD24, CA19-9, Claudin3, CA-125, MUC18, and EGFR are known to be elevated in the cancer cells. Using the method provided herein to determine the expression levels of one or more of these target markers in a biological sample from a subject, a skilled practitioner can non-invasively determine whether ovarian cancer is present at the time the sample is obtained. In one embodiment, EpCAM and CD24 are used as markers for ovarian cancer. By taking sample at different times, the progression of the cancer can be monitored.

Markers associated with diseases or disorders such as those shown in Table 2 are known in the art and can be identified and utilized in the methods of the invention by the skilled practitioner. In one embodiment, the disease is infection with a pathogen (e.g., virus, bacteria, or parasite) and the target marker is produced by the pathogen (e.g., a viral receptor).

In one embodiment regarding cardiovascular disease, exosomes or microparticles from endothelial cells can be used. In one embodiment, exosomes arising from immune cells can be targeted for detection.

By tracking the expression levels of certain target markers on exosomes over the course of a treatment, one can determine the treatment efficacy. For example, a reduction in the expression level over time of marker associated with a disease or disorder indicates that the treatment is effective, whereas an increase in the expression level over time indicates that disease or disorder is worsening.

The skilled practitioner will recognize that all compositions, uses and methods described herein for exosomes can be adapted for detection and quantitation of other nanovesicles from the information provided herein. As such, another aspect of the invention relates to the compositions, their use, and the associated methods described herein for detection and quantitation of other types of nanovesicles. Examples of such nanovesicles are known in the art, provided herein, and include, without limitation, liposome, vacuole, lysosome, transport vesicle, secretory vesicle, gas vesicle, matrix vesicle, and multivesicular body.

The present invention may be as defined in any one of the following numbered paragraphs:
1. A nano-plasmonic sensor for detecting exosomes comprising,
a) a transparent planar substrate;
b) a metal film disposed onto one surface of the substrate, wherein the metal film comprises a plurality of nanoapertures in a predefined pattern to create a sensing area that produces surface plasmon resonance upon illumination; and
c) a capture agent attached to the metal film, wherein the capture agent specifically binds to an exosome marker.
2. The nano-plasmonic sensor of paragraph 1, further comprising a molecular spacer directly attached to the metal film, and a linking agent directly attached to the molecular spacer and directly attached to the capture agent.
3. The nano-plasmonic sensor of paragraph 1 or 2, wherein the metal film comprises a noble metal, a transition metal, an alkali metal, or any combination thereof.
4. The nano-plasmonic sensor of any one of paragraphs 1 to 3, wherein the substrate comprises glass, quartz, diamond, or a polymer.
5. The nano-plasmonic sensor of any one of paragraphs 1 to 4, wherein the metal film comprises gold and the substrate comprises glass.
6. The nano-plasmonic sensor of any one of paragraphs 1 to 5, wherein the metal film is between 50 to 500 nm thick.
7. The nano-plasmonic sensor of any one of paragraphs 1 to 6, further comprising an adhesion layer located between the metal film and the substrate surface.
8. The nano-plasmonic sensor of paragraph 7, wherein the adhesion layer is less than about 50 nm thick.
9. The nano-plasmonic sensor of any one of paragraphs 1 to 8, wherein the predefined pattern is periodic.
10. The nano-plasmonic sensor of paragraph 9, wherein the nanoapertures have a dimension and periodicity that produce an electromagnetic field with a decay length of about 50 nm to 200 nm when the nanoapertures are illuminated by light with a wavelength close to or at the surface plasmon resonance.
11. The nano-plasmonic sensor of any one of paragraphs 1 to 10, wherein the nanoapertures are circular, elliptical, rectangular, triangular, oval, or hexagonal.
12. The nano-plasmonic sensor of paragraph 11, wherein the circular nanoapertures are about 50 nm to 300 nm in diameter, and wherein the periodicity is about 400 nm to 700 nm.
13. The nano-plasmonic sensor of paragraph 12, wherein the circular nanoapertures are about 200 nm in diameter, and wherein the periodicity is about 450 nm to 500 nm.
14. The nano-plasmonic sensor of any one of paragraphs 2 to 13, wherein the molecular spacer comprises polyethylene glycol (PEG).
15. The nano-plasmonic sensor of paragraph 14, wherein the PEG comprises long-chain PEG and short-chain PEG in a ratio of about 1:3.
16. The nano-plasmonic sensor of any one of paragraphs 2 to 15, wherein the linking agent comprises protein A/G or neutravidin.
17. The nano-plasmonic sensor of any one of paragraphs 1 to 16, wherein the capture agent comprises an antibody or a portion thereof.
18. The nano-plasmonic sensor of any one of paragraphs 1 to 17, wherein the exosome marker is an extravesicular marker or an intravesicular marker.
19. The nano-plasmonic sensor of any one of paragraphs 1 to 18, wherein the exosome marker is present on all exosomes found in a biological sample.
20. The nano-plasmonic sensor of any one of paragraphs 1 to 18, wherein the marker is present on a subset of exosomes found in a biological sample.
21. The nano-plasmonic sensor of any one of paragraphs 1 to 20, wherein the exosome marker is associated with a disease or disorder.
22. The nano-plasmonic sensor of paragraph 21, wherein the disease or disorder is selected from the group consisting of cancer, cardiovascular disease, diabetes, and infection.
23. The nano-plasmonic sensor of paragraph 22, wherein the exosome marker is selected from the group consisting of epithelial cell adhesion molecule (EpCAM), CD24, cancer antigen 19-9 (CA19-9), Claudin 3, cancer antigen 125 (CA-125), MUC18, epidermal growth factor receptor (EGFR), human epidermal growth factor receptor 2 (HER2), CD41, CD45, D2-40, heat shock protein 90 (HSP90), HSP70, CD63, CD44, FOLR1, EPHA2, MUC1, CD9, CD81, TSG101, LAMP1, Flotillin 1, Flotillin 2, and combinations thereof.
24. The nano-plasmonic sensor of paragraph 18, wherein the intravesicular marker is selected from a group consisting of a protein, a lipid, a small molecule, mRNA, microRNA, lncRNA, and DNA.

25. The nano-plasmonic sensor of any one of paragraphs 1 to 24, further comprising at least one microfluidic channel, wherein a portion of the microfluidic channel is disposed on the sensing area.

26. The nano-plasmonic sensor of paragraph 25 comprising a plurality of microfluidic channels, wherein each channel comprises a capture agent that specifically binds to a different exosome marker.

27. An imaging system comprising a light source, a detector, and a nano-plasmonic sensor of any one of paragraphs 1 to 26, wherein the detector is positioned to detect light produced by the light source and transmitted through the nano-plasmonic sensor.

28. The imaging system of paragraph 27, wherein the system is portable.

29. The imaging system of paragraph 27 or 28, further comprising a conditioning element for conditioning the light produced by the light source.

30. The imaging system of paragraph 29, wherein the conditioning element comprises a diffuser, a lens, a filter, or any combination thereof.

31. The imaging system of any one of paragraphs 27 to 30, wherein the light source is monochromatic or broadband.

32. The imaging system of paragraph 31, wherein the monochromatic light source is a laser or light emitting diode (LED).

33. The imaging system of any one of paragraphs 27 to 32, wherein the detector is an active-pixel sensor (APS), a charge-coupled device (CCD), a photodiode, or a photomultiplier.

34. The imaging system of paragraph 33, wherein the APS is a complementary metal-oxide-semiconductor (CMOS) sensor.

35. The imaging system of paragraph 33, wherein the CCD is monochromatic or color.

36. A method of detecting exosomes in a sample, comprising
a) introducing a sample suspected of containing one or more exosomes onto a nano-plasmonic sensor of any one of paragraphs 1 to 26 under conditions which promote binding of the exosomes to the sensor;
b) washing the sensor to remove unbound materials;
c) illuminating the sensor to thereby transmit light through the sensor;
d) measuring the light transmitted through the sensor to identify a significant change from that of a negative control; and
e) detecting exosomes in the sample when the significant change in the transmitted light is identified.

37. The method of paragraph 36, wherein the negative control is a solution substantially free of exosomes or exosome lysates.

38. The method of paragraph 36 or 37, wherein the difference is a shift in peak wavelength.

39. The method of paragraph 36 or 37, wherein the difference is an intensity change at a fixed wavelength.

40. The method of any one of paragraphs 36 to 39, wherein the nano-plasmonic sensor is part of an imaging system of any one of paragraphs 27-35.

41. The method of any one of paragraphs 36 to 40, further comprising the step of contacting the exosomes bound to the sensor with a secondary label comprising an agent that specifically binds to an exosome marker.

42. The method of paragraph 41, wherein the secondary label comprises a metallic nanoparticle, a magnetic nanoparticle, a dielectric nanoparticle, a semiconductor nanoparticle, or a diamond nanoparticle.

43. The method of paragraph 42, wherein the metallic nanoparticle is a gold sphere or a gold star.

44. A method for determining an expression level of a target marker in a sample of exosomes, comprising:
a) detecting total exosomes in the sample by the method of any one of paragraphs 36-43, using a capture agent that specifically binds a pan-exosomal marker;
b) detecting exosomes in the sample expressing the target marker by the method of any one of paragraphs 36-43 using a capture agent that specifically binds the target marker; and
c) calculating the ratio of exosomes with the target marker to total exosomes to thereby indicate the average expression level of the target marker per exosome from the sample.

45. The method of paragraph 44, wherein the pan-exosomal marker is CD63.

46. The method of paragraph 44 or 45, wherein the target marker is a cancer marker.

47. A method of detecting a disease or disorder in a subject, comprising,
a) detecting an expression level of a marker of the disease or disorder by the method of any one of paragraphs 44-46;
b) comparing the expression level detected in step a) to that of a normal, healthy control; and
c) detecting the disease or disorder in the subject when an elevated exosomal expression level of the marker of the disease or disorder is identified.

48. A method of monitoring treatment efficacy of a disease or disorder comprising periodically determining an expression level of a target marker associated with the disease or disorder in a sample of exosomes by the method of any one of paragraphs 44-46, wherein a reduction in the expression level over time indicates treatment efficacy.

49. The method of paragraph 47 or 48, wherein the disease or disorder is cancer.

50. The method of paragraph 49, wherein the cancer is ovarian cancer and the marker is of the cancer is selected from the group consisting of EpCAM, CD24, CA19-9, Claudin3, CA-125, MUC18, EGFR, and combinations thereof.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to describe the present invention, in connection with percentages means±1%, or ±5%. For example, about 100 means from 95 to 105.

In one respect, the present invention relates to the herein described compositions, methods, and respective component (s) thereof, as essential to the invention, yet open to the inclusion of unspecified elements, essential or not ("comprising"). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The technology disclosed herein is further illustrated by the following examples which in no way should be construed as being further limiting.

EXAMPLES

Figure 2B:
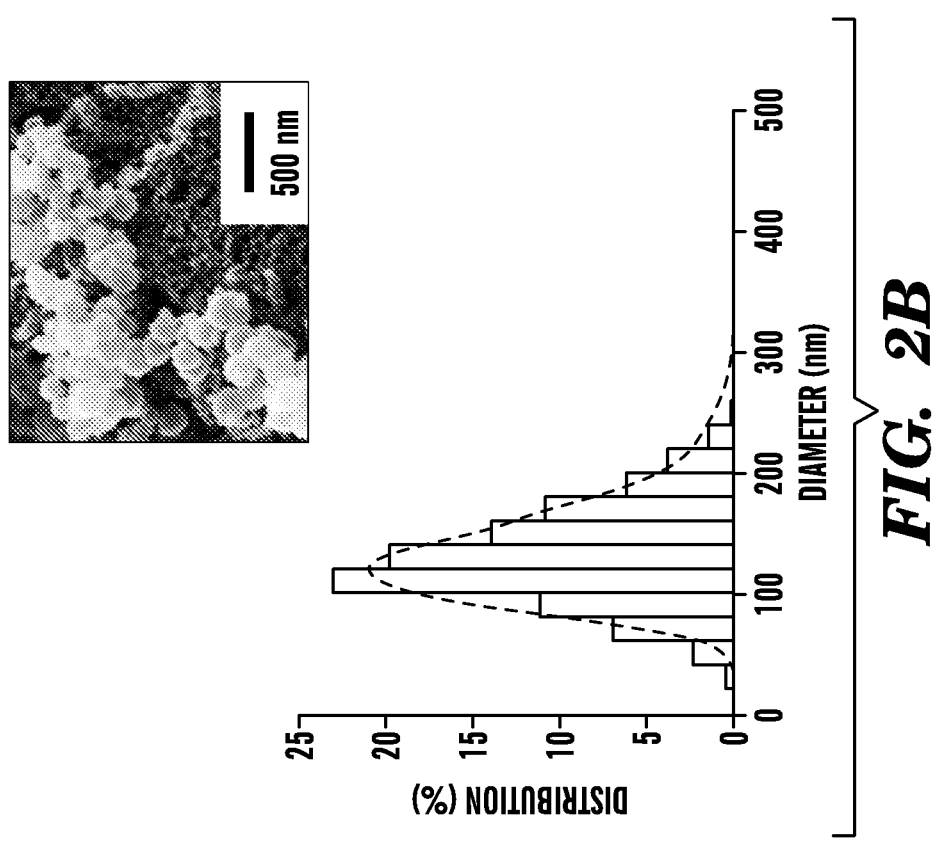
FIG. 2A-FIG. 2B indicate that exosomes shed from cancer cells.
Figure 2A:
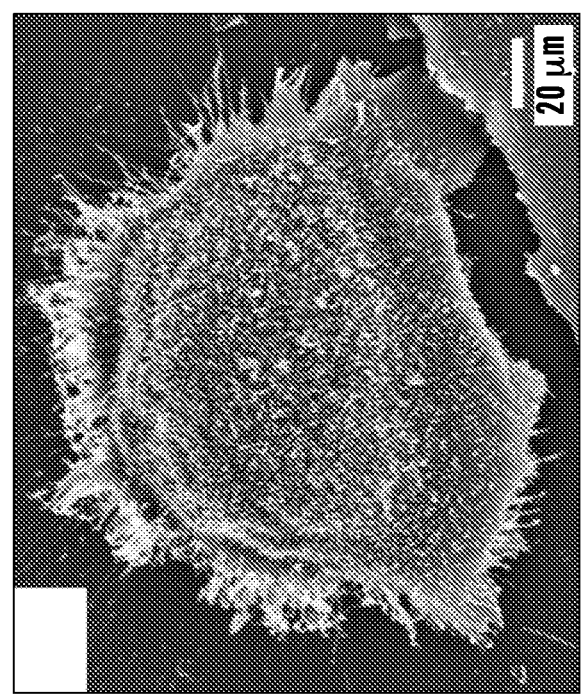

Example 1: Nano-Plasmonic Sensor for Label-Free Detection and Molecular Profiling of Exosomes nPLEX Sensor for Label-Free Exosome Detection Large quantities of exosomes are actively secreted by cancer cells through endocytotic processes and circulate in various biofluids (FIG. 1A and FIG. 2A). Nanoparticle tracking analysis (NTA) indicated that exosomes have a unimodal size distribution with an average diameter of 100 nm (FIG. 2B). The nPLEX sensor was designed to achieve label-free detection of such nanoscale vesicles. The basic sensing unit consisted of a periodic lattice of nanoapertures patterned in a metal film. Simulation studies revealed enhanced electromagnetic fields that were tightly confined within exosome size range (FIG. 1B). The field range was further tuned by adjusting the nanoaperture periodicity, thereby maximizing the detection sensitivity (FIG. 3B). In one embodiment, a working design had a rectangular lattice of nanoapertures (200 nm in diameter) with a periodicity of 450 nm; the structure was patterned in a 200 nm-thick Au film on a glass substrate (FIG. 1C). For high-throughput analyses, a 12×3 array of sensing units was laid out with multi-channel microfluidics placed on top (FIG. 4A-FIG. 4C). Each channel spanned over three sensing units for triplicate measurements. The sample volume per sensing unit was ~1 nL, and the volume of each channel reservoir was 10 µL.

Figures 5C, 5D:
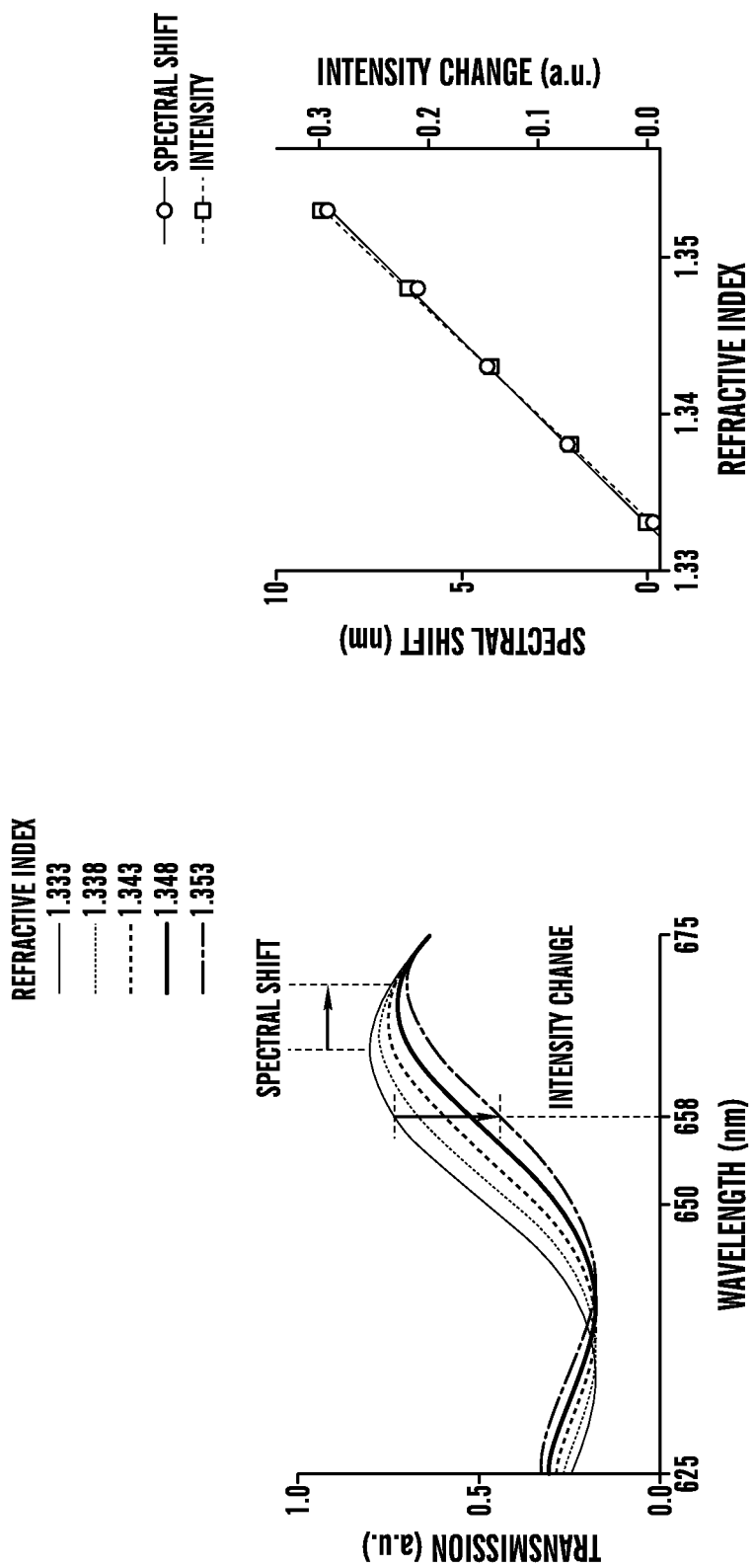

Unlike conventional reflection-based SPR devices, the nPLEX sensor operated in a transmission mode. This scheme made it possible to use a compact collinear optical setup and construct densely packed sensing units (FIG. 5B). Specific binding of exosomes to the nPLEX sensor changed its local refractive index, which can be monitored by measuring either 1) wavelength shifts ($\Delta\lambda$) in light spectrum (spectral detection) or 2) intensity changes (Op) at fixed wavelength (intensity detection; FIG. 5C) (Im, H., et al., Anal. Chem. 2009, 81, 2854-2859; Yanik, A. A. et al., Proc Natl Acad Sci USA 2011, 108, 11784-11789). Spectral detection was employed for assay development and optimization. For clinical applications, the intensity detection scheme was adopted and a portable imaging system was implemented (FIG. 1D). Consisting of a laser-diode and a complementary metal-oxide-semiconductor (CMOS) imager, the system offered a large field-of-view (~25 mm$^2$). The entire nPLEX array (36 sensing units) was imaged simultaneously for parallel detection.

Figure 1F:
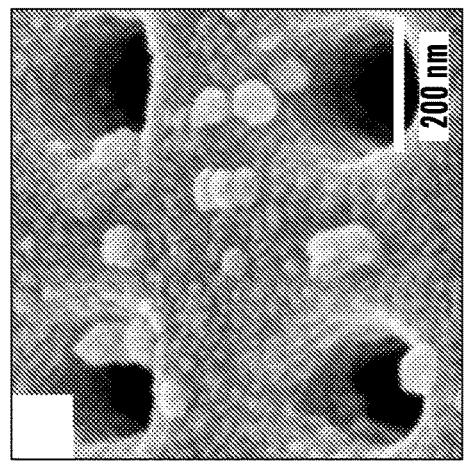

To functionalize the SPR surface, a multi-step approach was used. Pre-coating the device surface with a 1:3 mixture of long (MW 1 kDa) and short (200 Da) polyethylene glycol (PEG) polymers minimized non-specific exosome binding (FIG. 6A-FIG. 6B) and improved surface hydrophilicity. Following PEG-coating, monoclonal antibodies were grafted onto the long PEG chains for specific exosome binding. All surface modifications were done by flowing reagents through the microfluidic channels while monitoring binding by tracking the spectral shifts (FIG. 1E). The functionalized nPLEX chip showed high specificity for exosome capture (FIG. 7A-FIG. 7C), which was also confirmed by electron microscopy (FIG. 1F). Parallel detection of 12 target exosomal markers could be accomplished in <30 min. Furthermore, the sensor could be regenerated for repeated use, e.g., by eluting attached antibodies and exosomes (FIG. 8).

Detection Sensitivity

Figure 9C:
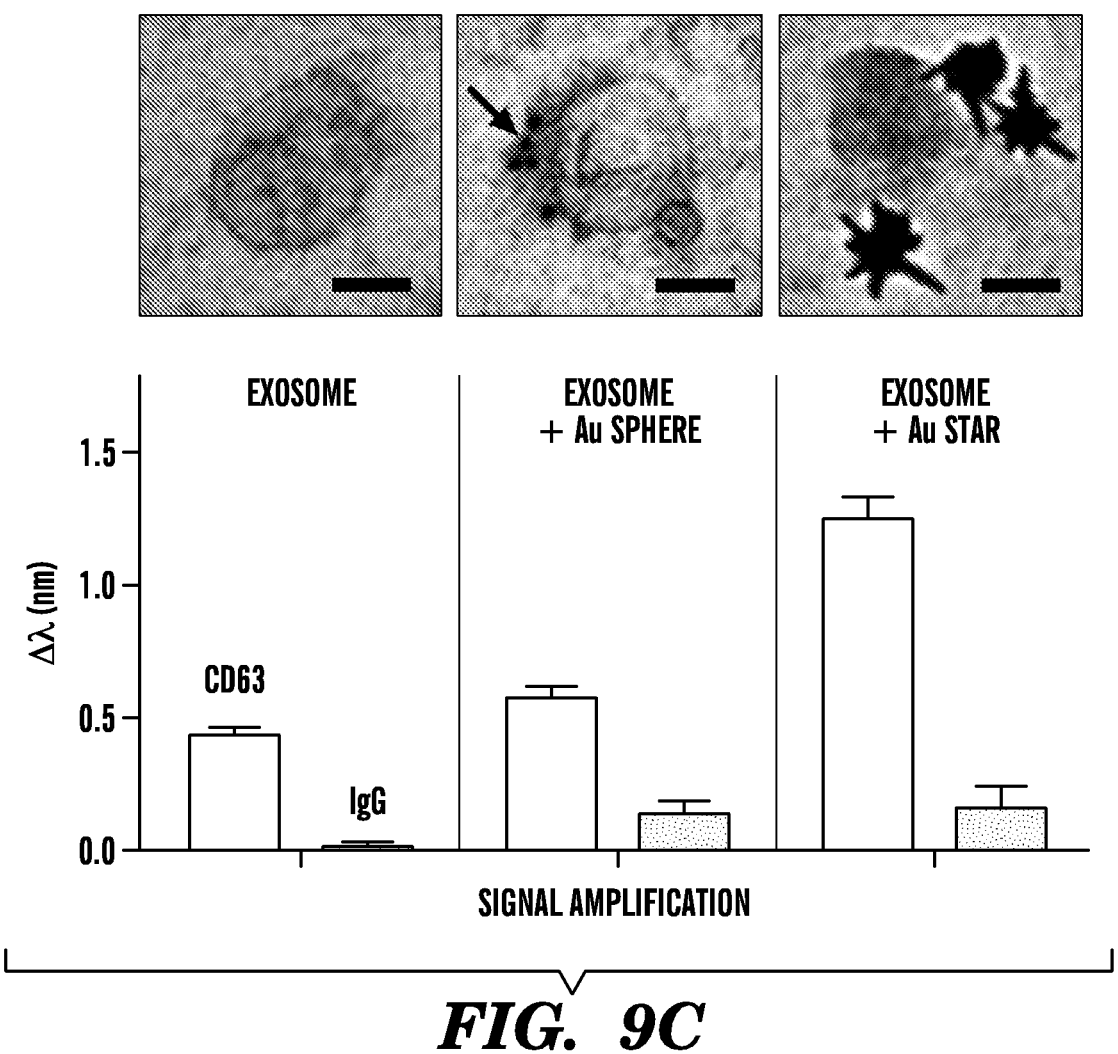
Figure 10A:
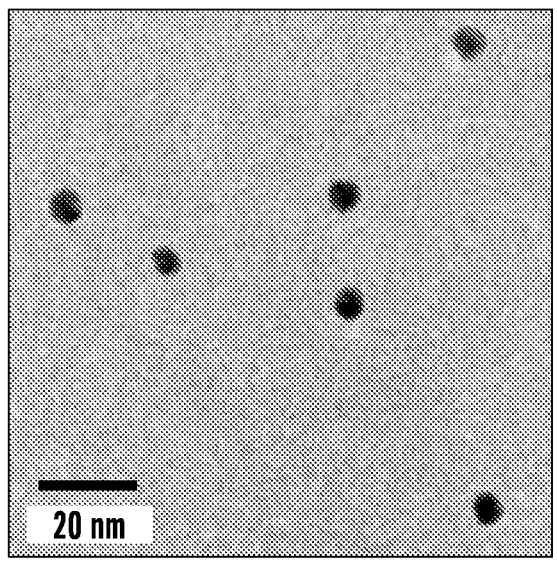
FIG. 10A-FIG. 10B are SEM images of Au nanoparticles for signal amplification. Au nanospheres (diameter, 10 nm.
Figure 10B:
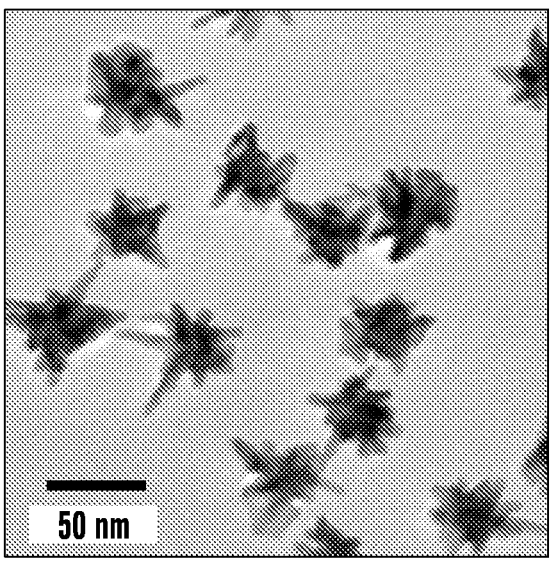

An assay protocol was established for quantitative exosome analyses. First, the nPLEX array was used to examine exosome binding kinetics. The sensor surface was functionalized with antibodies against CD63, a type III lysosomal membrane protein abundant and characteristic in exosomes (Shao, H. et al., Nat. Med. 2012, 18, 1835-1840). A sensogram was measured by introducing exosomes derived from human ovarian cancer cell (CaOV3) culture (FIG. 9A). The observed binding constant was ~36 pM, which was significantly lower than that of individual antibodies (~1 nM). Such stable binding could be attributed to the multivalent nature of the nPLEX assay (i.e., multiple antibody binding per exosome) (Tassa, C. et al. Bioconjug. Chem. 2009, 21, 14-19). The detection sensitivity of the nPLEX assay was next determined. Exosomes were isolated from CaOV3 culture, and their initial concentrations were estimated by NTA. A pair of nPLEX sensors, functionalized with CD63 and control antibodies respectively, were used to measure the relative spectral shifts ($\Delta\lambda^{CD63}$) against known exosome counts. The titration experiments established the limit of detection (LOD) of ~3000 exosomes (670 aM) with the label-free nPLEX assay (FIG. 9B). The observed sensitivity was 104- and 102-fold higher than western blotting and chemiluminescence ELISA, respectively (FIG. 9B). The nPLEX platform also facilitated signal amplification through a secondary labeling (FIG. 9C). For instance, when captured exosomes were targeted with spherical Au nanoparticles (diameter, 10 nm), the signal ($\Delta\lambda^{CD63}$) improved by 20%. Using star-shaped Au nanoparticles, the signal was enhanced even further by 300%, as the branched arms in the star-shaped particles effectively concentrated electromagnetic fields near the sensor surface (FIG. 10A-FIG. 10B).

Protein Profiling on Exosomes.

Figure 9D:
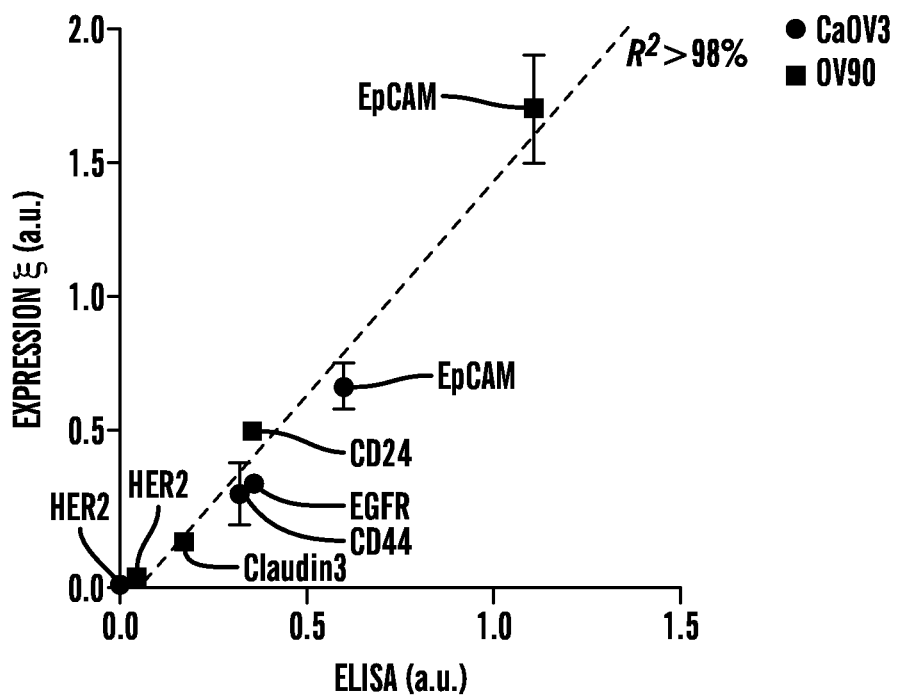
Figure 11A:
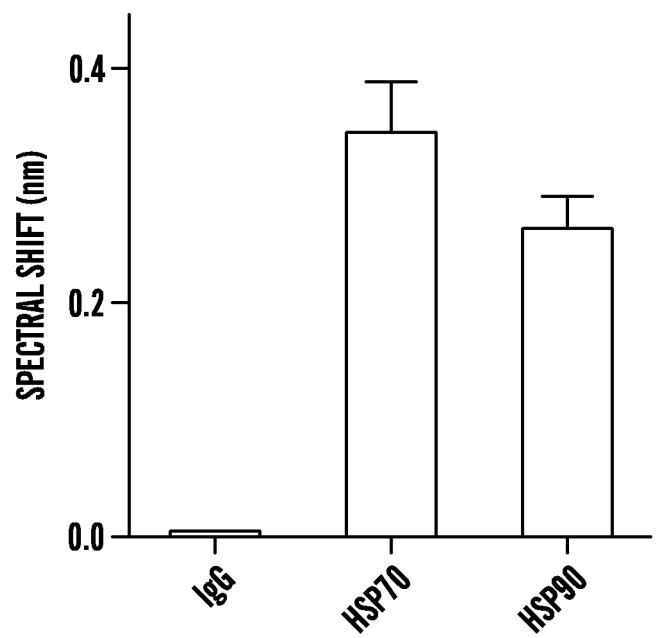
FIG. 11A-FIG. 11B demonstrate that nPLEX can be used as assays for intravesicular protein markers. For the detection of intravesicular markers, exosomes were lysed, and the lysates were introduced onto the nPLEX sensor. The sensor had sensing arrays that were separately conjugated with isotype-matched IgG, heat-shock protein (HSP) 70 or HSP90 antibodies. The results from the nPLEX analyses (FIG. 11A) qualitatively matched with western blotting data (FIG. 11B), indicating the relative high abundance of HSP70 over HSP90.
Figure 11B:
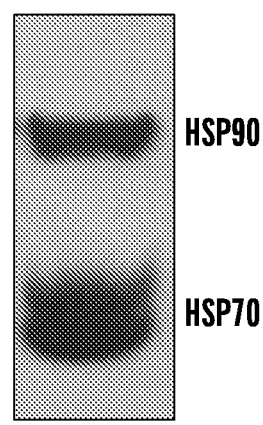

To quantitatively detect exosome proteins, the nPLEX sensors were functionalized with antibodies against target markers and measured the associated spectral shifts ($\Delta\lambda^{target}$) or intensity changes ($\Delta p^{target}$). Next, the expression level ($\xi^{target}$) of the target marker was defined by scaling the marker-associated changes to those of CD63 (i.e., $\xi^{target}=\Delta\lambda^{target}/\Delta\lambda^{CD63}=\Delta p^{target}/\Delta p^{CD63}$). Such normalization accounted for differences in exosome counts among samples and thereby reported an average expression level of a target marker per exosome. This method was applied to profile exosomes from different cell lines (CaOV3, OV90) for various extravesicular markers (FIG. 9D). Expression levels were well-matched ($R^2$>98%) between nPLEX and ELISA, verifying the accuracy of the developed nPLEX assay. Yet the nPLEX label-free detection was faster, more sensitive and required smaller sample amounts than ELISA. The nPLEX's broad versatility was also demonstrated by directly detecting intravesicular markers in exosome lysates (FIG. 11A-FIG. 11B). Altogether, the nPLEX sensor facilitated high-throughput and comprehensive exosomal protein typing.

Exosome Protein Profiles Match Parent Cells.

Figure 12B:
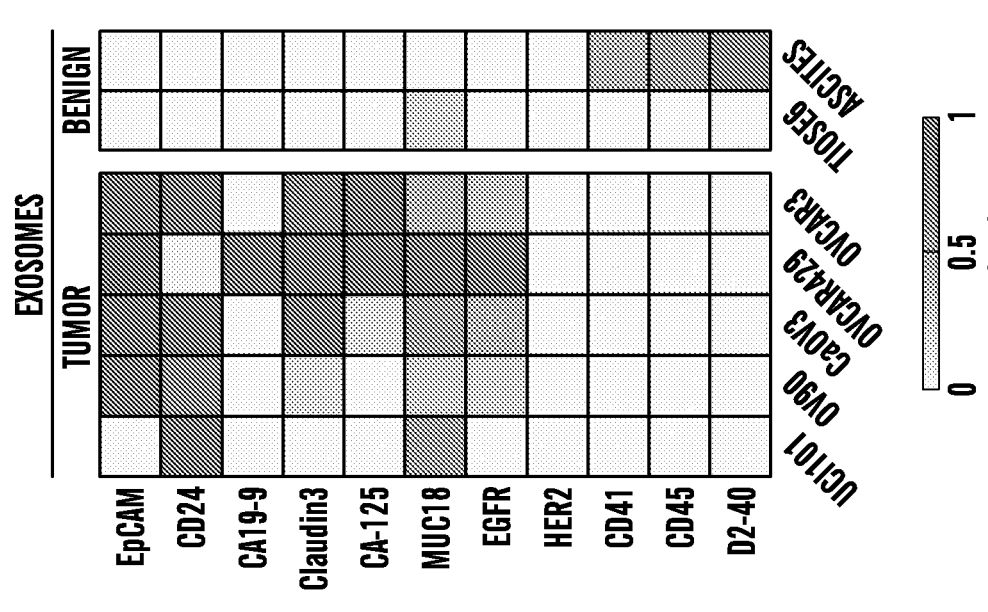
FIG. 12A-FIG. 12B indicate molecular signature of ovarian cancer exosomes. Ovarian cancer markers (EpCAM, CD24, CA19-9, Claudin3, CA-125, MUC18, EGFR, HER2), immune host cell markers (CD41, CD45) and a mesothelial marker (D2-40) were profiled on both parental ovarian cells (FIG. 12A, using flow cytometry) and their derived exosomes (FIG. 12B, using nPLEX sensor). Exosomal protein profiles indicated an excellent match with those of originating cells (Pearson coefficient>0.95). A two-marker combination comprising EpCAM and CD24 could effectively distinguish cancer exosomes from benign exosomes. MFI, mean fluorescence intensity.
Figure 12A:
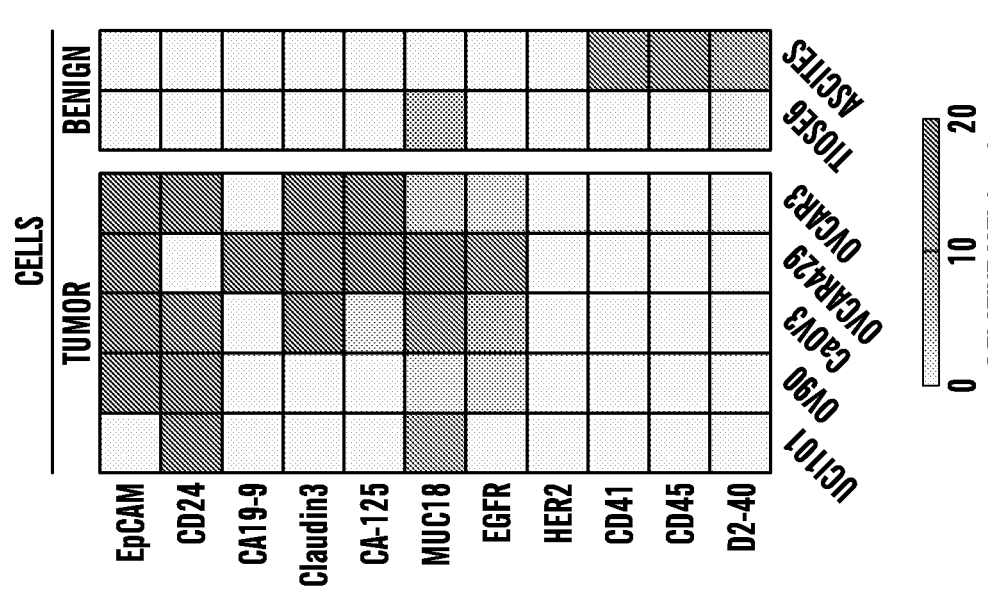

Next, the nPLEX assay was used to molecularly screen exosomes across different ovarian cancer cell lines. The focus was on 1) examining how closely exosomes reflect their cells of origin and 2) determining a distinct molecular signature of ovarian-cancer exosomes. Based on published studies, the following ovarian cancer markers were selected: epithelial cell adhesion molecule (EpCAM) (Runz, S. et al., Gynecol. Oncol. 2007, 107, 563-571; Taylor, D. D. & Gercel-Taylor, C., Gynecol. Oncol. 2008, 110, 13-21), CD24 (Runz, S. et al., Gynecol. Oncol. 2007, 107, 563-571; Kristiansen, G. et al., The American journal of pathology 2002, 161, 1215-1221), cancer antigen 19-9 (CA19-9) (Canney, P. A., et al., Br. J. Cancer 1985, 52, 131; Rosen, D. G. et al., Gynecol. Oncol. 2005, 99, 267-277), claudin 3 (Rosen, D. G. et al., Gynecol. Oncol. 2005, 99, 267-277; Li, J. et al., BMC cancer 2009, 9, 244), cancer antigen 125 (CA-125) (Bast Jr, R. C. et al., The International journal of biological markers 1997, 13, 179-187), MUC18 (Aldovini, D. et al., Int. J. Cancer 2006, 119, 1920-1926), epidermal growth factor receptor (EGFR) (Psyrri, A. et al., Clinical Cancer Research 2005, 11, 8637-8643), human epidermal growth factor receptor 2 (HER2) (Meden, H. & Kuhn, W., European Journal of Obstetrics & Gynecology and reproductive biology 1997, 71, 173-179); and the following host markers: CD41 (platelet), CD45 (leukocyte), D2-40 (mesothelial cells) (Chu, A. Y., et al, Modern pathology 2004, 18, 105-110). A panel of cell lines was screened for 1) the above-mentioned markers, using flow cytometry (FIG. 12A), and 2) cell-derived exosomes, using nPLEX sensors (FIG. 12B). Comparative analyses showed excellent correlation (Pearson coefficient>0.95) between the cellular and exosomal protein profiles, supporting the use of exosomes as surrogates for their originating cells. Equally importantly, elevated expression of EpCAM and CD24 markers were observed to readily distinguish ovarian cancer exosomes from host-derived vesicles.

Clinically Applying the nPLEX Platform to Ovarian Cancer Detection.

Figure 13A:
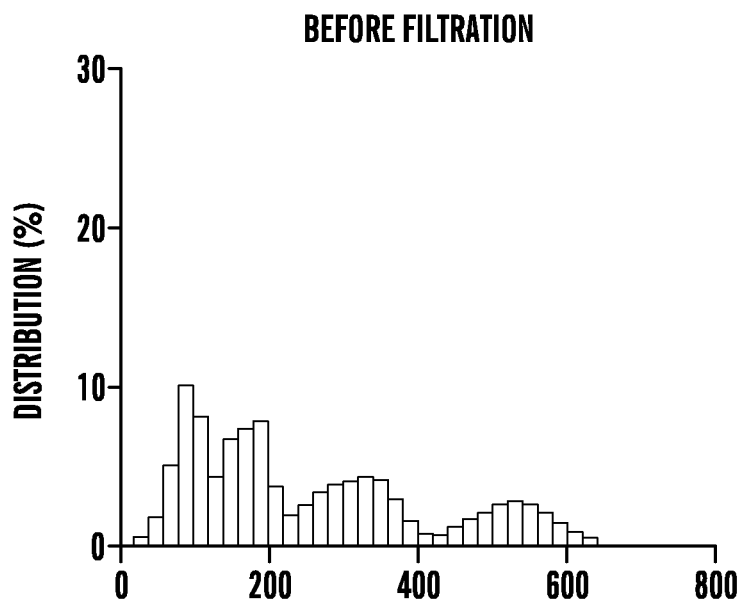
FIG. 13A-FIG. 13C demonstrate preparation of exosomes from filtration. Size distribution of a clinical ascites sample, before (FIG. 13A) and after (FIG. 13B) filtration step to remove large cellular and vesicular debris. A membrane filter with 0.2 μm size cutoff was used. Post filtration, a single size peak at ~100 nm vesicular diameter was observed.
Figure 13B:
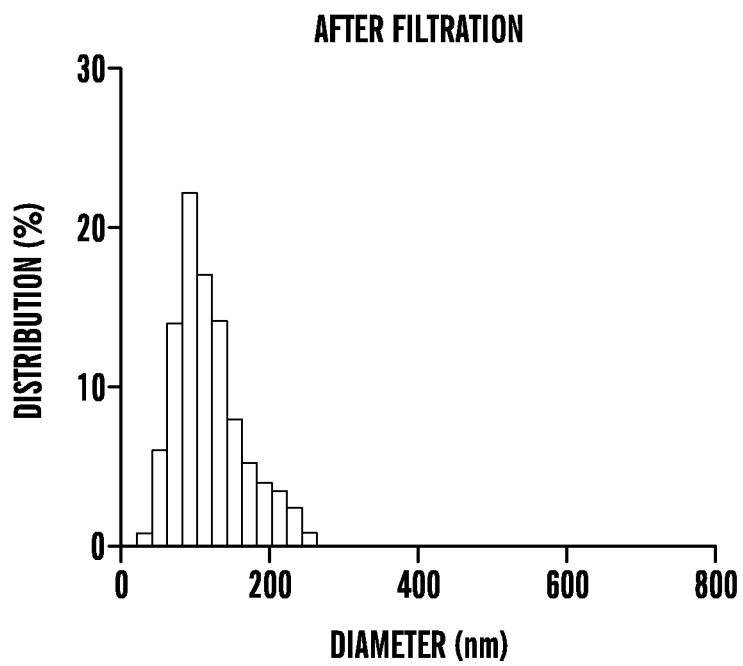
Figure 13C:
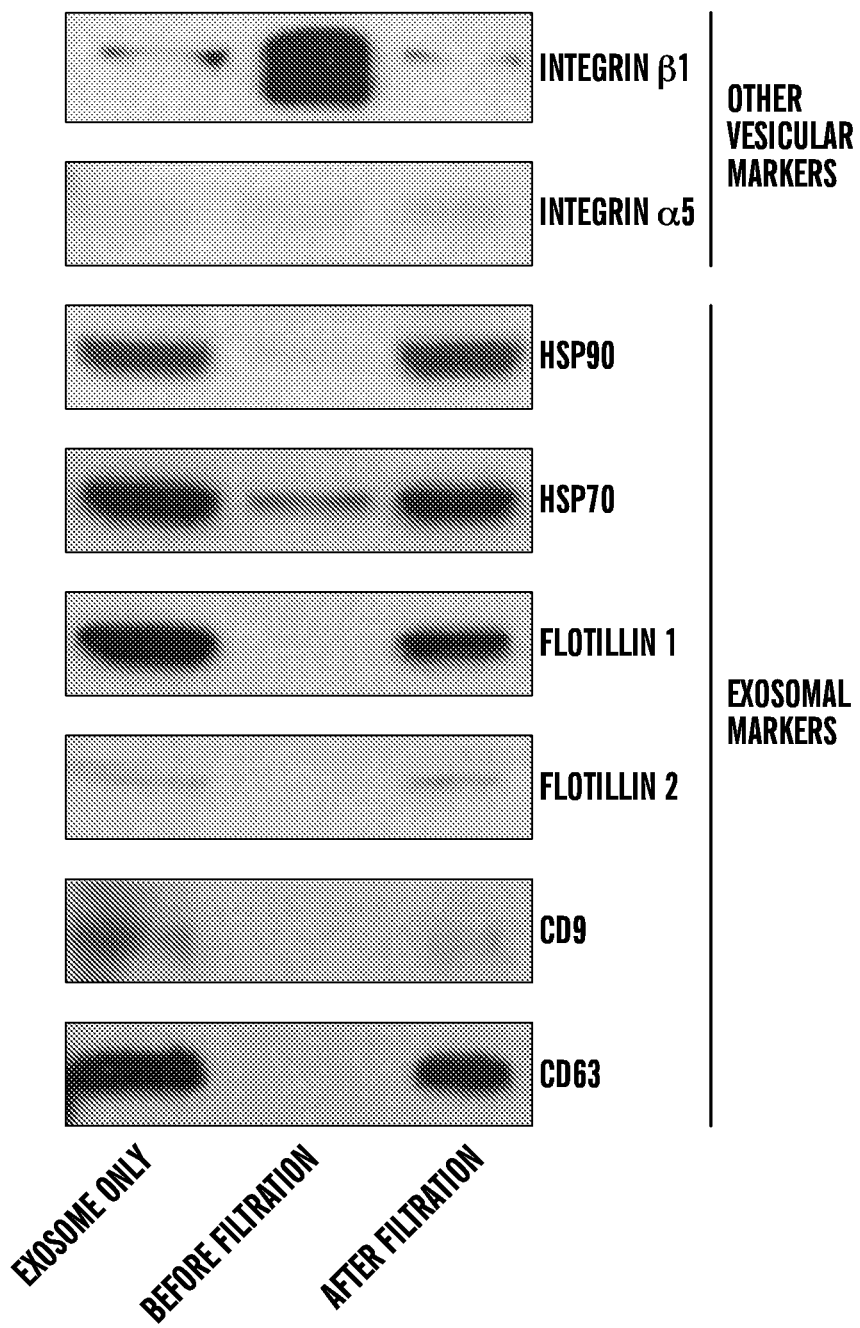

The nPLEX platform was then applied to detect exosomes in patient-derived ovarian cancer ascites (i.e., excess fluid accumulation in the peritoneal cavity (Kipps, E., et al., Nat. Rev. Cancer 2013, 13, 273-282)). Ascites is common in ovarian cancer patients and is often tapped for symptomatic relief; it was hypothesized that the fluid, which is commonly discarded, would contain exosomes and thus allow molecular diagnostics (Kipps, E., et al., Nat. Rev. Cancer 2013, 13, 273-282; Andre, F. et al., The Lancet 2002, 360, 295-305). Native ascites samples were found to indeed contain large quantities of exosomes (>$10^9$ per mL) sufficient for robust nPLEX detection without the need for further enrichment or signal amplification. As such, samples were assayed directly after collecting exosomes through a single filtration step; both size and western blotting analyses confirmed exosome enrichment after filtration (FIG. 13A-FIG. 13C).

Figure 14A:
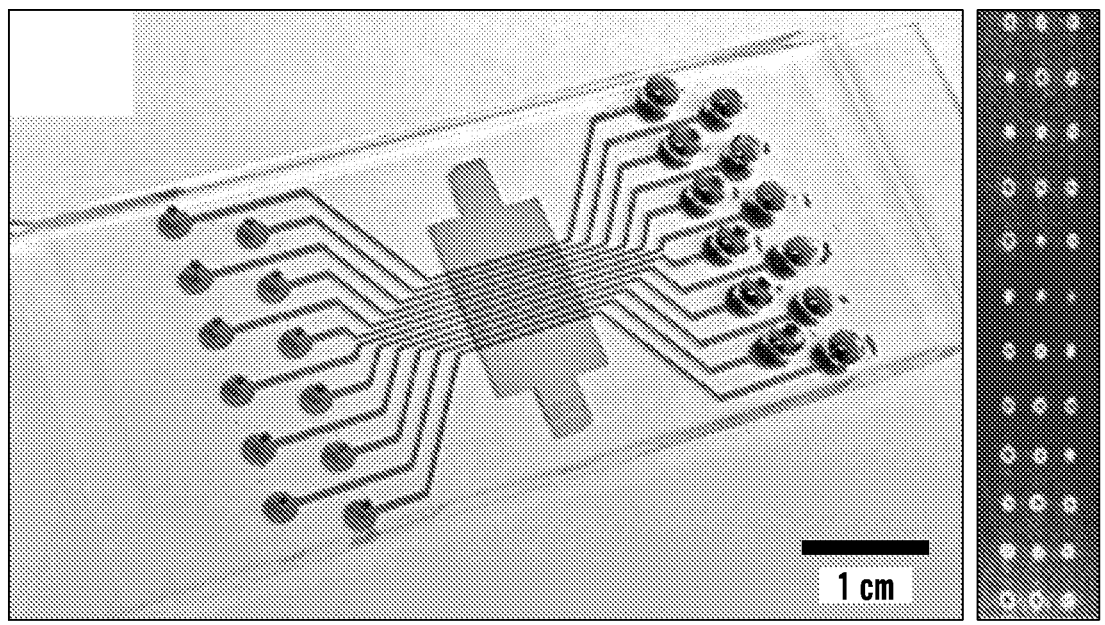
FIG. 14A-FIG. 14D demonstrate miniaturized nPLEX imager system for point-of-care analysis of patient samples.
Figure 14B:
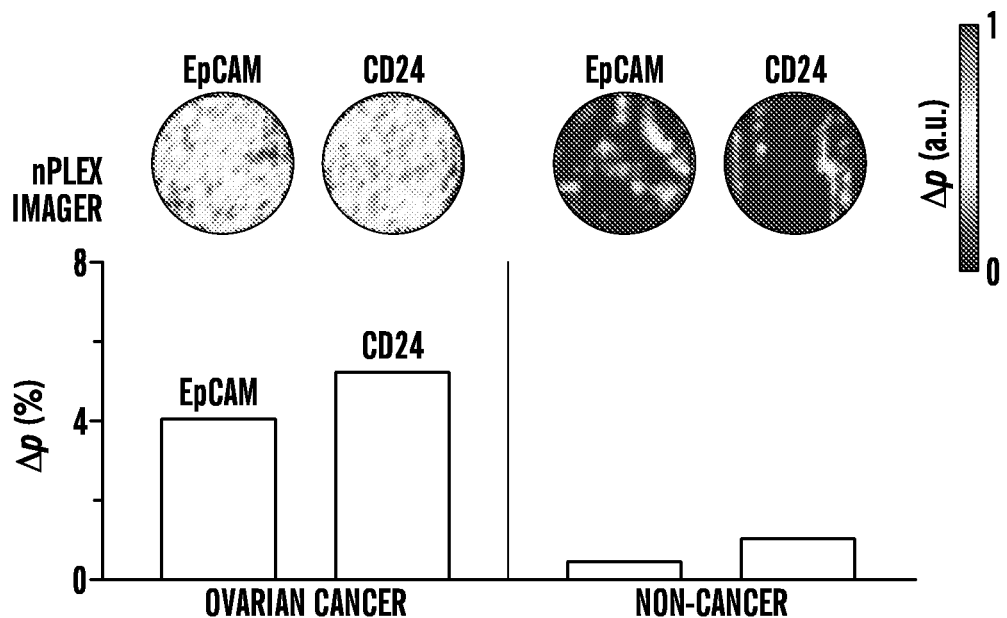
Figure 15:
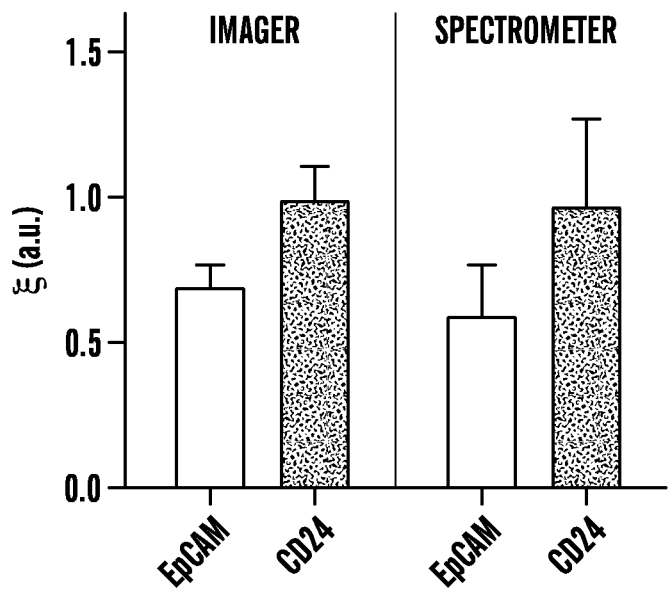
FIG. 15 is a graph of experimental results that demonstrates the comparison between intensity and spectrum measurements. Exosomal expression levels of EpCAM and CD24 measured by the portable nPLEX imager system were compared with those measured by the spectrometer setup with a microscope. The results indicated an excellent agreement.

The 12-channel nPLEX array was used, with each channel functionalized for different markers (EpCAM, CD24, CD63, IgG control), and the entire 12×3 array was imaged using the portable imager system (FIG. 14A and FIG. 5B). After measuring the diffracted light emitted through the nPLEX sensor, the light intensity at the sensor surface was numerically reconstructed. FIG. 14B shows a representative example. With a malignant specimen, the EpCAM and CD24 arrays displayed significant ($P<0.05$) intensity changes ($\Delta p$) due to cancer exosome capture; changes were negligible with a non-cancer ascites sample. Furthermore, the exosomal expression levels of target markers, as measured by the imager, matched with those by spectral detection (FIG. 15).

Figure 14C:
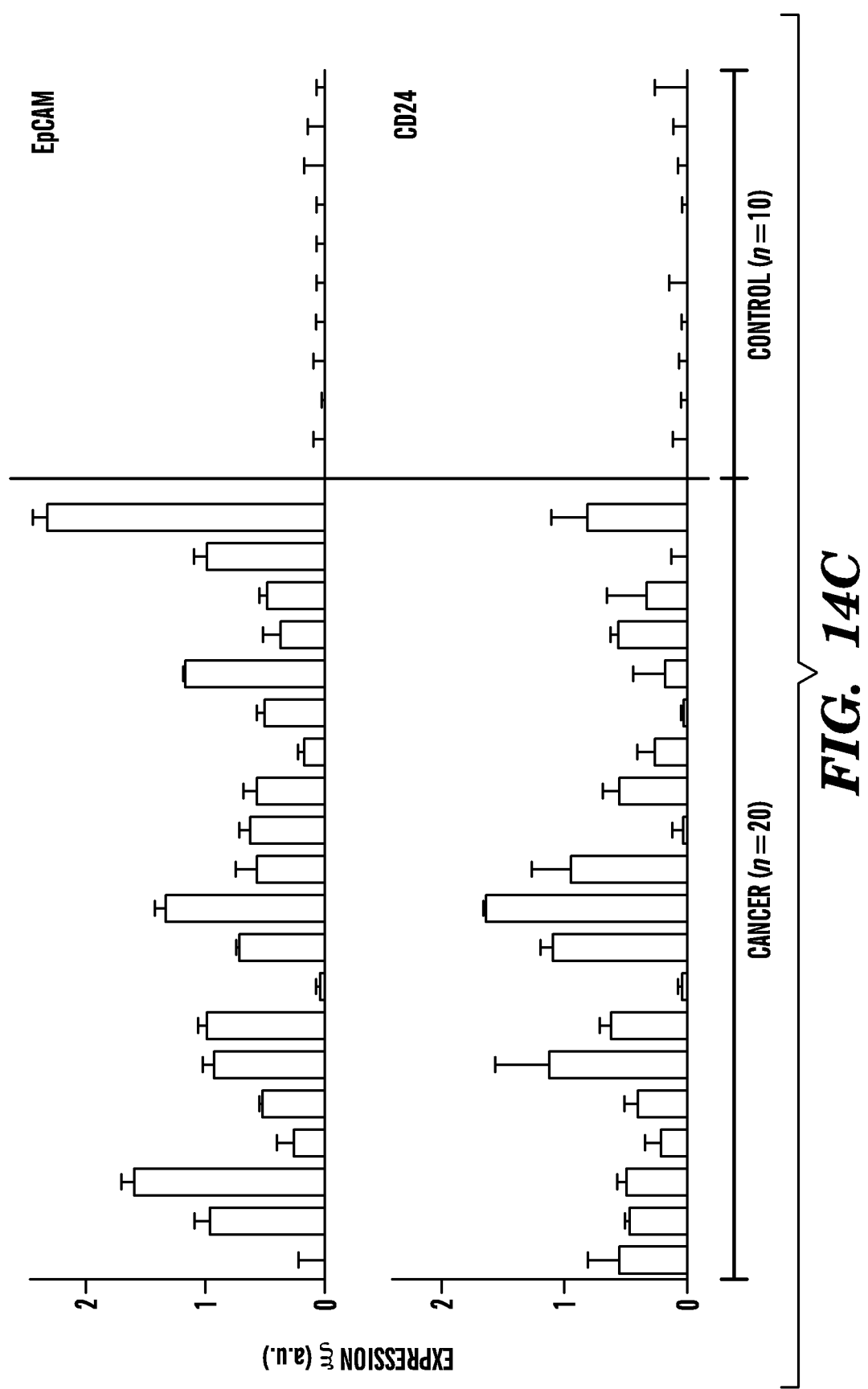
Figure 16:
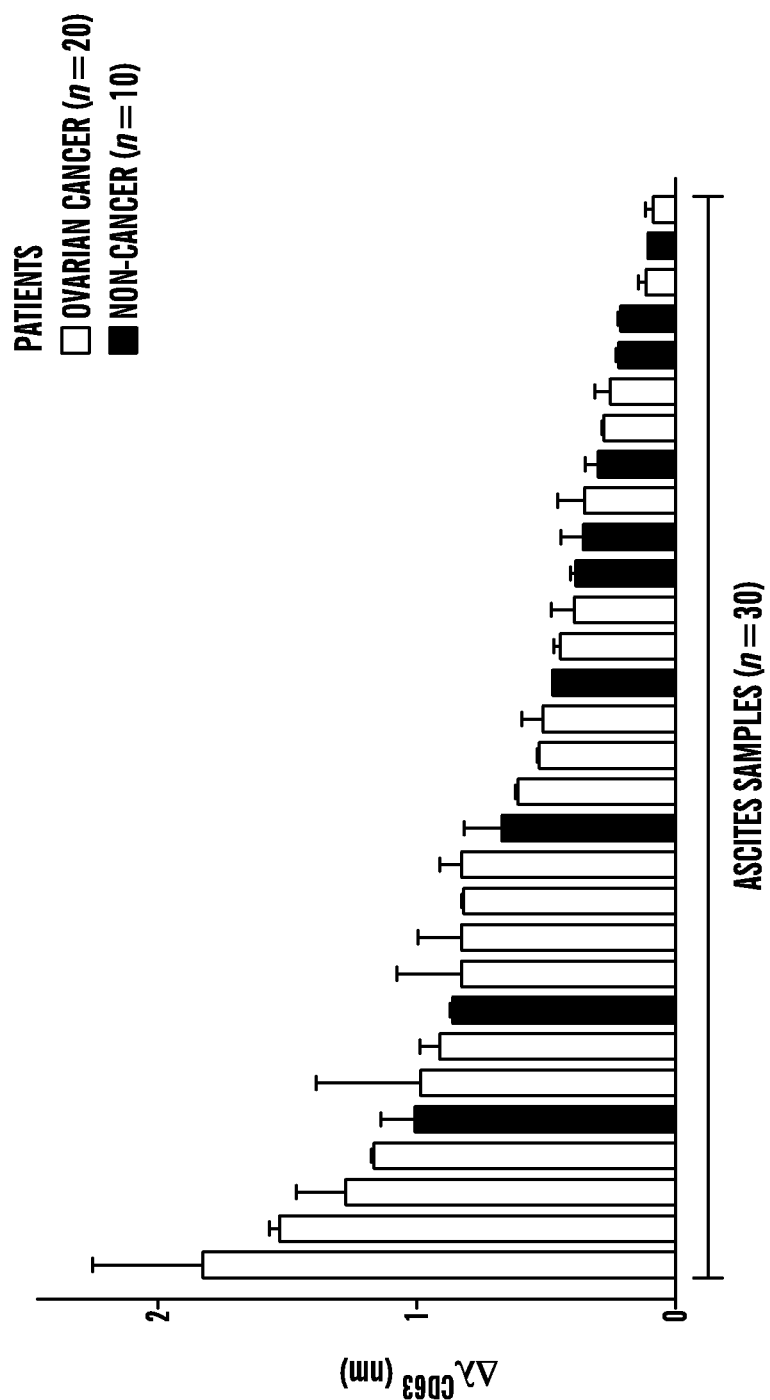
FIG. 16 is a graph of experimental results that demonstrate the heterogeneity of exosome concentration in patient ascites samples. Exosome concentration was determined in native clinical ascites (n=30) with the nPLEX platform, based on their CD63 spectral shifts ($\Delta\lambda^{CD63}$), and sorted from high to low. Both ovarian cancer ascites and non-cancer ascites samples present a high degree of heterogeneity in exosome concentration with a significant overlap. The data is displayed as mean±s.e.m from triplicate measurements.

The assay was extended to include samples from ovarian cancer patients (n=20) and, as controls, non-cancerous ascites from patients with cirrhosis or heart failure (n=10) (Table 1). Exosome concentrations estimated by nPLEX, using CD63 signal changes, were highly heterogenous among patient and control samples (FIG. 16) and could not conclusively differentiate between cancer patients and control subjects; it is likely that exosome numbers were highly susceptible to sampling variations (e.g., ascitic drainage procedure). Yet exosomal EpCAM and CD24 expression levels were upregulated in ovarian cancer patients, whereas their levels were negligible in control samples (FIG. 14C). Pairing expression profiles of EpCAM and CD24 consequently produced high diagnostic accuracy (96%).

TABLE 1

Clinical information of patients

| Characteristic | Molecular profile Number (%) | Longitudinal Cohort Number (%) |
|---|---|---|
| Non Cancer Ascites | 10 | — |
| Ovarian Cancer | 20 | 8 |
| Age | | |
| Median | 60 | 60 |
| Range | 36-85 | 50-85 |
| Histology | | |
| Serous | 16 (80%) | 5 (62.5%) |
| Mucinous | 1 (5%) | 1 (12.5%) |

TABLE 1-continued

Clinical information of patients

| Characteristic | Molecular profile Number (%) | Longitudinal Cohort Number (%) |
|---|---|---|
| Mixed | 1 (5%) | 1 (12.5%) |
| Poorly Differentiated | 2 (10%) | 1 (12.5%) |
| Stage | | |
| IIIC | 10 (50%) | 5 (62.5%) |
| IV | 10 (50%) | 3 (37.5%) |
| Surgical Debulking | | |
| Optimal | 9 (45%) | 4 (50%) |
| Suboptimal | 2 (10%) | 1 (12.5%) |
| Interval | 8 (40%) | 3 (37.5%) |
| None | 1 (5%) | 0 |
| Platinum Response | | |
| Sensitive | 5 (25%) | 2 (25%) |
| Resistant | 14 (70%) | 5 (62.5%) |
| Refractory | 1 (5%) | 1 (12.5%) |
| Clinical Trajectory | | |
| Response | 3 (15%) | 4 (50%) |
| Stable | 1 (5%) | 0 |
| Mixed | 2 (10%) | 0 |
| Progression | 14 (70%) | 4 (50%) |

Figure 14D:
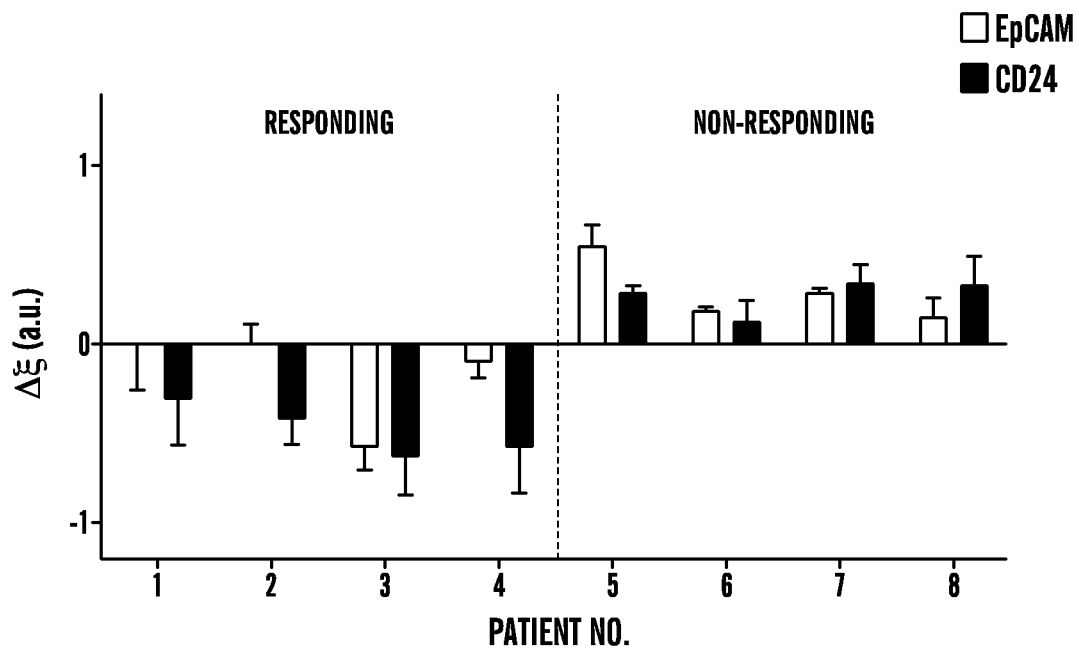

Next, the nPLEX assay was used to evaluate prognostic values of exosomes for treatment monitoring. Ovarian cancer patients undergoing standard chemotherapy were recruited (n=8; Table 1), and their ascites samples were collected before and after treatment. For both time points, the exosomal EpCAM and CD24 expression levels were monitored. A board-certified oncologist (C.M.C.), blind to nPLEX data, assigned each subject either responder or non-responder status based on clinical, laboratory and radiologic outcomes. In this longitudinal subset, the exosomal EpCAM and CD24 expressions displayed distinct temporal changes. Notably, the levels of EpCAM, CD24 or both decreased among responding patients, whereas non-responding patients were associated with either stationary or increased marker expression (FIG. 14D).

Figure 17A:
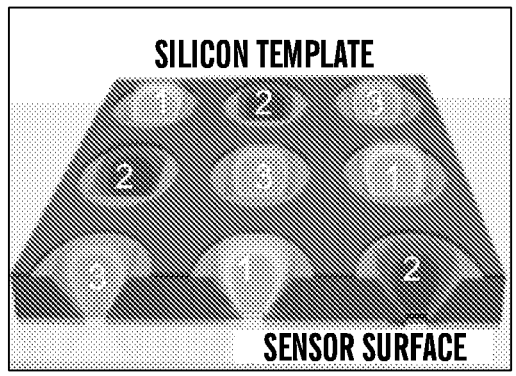
FIG. 17A-FIG. 17C illustrate reusable template for molecular printing on nPLEX sensor. A molecular printing template was fabricated by anisotropically etching a (100) Si wafer (FIG. 17A). While one side of the template had wide window (~1 mm×1 mm) for applying solutions by pipetting or spot-printing, the other side had much confined openings (250 μm×250 μm) for local delivery of agents to the sensor surface (FIG. 17B).
Figure 17B:
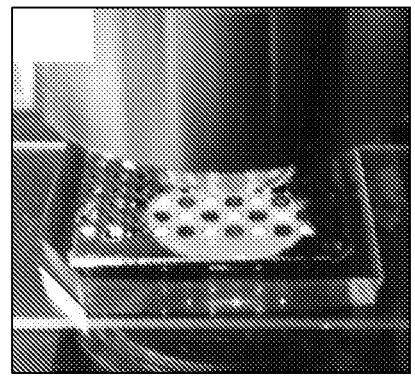
Figure 17C:
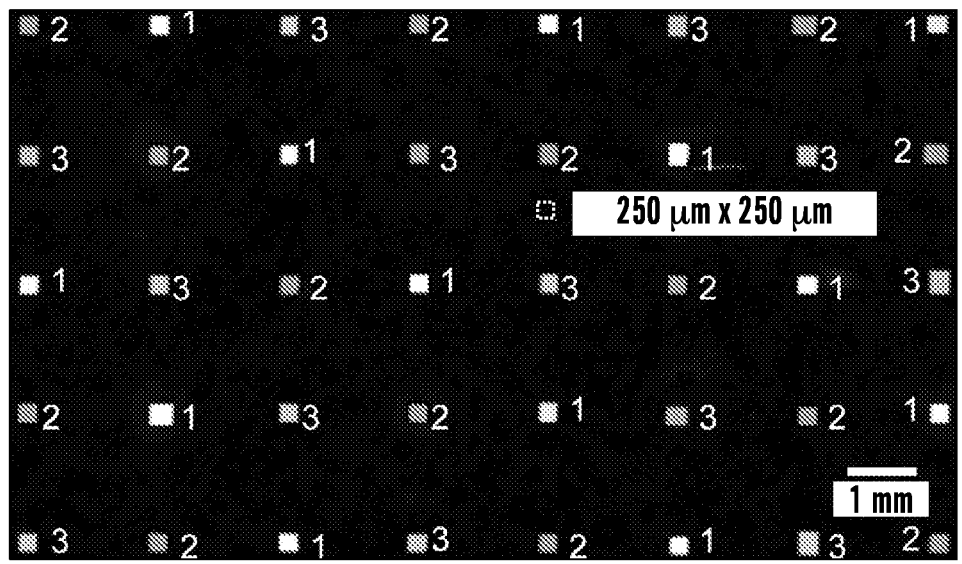
Figure 18:
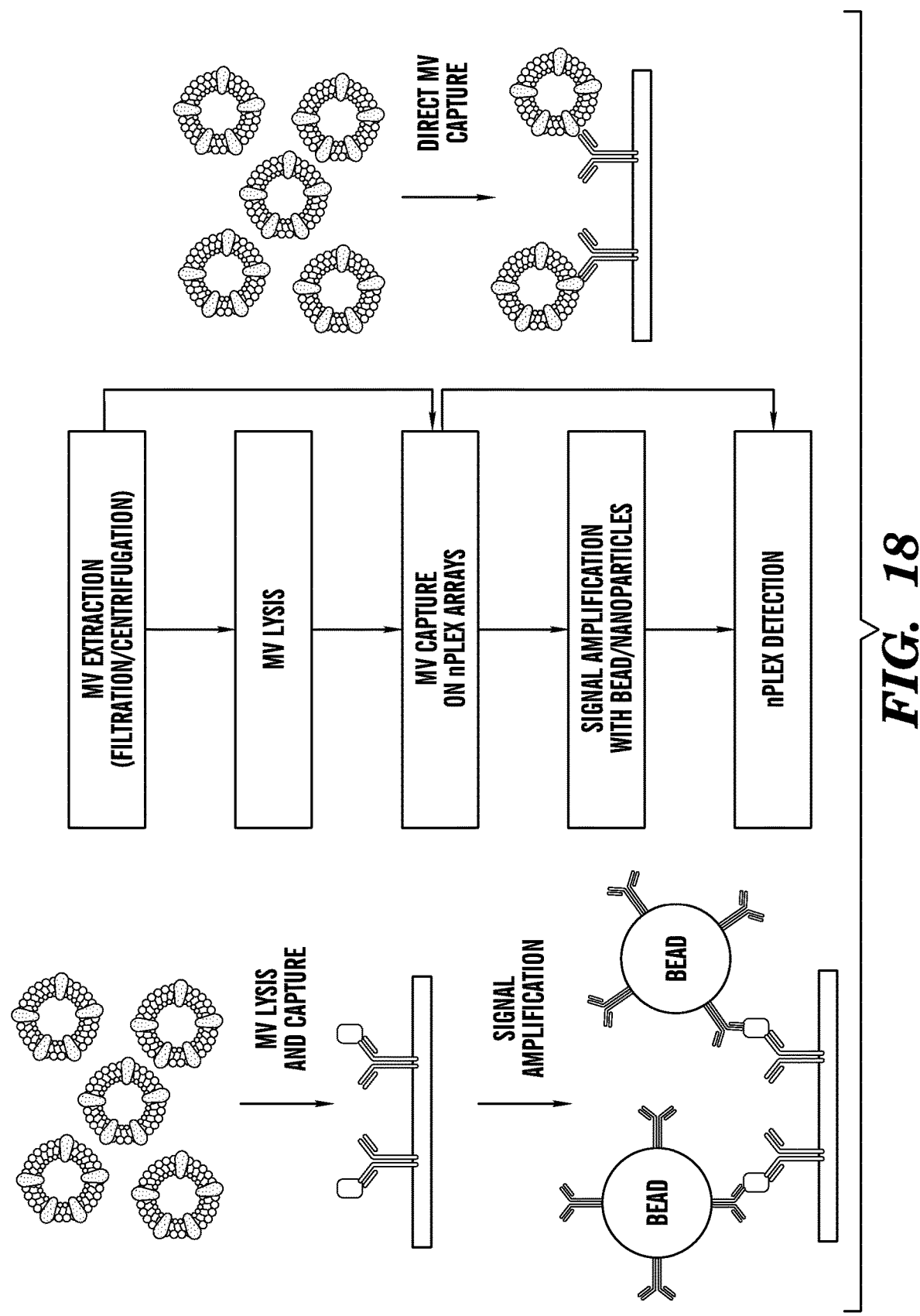
FIG. 18 is a detection scheme for extravesicular or intravesicular markers. Extravesicular markers can be detected by capturing intact exosomes through antibodies immobilized on the nPLEX surface (right side). For intravesicular markers, exosomes can be lysed and target proteins are captured on the nPLEX surface by capture antibodies. Then, nanoparticles (beads) coated with probe antibodies binds to the captured intravesicular proteins, amplifying the nPLEX signal.

To expand nPLEX diagnostics and accelerate their clinical translation, a new template-stripping lithography (Nagpal, P., et al., Science 2009, 325, 594-597; Im, H. et al., ACS Nano 2011, 5, 6244-6253) and the molecular printing method can be adopted (FIG. 17A-FIG. 17C) (MacBeath, G. & Schreiber, S. L. Science 2000, 289, 1760-1763) for rapid, scale-up chip fabrication.

Materials and Methods nPLEX Chip Fabrication.

Standard microscope glass slides were cleaned in a piranha solution (3:1 $H_2SO_4$:$H_2O_2$) at 80° C. for 30 min and rinsed with distilled water. The glass slides were then dried under $N_2$ stream and baked on a hotplate at 150° C. for 15 min. A 200 nm thick Au film with a 2 nm thick Ti adhesion layer was deposited on the glass slides through electron-beam metal evaporation (Denton E-beam evaporator) at deposition rates of 2 Å/sec (Au) and 0.5 Å/sec (Ti). A patterned acrylic sheet was placed on the glass slide as a shadow mask to define a sensing area in the center of the glass slide. Periodic nanoaperture arrays, wherein each consisted of 44 by 32 apertures with 200 nm diameter and 450 nm periodicity, were fabricated by focused ion-beam milling (Zeiss NVision 40) at 30 keV and 80 pA. The nPLEX chip was integrated with a multi-channel polydimethylsiloxane (PDMS) microfluidic flow-cell fabricated by soft lithography.

Soft Lithography for a Multi-Channel Flow-Cell.

A standard soft lithography was used for the fabrication of a multi-channel flow-cell. First, a SU-8 mold was prepared on a Si wafer through standard photolithography. A SU-8 negative resist (SU-8 2050, MicroChem) was spin-coated on a Si wafer at 3500 rpm for 30 sec. The resist was then baked at 65 and 95° C. for 1 and 6 min, respectively. After being exposed under UV light, the resist was baked once again at 65 and 95° C. for 1 and 6 min, respectively. Then the wafer was immersed in SU-8 developed for 6 min with agitation. The developed wafer was then rinsed by isopropyl alcohol (IPA) and dried by nitrogen. The SU-8 mold was chemically treated by trichlorosilane vapor inside a desiccator for 30 min. Polydimethylsiloxane (PDMS), mixed with a curing agent with a 10:1 weight ratio and degassed, was casted on the SU-8 mold and cured on a hotplate at 60° C. for 3 hours. After curing, a PDMS block with multi-channel patterns was cut out from the mold, and inlets and outlets were punched by 0.5 and 2.5 mm biopsies. After cleaning the PDMS block by acetone, IPA, and distilled water, the PDMS and nPLEX chip surfaces were treated by $O_2$ plasma, bonded together, and cured on a hotplate at 70° C. for 5 min.

SPR Analysis.

Spectral peak position was measured using a custom-built Matlab code by fitting the transmission peak to a multi-order polynomial curve. The peak position was monitored and plotted in real-time upon a new input of data file. For each measurement, duplicate or triplicate arrays were measured for an error bar. A minimum detection level (0.036 nm) was determined by three times of the standard deviation of the spectral peak position measured at a steady state for 5 min. The limit of detection is then calculated by exploration of the minimum detection level to a fitted titration curve shown in FIG. 9B. For imaging measurements, the transmitted intensity at the nanoaperture was calculated by back propagation of the measured intensity profiles by applying Rayleigh-Sommerfeld diffraction theory (Mudanyali, O. et al., Lab Chip 2010, 10, 1417-1428). Then, a circular region-of-interest (ROI) was applied to calculate the intensity value of each nanoaperture array. The transmitted intensities were measured before and after exosome binding and the difference was normalized by the initial intensity.

FDTD Simulations.

Full 3-dimensional finite-difference time-domain (FDTD) simulations were performed using a commercial software package (FDTD solutions, Lumerical). A unit cell consisted of a single nanoaperture with 200 nm diameter formed in a 200 nm thick Au film. Periodic boundary conditions in x- and y-directions were used to simulate an infinite array of periodic nanoapertures. Nanoaperture arrays with different periodicities were illuminated with a plain wave from the top (the exosome-binding side). A non-uniform mesh grid with a minimum 2 nm size was applied. The complex dielectric constants for Au were obtained from Palik (Palik, E. D. Handbook of Optical Constants of Solids: Index, Elsevier, 1998), and the glass substate index was set to 1.45 for the simulations.

Microscope Setup.

A conventional upright microscope (Nikon Eclipse Ci) was used for spectral measurements. A 100 W halogen lamp illuminated individual nanoaperture array through a 10× microscope objective, and the transmitted light was collected by an optical fiber placed right underneath the nanoaperture chip. The transmission spectra were analyzed by a miniature fiber-optic VIS-NIR spectrometer (Ocean optics). The integration time was 2 sec and the spectrum was averaged by 5 times.

Portable Imaging Setup.

An integrated CMOS image sensor (Aptina Imaging) was used for imaging measurements. A laser diode at 638 nm with collimating lens and square pattern diffuser was used for illumination. The beam size was adjusted to cover the entire nanoaperture arrays. The nPLEX chip was placed above the image sensor with less than a 2 mm distance and fixed by a plastic holder. The intensities of all the arrays were collected simultaneously and analyzed by a custom-built MATLAB program. The integration time was approximately 5 msec, and the intensities were averaged by 10 times for each image.

Cell Culture.

All human ovarian carcinoma cell lines were obtained from American Type Culture Collection. UCI 101, A2780, OV90 and OVCAR429 were cultured in RPMI-1640 media (Cellgro) containing 10% fetal bovine serum (FBS, Cellgro) and penicillin-streptomycin (Cellgro). CaOV3 and OVCAR 3 were cultured in Dulbecco's modified essential medium (DMEM, Cellgro) supplemented with 10% FBS and penicillin-streptomycin. Immortalized normal ovary epithelial cells (TIOSE 6) were used as a control and cultured in RPMI-1640 supplemented with 10% FBS and penicillin-streptomycin.

Enzyme-Linked Immunosorbant Assay (ELISA).

Exosomes concentrated from cell culture supernatant were adsorbed onto ELISA plates (Thermo Scientific) and blocked overnight in PBS containing 1% bovine serum albumin (BSA, Sigma). For titration determination, concentrated exosome stock was serially diluted in PBS before adsorption. After washing, antibodies were added in blocking solution (1 µg/mL) and incubated for 2 hours at room temperature. Following incubation with horseradish peroxidase-conjugated secondary antibody (Thermo Scientific), chemiluminescence signals were determined (Safire, Tecan).

Flow Cytometry.

Cultured adherent ovarian cells were trypsinized to form cell suspensions. Clinical ascites cells were concentrated by centrifugation and resuspended in PBS with with 0.5% BSA. All cell suspensions were labelled with antibodies (5 µg/mL) for 45 minutes at 4° C. Following centrifugation and aspiration of the antibody solution, cells were labelled with FITC-conjugated secondary antibodies (Abcam) and washed twice by centrifugation. FITC fluorescence was assessed using a LSRII flow cytometer (Becton Dickinson). Mean fluorescence intensity was determined using FlowJo software, and biomarker expression levels were normalized with isotype control antibodies.

Exosome Isolation and Quantification.

Cells at passages 1-15 were cultured in vesicle-depleted medium (with 5% depleted FBS) for 48 hours. Conditioned medium from ~10⁷ cells was collected, filtered through a 0.2 µm membrane filter (Millipore) and concentrated via differential centrifugation as previously described (Skog, J. et al., Nat. Cell Biol. 2008, 10, 1470-1476; Shao, H. et al., Nat. Med. 2012, 18, 1835-1840). For exosome collection from clinical samples, ascites samples were filtered through a 0.2 µm membrane filter (Millipore) to remove cells and debris. The filtrates were used directly for exosomal analysis with the nPLEX sensor. For independent measure of exosome concentrations, the nanoparticle tracking analysis (NTA) system was used (LM10, Nanosight). For the quantification by NTA, exosome concentrations were adjusted to obtain ~50 vesicles in the field of view in order to achieve optimal counting. All NTA measurements were performed with identical system settings for consistency.

Sensor Surface Modification with Antibodies.

The Au nanoaperture surface was first coated with a mixture of polyethylene glycol (PEG) containing long active (carboxylated or biotinylated) thiol-PEG and short inactive methylated thio-PEG (Thermo Scientific, Nanocs) (1:3 active:inactive, 10 mM in PBS). After washing, the surface was either briefly activated with EDC/NHS mixture in MES buffer and conjugated to protein A/G (Thermo Scientific, 2 mg/mL) or used directly for binding with neutravidin (Thermo Scientific, 50 ug/mL). Antibodies targeting the following markers were used without modification (protein A/G linker) or after biotinylation (neutravidin linker): EpCAM (ABCAM, clone MOC-31); CD24 (eBioscience, clone eBioSN3); CA19-9 (Abcam, clone SPM110); Claudin 3 (R&D Systems, clone 385021); CA-125 (Abcam, clone X75); MUC18 (R&D Systems, clone 128018); EGFR (Abcam, clone EGFR.1); HER2 (Biolegend, clone 24D2); CD41 (Biolegend, clone HI30); CD45 (Biolegend, clone HIPS); D2-40 (Abcam, clone D2-40); HSP90 (Abcam, clone AC88); HSP70 (Biolegend, clone W27); CD63 (BD Biosciences, clone H5C6) and respective IgG isotype controls (Biolegend). Antibodies were diluted in blocking solution (50 ug/mL in 2.5% bovine serum albumin (BSA) solution, Sigma), injected into individual sensor channels and incubated for 1 hour at room temperature. Excess unbound antibodies were removed by rinsing in PBS with 0.5% Tween 20 (PBST). Antibody-conjugated sensors were stored in PBS or dried at 4° C. for subsequent use.

Exosome Detection with nPLEX Sensor.

Before introducing exosomes onto the nPLEX sensor, the fluidic channels were flushed with PBS buffer (3 min), and the baseline spectrum was measured. For in vitro assay with exosomes isolated from cell cultures, exosomes were flown to the device at a flow rate of 0.2-2 µl/min. For clinical ascites samples, the filtered ascites were continuously injected at a constant flow rate of 10 µl/min for 15 min. After exosome incubation, the channels were washed by a PBST for 5-10 min at a flow rate of 10 µl/min followed by another set of measurements. The measured spectra and transmitted intensities were analyzed by a custom-designed program (MATLAB).

Clinical Samples.

The study was approved by the Harvard Cancer Center Institutional Review Board. Samples were collected with informed consent. A total of 38 individuals were enrolled. For the profiling study, clinical ascites samples were obtained from ovarian cancer patients (n=20) as well as non-cancer patients (n=10) with ascites-generating conditions. Cancer diagnoses and subtypes were confirmed by histological examination and clinical imaging. For longitudinal treatment response evaluation, serial ascites samples were collected from each patient (n=8) during two distinct treatment visits. Responder and non-responder status was independently assigned by a gynecologic oncologist based on subsequent clinical data. All ascites samples were filtered through a 0.2 µm membrane filter (Millipore) to remove cells and debris. Clinical filtrates were used directly for exosomal analyses with the nPLEX sensor.

Preparation of Gold Nanoparticles.

Spherical gold nanoparticles (Au nanospheres, diameter=10 nm) were purchased (Nanocs), and mixed with biotin-PEG5000-thiol (4.5 mM, 100 µL; Nanocs) for biotinylation. The conjugated Au nanospheres were collected via filtration (Amicon Ultra, Millipore). The star-shaped gold nanoparticles (Au nanostars) were synthesized using seed-mediated growth method (Yuan, H. et al. Nanotechnology 2012, 23, 075102). First, seed Au nanoparticles were prepared through citrate reduction of $HAuCl_4$, as previously reported (Hill, H. D. & Mirkin, C. A. Nat. Protoc. 2006, 1, 324-336); the size of the seed particles was 12 nm. The seed particles (200 µL) were then added to HAuCl$_4$ (0.25 mM, 10 mL) containing HCl (1 M, 10 µL). To the mixture, AgNO$_3$ (2 mM, 100 µL) and ascorbic acid (0.1 M, 50 µL) were sequentially added to initiate the particle growth. The reaction was completed in 30 sec. The prepared Au nanostars were mixed with biotin-PEG5000-thiol (4.5 mM, 100 µL; Nanocs), and processed for biotinylation as mentioned above.

nPLEX Signal Amplification Using Gold Nanoparticles.

Exosomes captured on the nPLEX sensor were subjected to secondary gold nanoparticle labeling for signal enhancement. Briefly, captured exosomes were exposed to biotinylated anti-CD63 antibody (Ancell, 10 µg/mL). After washing, neutravidin (Thermo Scientific, 10 µg/mL) was introduced as a linker into the fluidic channel, before subsequent injection of biotinylated gold nanoparticles. For control channels, equivalent amount of biotinylated IgG istyope control antibody (Ancell) was used to target the captured exosomes.

Western Blotting Analysis.

Exosomes concentrated via ultracentrifugation were lysed in radio-immunoprecipitation assay buffer containing protease inhibitors (Thermo Scientific) and quantified using the bicinchoninic acid assay (BCA assay, Thermo Scientific). Protein lysates were resolved by sodium dodecyl sulfate polyacrylamide gel electrophoresis (SDS-PAGE) and transferred onto polyvinylidene fluoride membrane (PVDF, Invitrogen) and immunoblotted with antibodies against exosomal markers: HSP90 (Cell Signaling), HSP70 (BD Biosciences), Flotillin 1 (BD Biosciences), Flotillin 2 (BD Biosciences), CD9 (Santa Cruz) and CD63 (Santa Cruz); and other vesicular markers: Integrin 131 (Cell Signaling) and Integrin α5 (Cell Signaling). Following incubation with horseradish peroxidase-conjugated secondary antibody (Cell Signaling), enhanced chemiluminescence was used for immunodetection (Thermo Scientific).

Scanning Electron Microscopy.

All samples were fixed with half-strength Karnovsky's fixative and washed twice with PBS. After dehydration in a series of increasing ethanol concentrations, samples were transferred for critical drying (Samdri, Tousimis) and subsequently coated with platinum/palladium using a sputter coater (208HR, Cressington Scientific Instruments), before imaging with a scanning electron microscope (Supra55VP, Carl Zeiss).

Transmission Electron Microscopy.

Exosomes were fixed with 2% paraformaldehyde and transferred onto EM grid. Adsorbed vesicles were washed and subjected to contrast staining with uranyl oxalate (4%) and methyl cellulose (2%) mixture. After air dry, the sample was imaged with a transmission electron microscope (JOEL 2100).

Example 2

Materials and Methods

Figure 20:
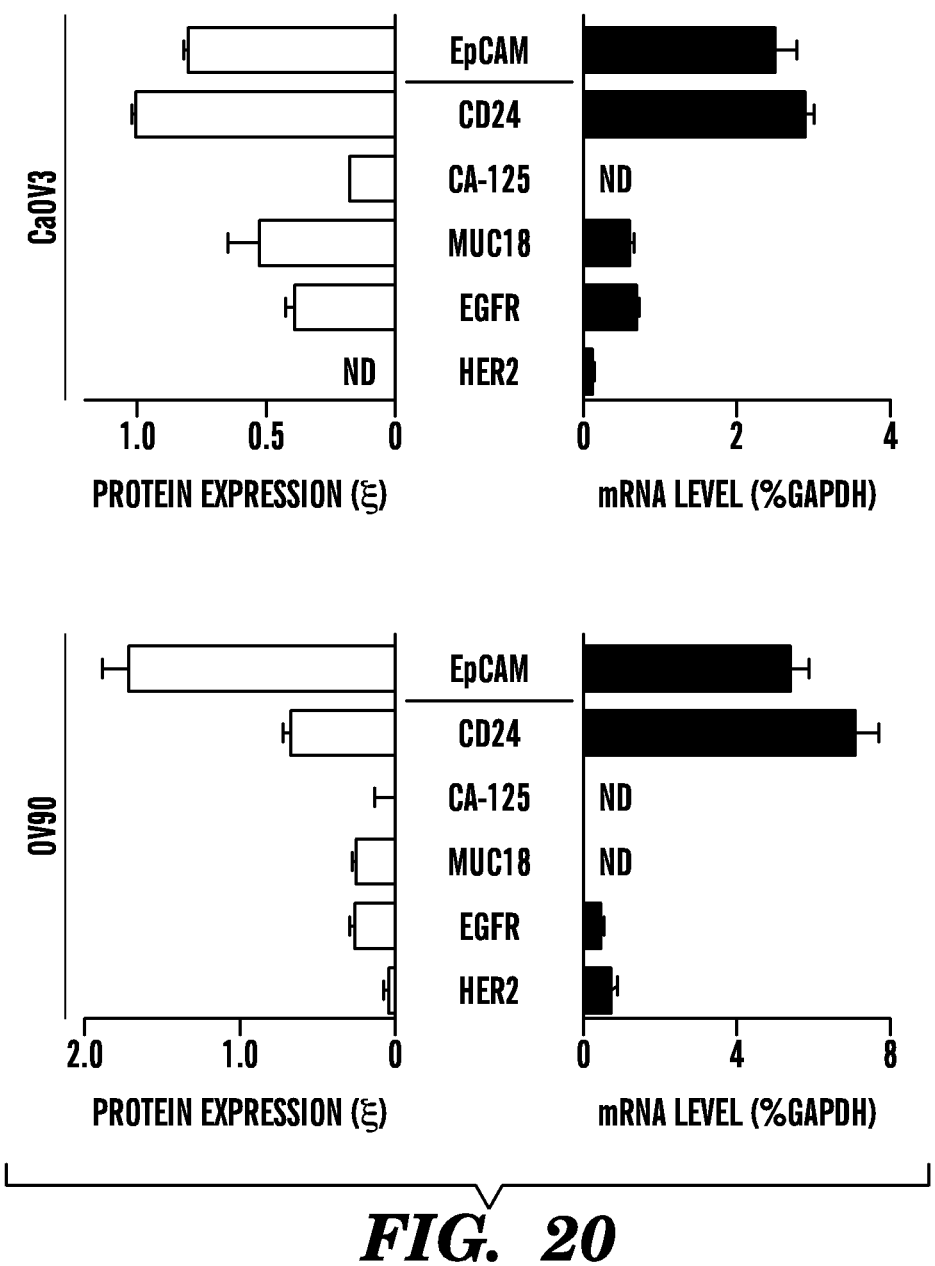
FIG. 20 is a set of graphs of experimental results that demonstrate mRNA analysis of exosomes eluted from CaOV3 cells or OV90 cells. Following nPLEX protein measurements, captured exosomes can be released from the chip for other analyses. In these examples, nPLEX was first used to profile proteins on exosomes from ovarian cancer cells (CaOV3, OV90). Subsequently, exosomes captured on the nPLEX were released and their mRNA contents were probed. The mRNA levels were normalized against glyceraldehyde 3-phosphate dehydrogenase (GAPDH) levels. ND, non-detected.

Exosome Elution and mRNA Analysis (as Shown in FIG. 20).

For elution experiments, the sensor surface was first functionalized with protein A/G (Thermo Scientific) and antibodies. After specific exosome capture, as determined by the real-time sensorgram, bound exosomes and antibodies were eluted by incubating the sensor surface briefly with protein A/G elution buffer (Thermo Scientific) to regenerate the sensor surface and concentrate released exosomes. Eluted exosomes were immediately lysed and processed with mirVANA RNA isolation kit (Life Technologies), according to manufacturer protocol. After RNA extraction, total RNA was quantified with Nanodrop spectrophotometer (Thermo Scientific) and reverse-transcribed to generate first-strand cDNA (Applied Biosystems). qRT-PCR for Taqman mRNA gene expression analyses was performed with diluted cDNA on ABI 7500 Fast Real-Time PCR system (Applied Biosystems). All procedures/experiments were done in triplicate. Cycle threshold ($C_t$) values were analyzed in auto mode and manually inspected for accuracy. Relative quantification was done for each sample by normalizing with respective GAPDH expression.

Figures 21A, 21B:
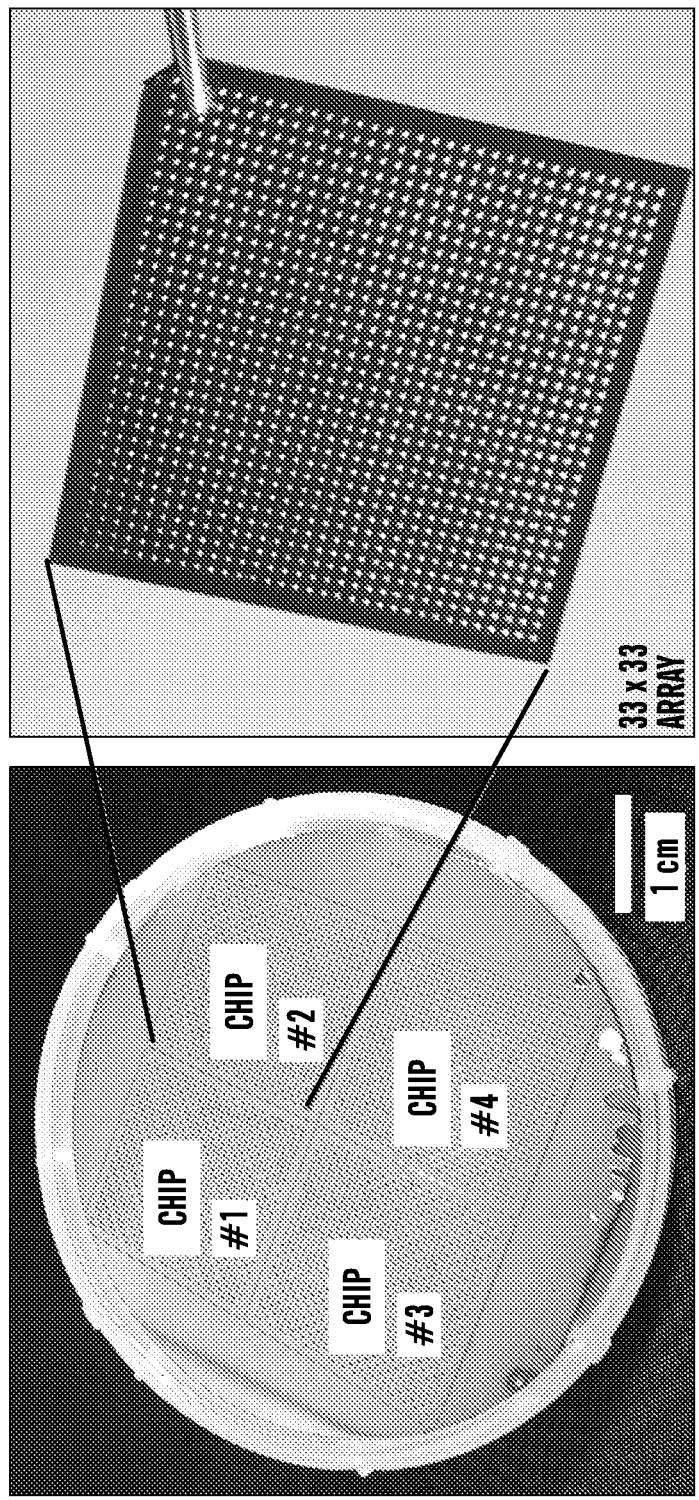
FIG. 21A-FIG. 21D are photographs, micrographs, and a graph of second generation nPLEX chip.
Figure 21D:
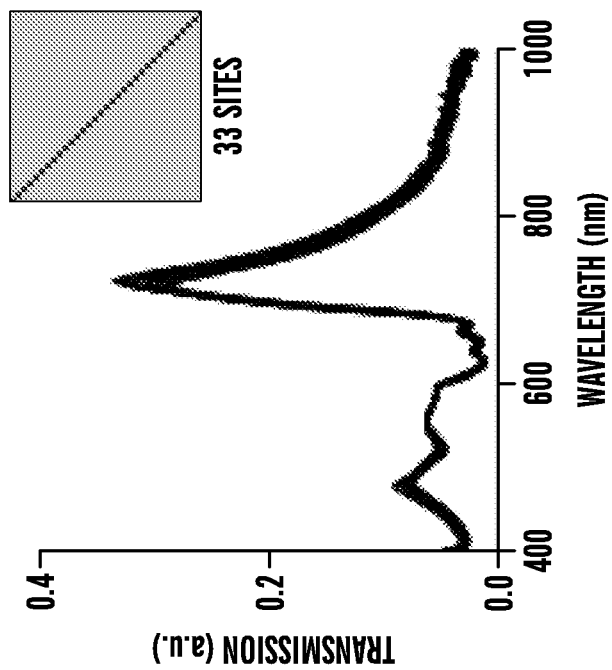
Figure 21C:
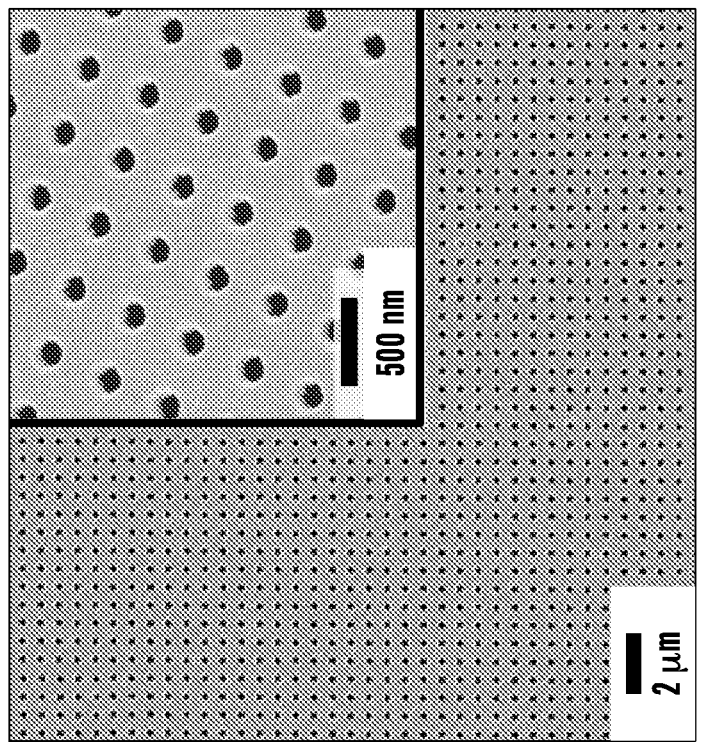
Figure 22A:
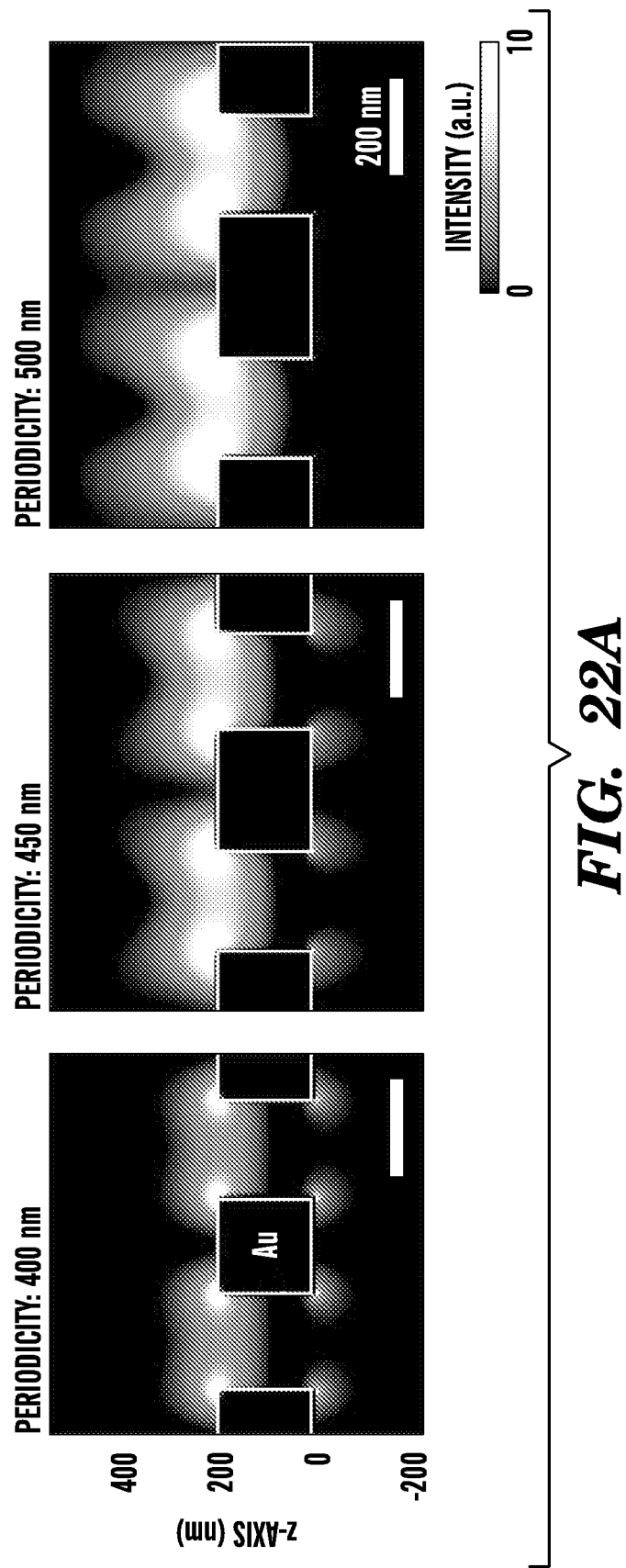
Figure 22B:
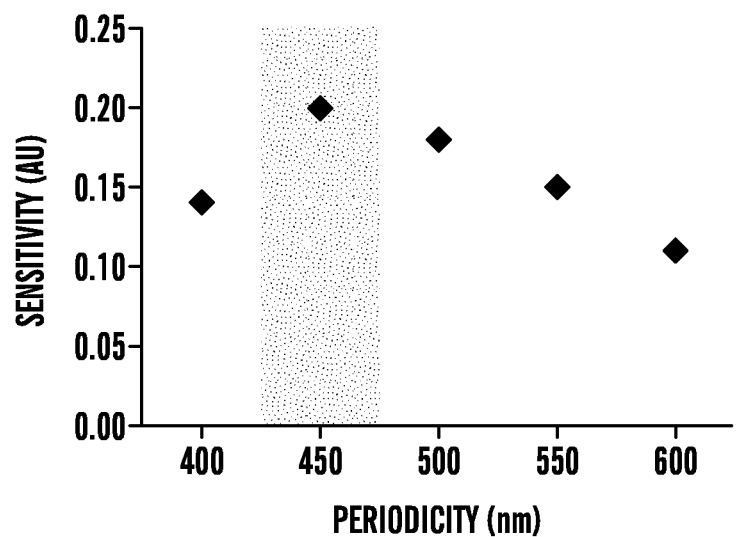
Figure 22C:
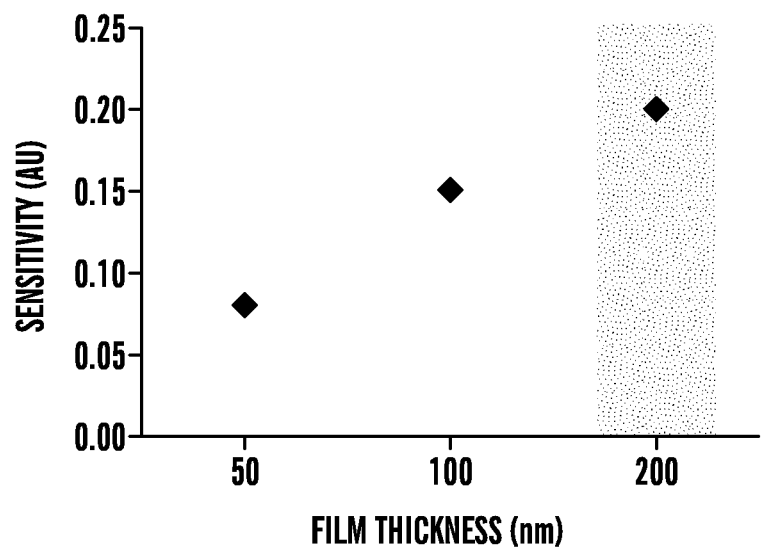
Figure 23A:
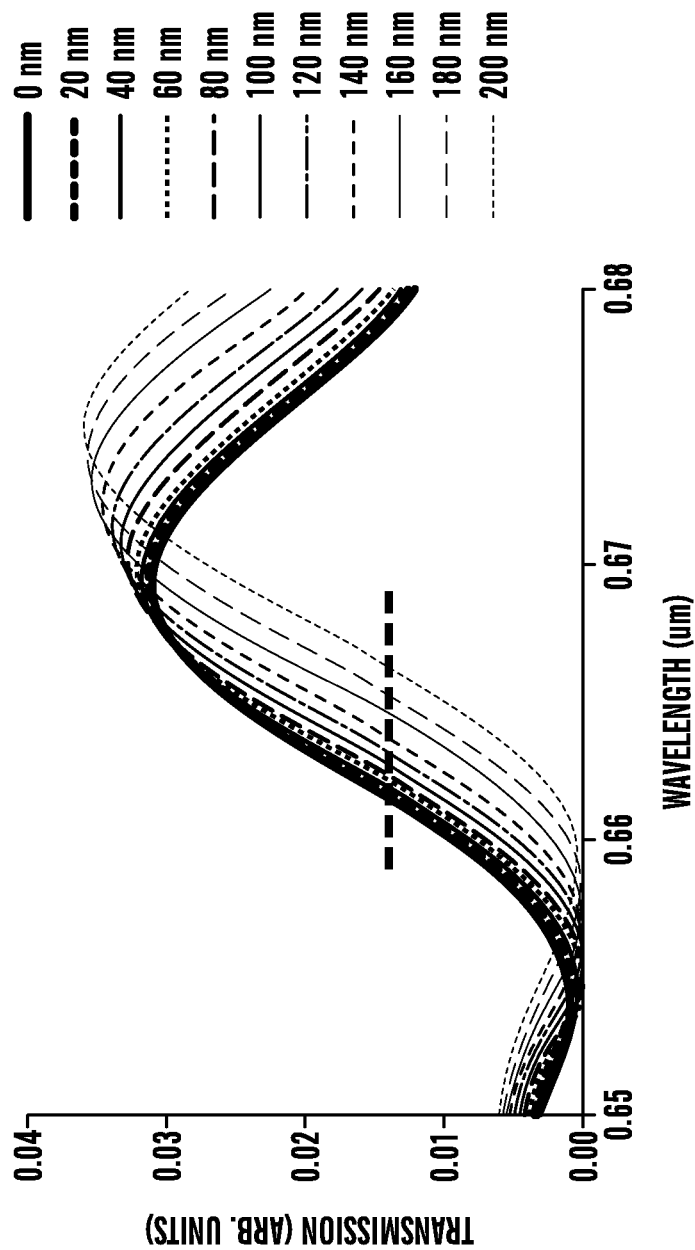
FIG. 23A-FIG. 23C are graphs of simulation results that demonstrate signal amplification with different sizes of nanoparticles.
Figure 23B:
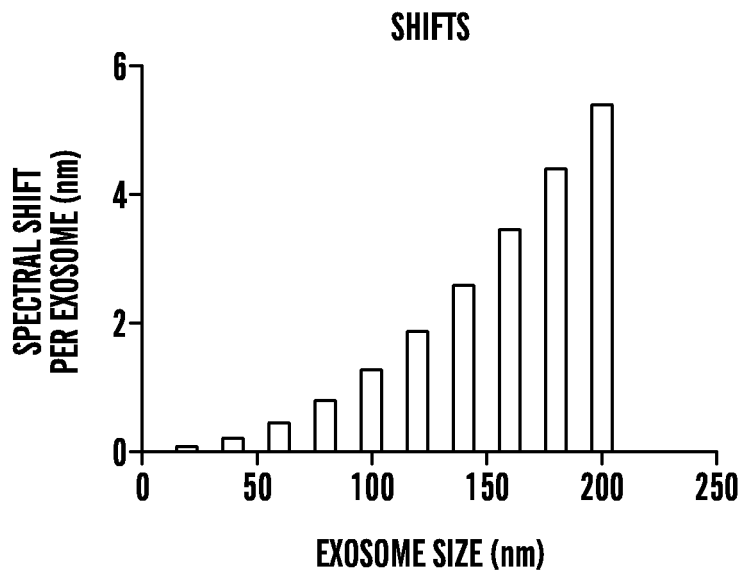
Figure 23C:
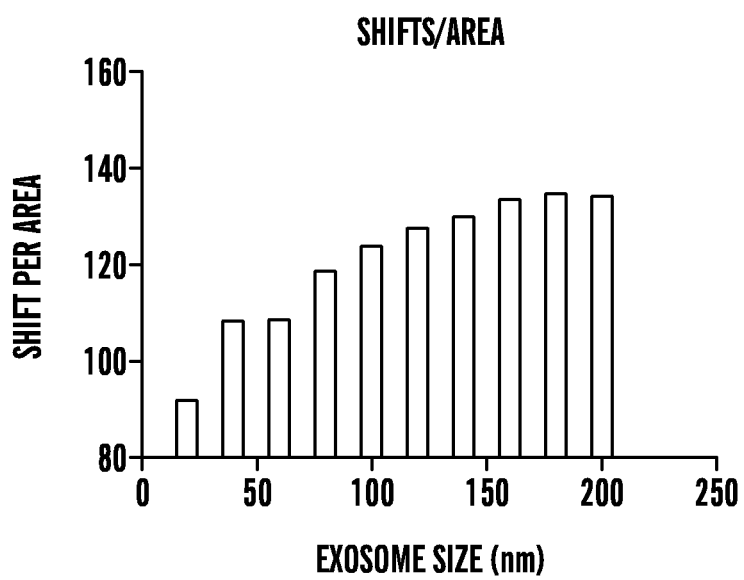
Figure 24:
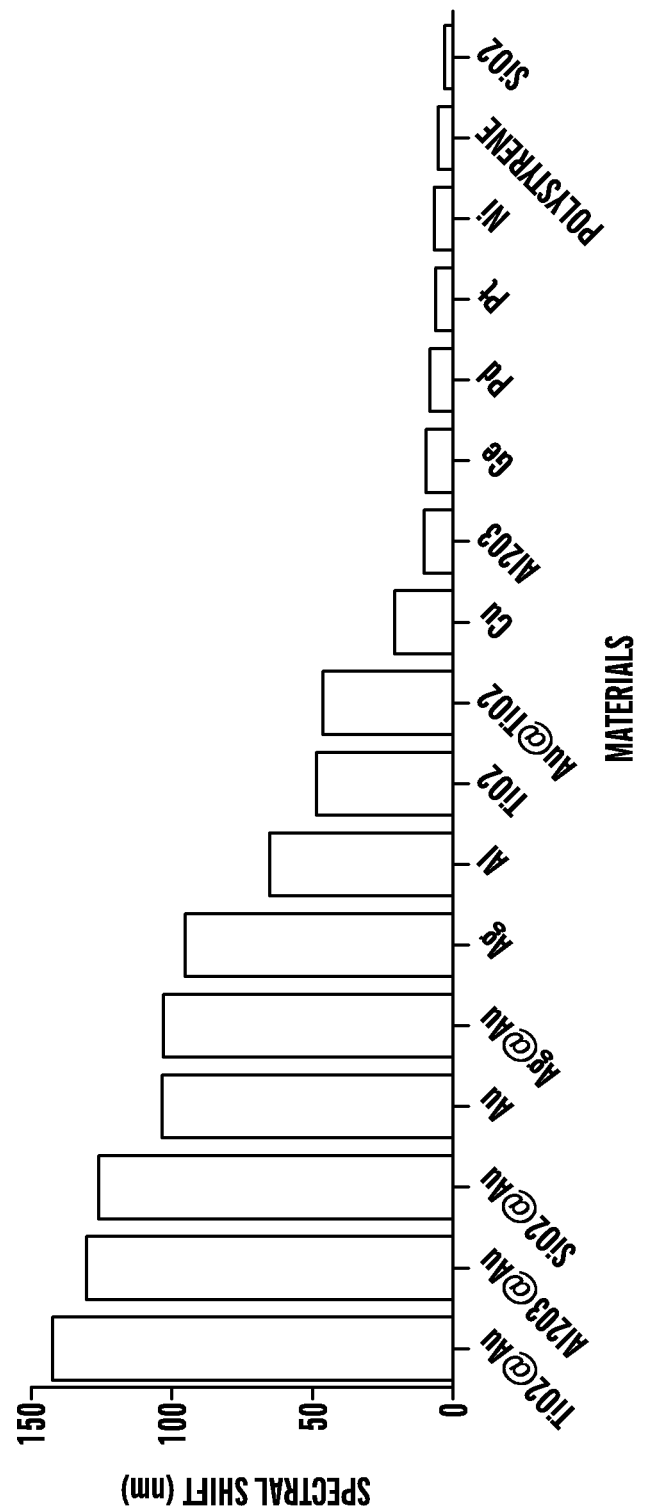
FIG. 24 is a graph of simulated results of signal amplification with different materials of nanoparticles. The graph indicates expected spectral shifts when nanobeads made of different materials are used for signal amplification. The size of particle in this simulation is 100 nm, a mean diameter of exosomes.

2nd Generation nPLEX Chip Fabrication (as Shown in FIG. 21A-FIG. 21C).

A 100 nm-thick low-stress Si$_3$N$_4$ layer was grown on a 4-inch Si wafer using low-pressure chemical vapor deposition (LPCVD). Periodic nanoholes were patterned in the Si$_3$N$_4$ layer using interference lithography followed by reactive ion-etching. The sensing area was defined by standard optical lithography and subsequent isotropic Si wet etching with a diluted KOH solution. A 100 nm Au film with a 2 nm Ti adhesion layer was deposited on the patterned Si using metal evaporation. The used chips can be reused by stripping old Au films and depositing a fresh gold film on the patterned Si wafer.

Figures 25A, 25B:
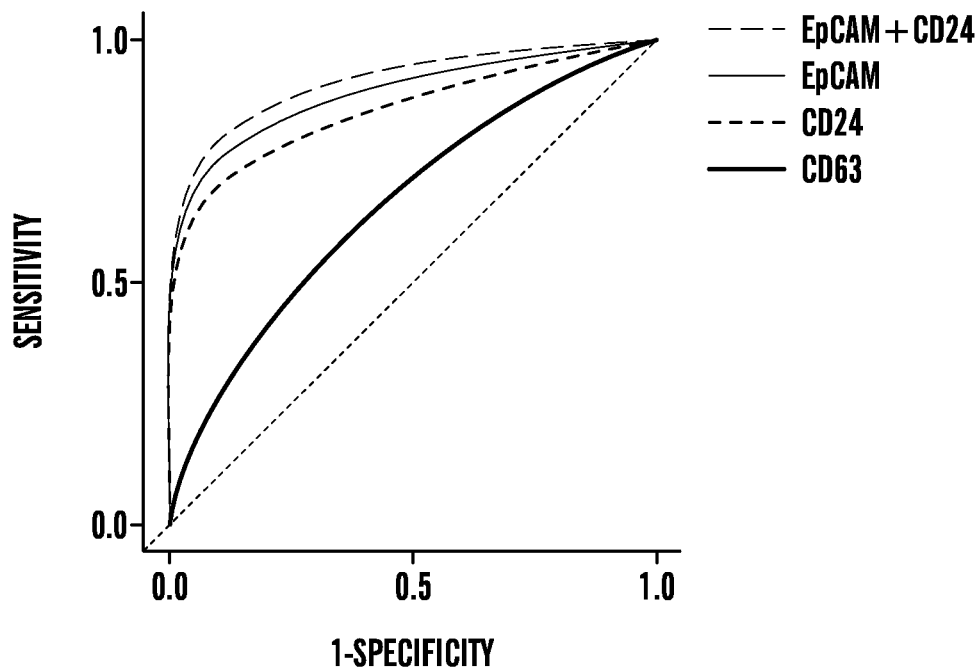
FIG. 25A-FIG. 25B are statistical analyses of patient profiling data.
Figure 26:
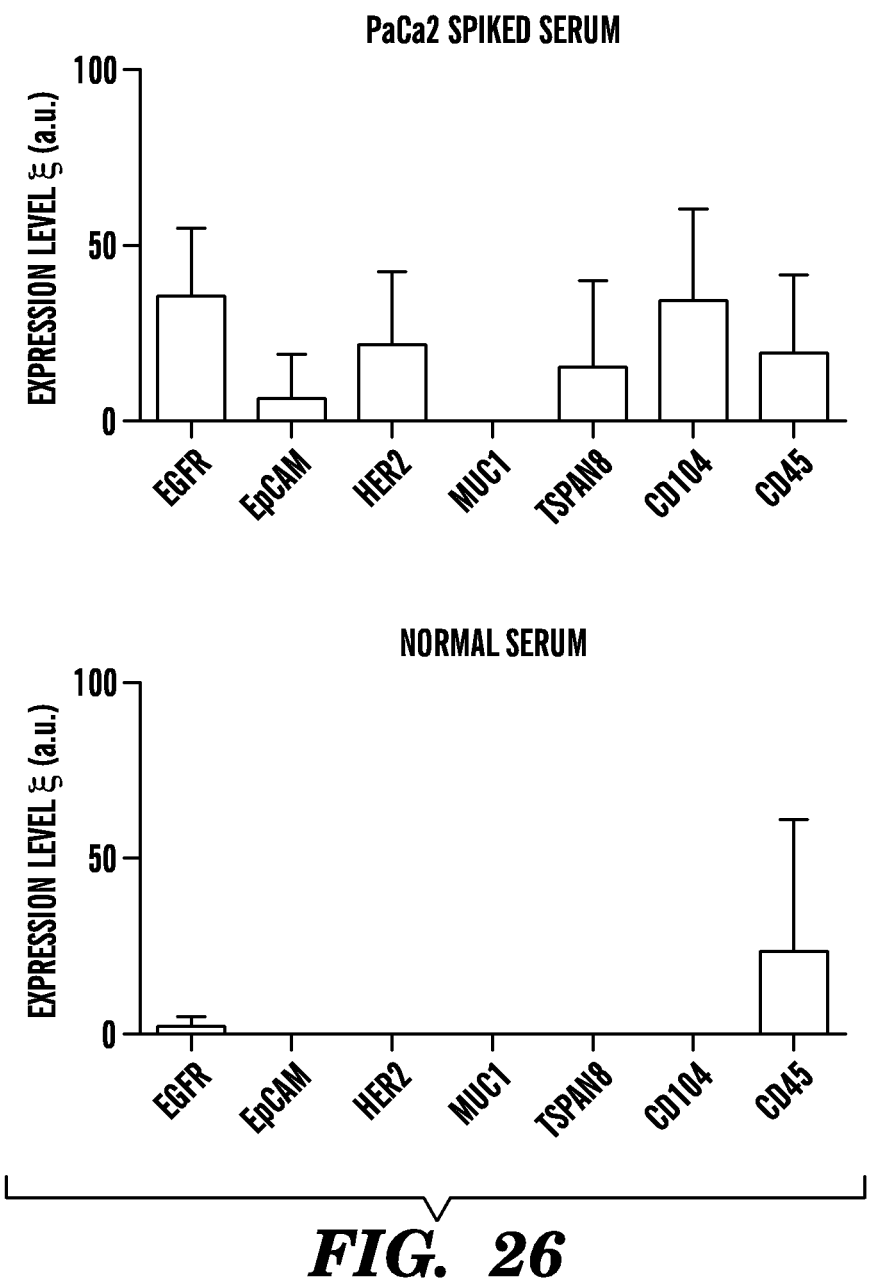
FIG. 26 is a set of graphs of experimental results obtained from the analysis of pancreatic cancer exosomes. Exosomes from a pancreatic cancer cell line (PaCa2) were analyzed for different protein markers by nPLEX. To mimic clinical samples, exosomes were spiked in human serum. The same human serum sample without pancreatic cancer exosomes was also analyzed as a control.
Figure 27:
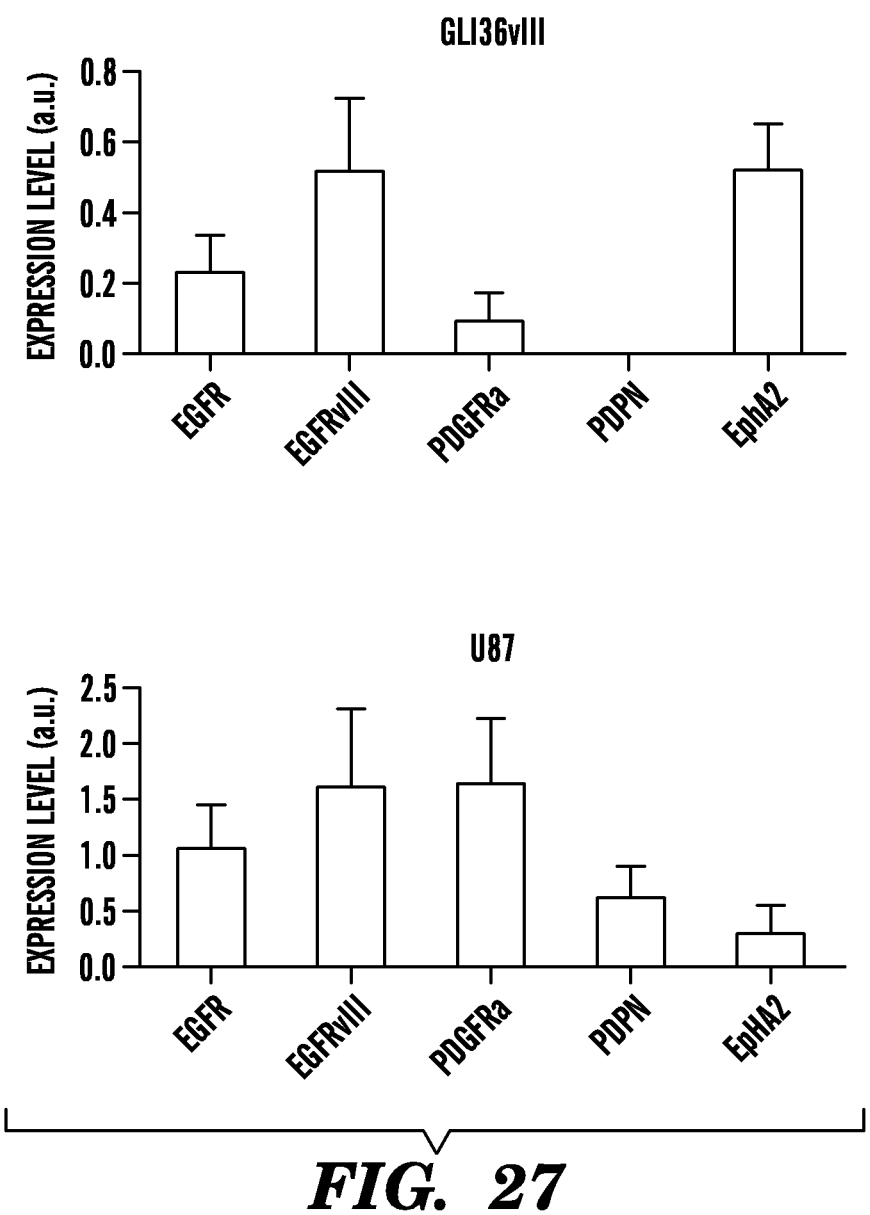
FIG. 27 is a set of graphs of experimental results obtained from the analysis of glioblastoma multiforme (GBM) exosomes. Exosomes from GBM cancer cell lines (GLI36vIII, top; U87, bottom) were analyzed by nPLEX for different protein biomarkers.
Figure 28:
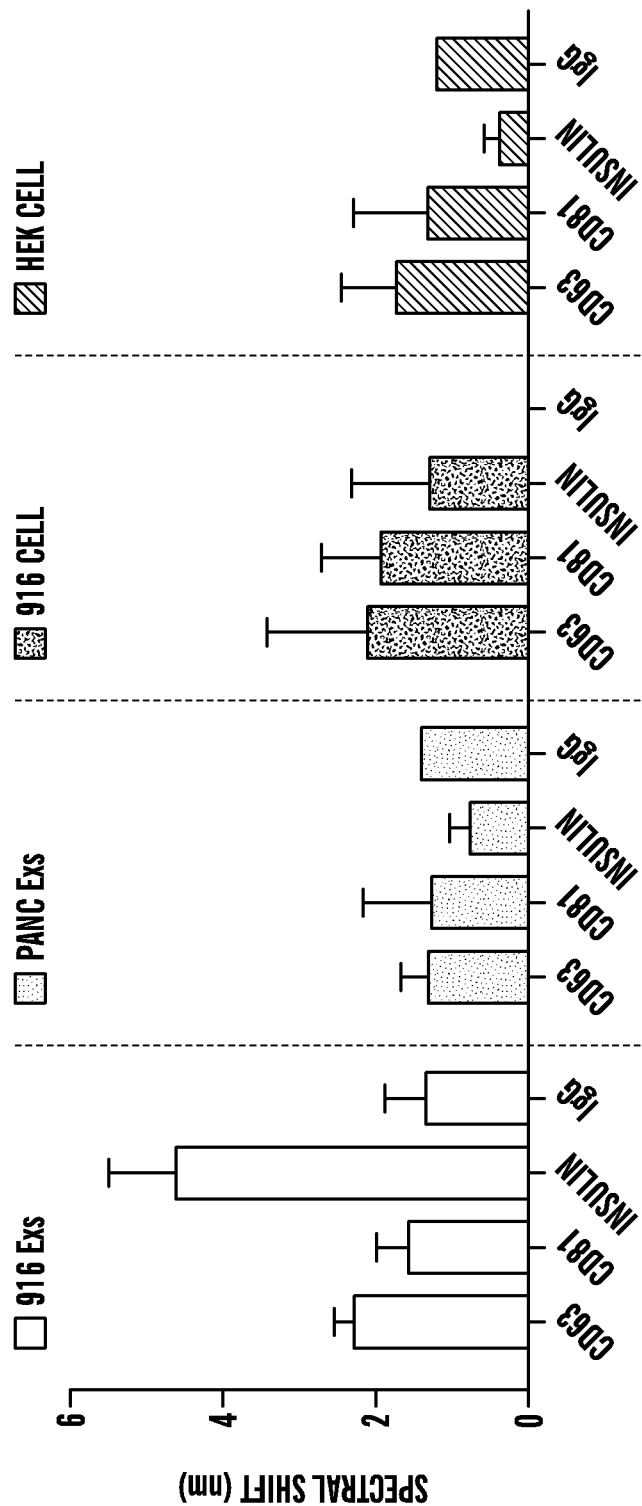
FIG. 28 is a graph of experimental results obtained from the analysis of beta cell exosomes. The nPLEX was used to detect exosomes from beta cells in the islets. Detecting these exosomes can be a new way to quantify the beta cell mass and identify the functional state of islets in assessing the magnitude of autoimmune destruction in type 1 diabetes.

Statistical Analysis (as Shown in FIG. 25A-FIG. 25B).

For the clustering analyses, all protein profiling markers were first sorted and categorized into four different groups (cancer only, ubiquitous, benign only, absent), according to their expression status in cancer and benign cell lines (defined by whether the markers were present or absent in either benign or malignant cells). Subsequently, the markers in each category were clustered using (1−P) as the distance metric (P, Pearson correlation). Receiver operation characteristic (ROC) curves for CD63, EpCAM and CD24 were generated from patient profiling data. Note that exosomal expression of EpCAM and CD24 was used. When combining EpCAM and CD24 profiles, an arithmetic average of EpCAM and CD24 levels was used as an independent variable. The optimal cutoff value for each marker was established by determining the point closest to the top-left corner (perfect sensitivity or specificity) of the ROC curve. All diagnostic metrics (i.e., sensitivity, specificity, accuracy) were calculated using standard formulas. The empirical ROC curves were smoothed with the binormal fitting model. R package (version 3.0.2) was used for ROC curve analyses. The experiments were not randomized.

TABLE 2

List of protein markers and their antibodies used in the profiling.

| Protein Marker | Description | Antibody |
|---|---|---|
| EpCAM | Epithelial cell adhesion molecule, transmembrane glycoprotein expressed exclusively in epithelial and epithelial derived neoplasms. | Abcam, clone MOC-31 |
| CD24 | A small heavily glycosylated cell adhesion molecule, expressed in hematological malignancies and a variety of solid tumors. | eBioscience, clone eBioSN3 |
| CA19-9 | Cancer antigen 19-9, a carbohydrate tumor-associated antigen, found in a wide range of malignant conditions including ovarian carcinomas. | Abcam, clone SPM110 |
| CLDN3 | Claudin 3, a transmembrane protein crucial in the formation and function of tight junctions, associated with elevated expression in ovarian cancer. | R&D Systems, clone 385021 |

TABLE 2-continued

List of protein markers and their antibodies used in the profiling.

| Protein Marker | Description | Antibody |
|---|---|---|
| CA-125 | Cancer antigen 125, also known as mucin 16, a member of the mucin family glycoprotein, and is the most frequently used biomarker for ovarian cancer detection. | Abcam, clone X75 |
| MUC18 | Mucin 18, a cell surface glycoprotein and cell adhesion molecule whose expression is a prognostic marker in epithelial ovarian cancer. | R&D Systems, clone 128018 |
| EGFR | Epidermal growth factor receptor, a cell-surface receptor whose overexpression and mutations have been associated with many cancers. | Abcam, clone EGFR.1 |
| HER2 | Human epidermal growth factor receptor 2, also known as receptor tyrosine kinase erbB-2, whose overexpression plays a major role in the development and progression of multiple cancers. | Biolegend, clone 24D2 |
| CD41 | Also known as integrin alpha chain 2b, a heterodimeric integral membrane protein expressed on platelets. | Biolegend, clone HI30 |
| CD45 | Encoded by the PTPRC gene, a type I transmembrane protein expressed on all leukocytes. | Biolegend, clone HIP8 |
| D2-40 | A surface sialoglycoprotein used to distinguish mesothelial cells from adenocarcinoma. | Abcam, clone D2-40 |
| CD63 | A type III lysosomal membrane protein abundant and characteristic in exosomes. | BD Biosciences, clone H5C6 |

TABLE 3

Clinical information on patient samples used in molecular profiling.

| Characteristic | Molecular Profile Number (%) |
|---|---|
| Non Cancer Ascites | 10 |
| Cirrhosis | 10 (100%) |
| Heart failure | 0 |
| Ascites Volume (L) | |
| (mean/range) | 5.6 (2.0-8.8) |
| Ovarian Cancer | 20 |
| Histology | |
| Serous | 16 (80%) |
| Mucinous | 1 (5%) |
| Mixed | 1 (5%) |
| Poorly Differentiated | 2 (10%) |
| Ascites Volume (L) | |
| (mean/range) | 2.8 (1.1-6.4) |

TABLE 4

Clinical information on patient samples used in treatment monitoring.

| Characteristic | Molecular Profile Number (%) |
|---|---|
| Ovarian Cancer | 20 |
| Responders | 4 (50%) |
| Histology | |
| Serous | 2 (50%) |
| Mucinous | 1 (25%) |
| Mixed | 1 (25%) |
| Poorly Differentiated | 0 |

TABLE 4-continued

Clinical information on patient samples used in treatment monitoring.

| Characteristic | Molecular Profile Number (%) |
|---|---|
| Stage | |
| IIIC | 1 (25%) |
| IV | 3 (75%) |
| Ascites Volume (L) | |
| (mean/range) | 2.5 (1.0-4.5) |
| Non-Responders | 4 (50%) |
| Histology | |
| Serous | 3 (75%) |
| Mucinous | 0 |
| Mixed | 0 |
| Poorly Differentiated | 1 (25%) |
| Stage | |
| IIIC | 3 (75%) |
| IV | 1 (25%) |
| Ascites Volume (L) | |
| (mean/range) | 2.6 (0.4-3.9) |

What is claimed is:

1. A nano-plasmonic sensor for detecting exosomes comprising,
   a) a transparent planar substrate;
   b) a metal film disposed onto one surface of the substrate, wherein the metal film comprises a plurality of nano-apertures in a predefined pattern to create a sensing area that produces surface plasmon resonance upon illumination;
   c) a molecular spacer directly attached to the metal film, wherein the molecular spacer comprises long-chain PEG and short-chain PEG in a ratio of about 1:3; and
   d) a linking agent directly attached to the molecular spacer and directly attached to a capture agent, wherein the capture agent specifically binds to an exosome marker.

2. The nano-plasmonic sensor of claim 1, wherein the metal film comprises a noble metal, a transition metal, an alkali metal, or any combination thereof.

3. The nano-plasmonic sensor of claim 2, wherein the substrate comprises glass, quartz, diamond, or a polymer.

4. The nano-plasmonic sensor of claim 3, wherein the metal film comprises gold and the substrate comprises glass.

5. The nano-plasmonic sensor of claim 4, wherein the metal film is between 50 to 500 nm thick.

6. The nano-plasmonic sensor of claim 5, further comprising an adhesion layer located between the metal film and the substrate surface.

7. The nano-plasmonic sensor of claim 6, wherein the adhesion layer is less than about 50 nm thick.

8. The nano-plasmonic sensor of claim 7, wherein the predefined pattern is periodic.

9. The nano-plasmonic sensor of claim 8, wherein the nanoapertures have a dimension and periodicity that produce an electromagnetic field with a decay length of about 50 nm to 200 nm when the nanoapertures are illuminated by light with a wavelength close to or at the surface plasmon resonance.

10. The nano-plasmonic sensor of claim 9, wherein the nanoapertures are circular, elliptical, rectangular, triangular, oval, or hexagonal.

11. The nano-plasmonic sensor of claim 10, wherein the circular nanoapertures are about 50 nm to 300 nm in diameter, and wherein the periodicity is about 400 nm to 700 nm.

12. The nano-plasmonic sensor of claim 11, wherein the circular nanoapertures are about 200 nm in diameter, and wherein the periodicity is about 450 nm to 500 nm.

13. The nano-plasmonic sensor of claim 1, wherein the linking agent comprises protein A/G or neutravidin.

14. A method of detecting exosomes in a sample, comprising
  a) introducing a sample suspected of containing one or more exosomes onto a nano-plasmonic sensor of claim 1 under conditions which promote binding of the exosomes to the sensor;
  b) washing the sensor to remove unbound materials;
  c) illuminating the sensor to thereby transmit light through the sensor;
  d) measuring the light transmitted through the sensor to identify a significant change from that of a negative control; and
  e) detecting exosomes in the sample when the significant change m the transmitted light is identified.

15. The method of claim 14, wherein the negative control is a solution substantially free of exosomes or exosome lysates.

16. The method of claim 14, wherein the change is a shift in peak wavelength.

17. A method for determining an expression level of a target marker in a sample of exosomes, comprising:
  a) detecting total exosomes in the sample by the method of claim 14, using a capture agent that specifically binds a pan-exosomal marker;
  b) detecting exosomes in the sample expressing the target marker by the method of claim 14 using a capture agent that specifically binds the target marker; and
  c) calculating the ratio of exosomes with the target marker to total exosomes to thereby indicate the average expression level of the target marker per exosome from the sample.

* * * * *